(12) United States Patent
Do Valle et al.

(10) Patent No.: US 11,607,132 B2
(45) Date of Patent: Mar. 21, 2023

(54) TEMPORAL RESOLUTION CONTROL FOR TEMPORAL POINT SPREAD FUNCTION GENERATION IN AN OPTICAL MEASUREMENT SYSTEM

(71) Applicant: HI LLC, Los Angeles, CA (US)

(72) Inventors: Bruno Do Valle, Brighton, MA (US); Ryan Field, Culver City, CA (US); Rong Jin, Acton, MA (US); Jacob Dahle, Arlington, MA (US)

(73) Assignee: HI LLC, Los Angeles, CA (US)

( * ) Notice: Subject to any disclaimer, the term of this patent is extended or adjusted under 35 U.S.C. 154(b) by 1 day.

(21) Appl. No.: 17/202,598

(22) Filed: Mar. 16, 2021

(65) Prior Publication Data

US 2021/0290064 A1    Sep. 23, 2021

Related U.S. Application Data

(60) Provisional application No. 63/027,025, filed on May 19, 2020, provisional application No. 62/992,506, filed on Mar. 20, 2020.

(51) Int. Cl.
*A61B 5/00*     (2006.01)
*G01R 31/317*   (2006.01)
(Continued)

(52) U.S. Cl.
CPC .......... *A61B 5/0059* (2013.01); *A61B 5/4064* (2013.01); *A61B 5/486* (2013.01);
(Continued)

(58) Field of Classification Search
None
See application file for complete search history.

(56) References Cited

U.S. PATENT DOCUMENTS

| 4,018,534 A | 4/1977 | Thorn et al. |
| 4,207,892 A | 6/1980 | Binder |

(Continued)

FOREIGN PATENT DOCUMENTS

| CN | 200950235 | 9/2007 |
| CN | 107865635 | 4/2018 |

(Continued)

OTHER PUBLICATIONS

Fisher, et al.,"A Reconfigurable Single-Photon-Counting Integrating Receiver for Optical Communications," IEEE Journal of Solid-State Circuits, vol. 48, No. 7, Jul. 2013, https://www.researchgate.net/publication/260626902.

(Continued)

*Primary Examiner* — Alex M Valvis
*Assistant Examiner* — Aurelie H Tu
(74) *Attorney, Agent, or Firm* — ALG Intellectual Property, LLC

(57) ABSTRACT

An exemplary system includes a photodetector configured to generate a plurality of photodetector output pulses over time as a plurality of light pulses are applied to and scattered by a target, a TPSF generation circuit configured to generate, based on the photodetector output pulses, a TPSF representative of a light pulse response of the target, and a control circuit configured to direct the TPSF generation circuit to selectively operate in different resolution modes.

22 Claims, 29 Drawing Sheets

(51) Int. Cl.
*G01R 31/30* (2006.01)
*G01R 31/319* (2006.01)

(52) U.S. Cl.
CPC ...... *A61B 5/6803* (2013.01); *G01R 31/31725* (2013.01); *G01R 31/3016* (2013.01); *G01R 31/31922* (2013.01); *G01R 31/31924* (2013.01)

(56) References Cited

U.S. PATENT DOCUMENTS

| | | | |
|---|---|---|---|
| 4,281,645 A | 8/1981 | Jobsis | |
| 4,321,930 A | 3/1982 | Jobsis | |
| 4,515,165 A | 5/1985 | Carroll | |
| 4,655,225 A | 4/1987 | Dahne et al. | |
| 4,928,248 A | 5/1990 | Takahashi et al. | |
| 4,963,727 A | 10/1990 | Cova | |
| 4,995,044 A | 2/1991 | Blazo | |
| 5,088,493 A | 2/1992 | Giannini | |
| 5,090,415 A | 2/1992 | Yamashita | |
| 5,309,458 A | 5/1994 | Carl | |
| 5,386,827 A | 2/1995 | Chance et al. | |
| 5,528,365 A | 6/1996 | Gonatas et al. | |
| 5,625,458 A | 4/1997 | Alfano et al. | |
| 5,761,230 A | 6/1998 | Oono et al. | |
| 5,853,370 A | 12/1998 | Chance et al. | |
| 5,895,984 A | 4/1999 | Renz | |
| 5,929,982 A | 7/1999 | Anderson | |
| 5,983,120 A | 11/1999 | Groner et al. | |
| 5,987,045 A | 11/1999 | Albares et al. | |
| 6,163,715 A | 12/2000 | Larsen et al. | |
| 6,240,309 B1 | 5/2001 | Yamashita et al. | |
| 6,384,663 B2 | 5/2002 | Cova et al. | |
| 6,541,752 B2 | 4/2003 | Zappa et al. | |
| 6,640,133 B2 | 10/2003 | Yamashita | |
| 6,683,294 B1 | 1/2004 | Herbert et al. | |
| 6,748,254 B2 | 6/2004 | O'Neil | |
| 6,992,772 B2 | 1/2006 | Block | |
| 7,095,491 B2 | 8/2006 | Forstner et al. | |
| 7,356,365 B2 | 4/2008 | Schurman | |
| 7,507,596 B2 | 3/2009 | Yaung et al. | |
| 7,547,872 B2 | 6/2009 | Niclass et al. | |
| 7,613,504 B2 | 11/2009 | Rowe | |
| 7,667,400 B1 | 2/2010 | Goushcha | |
| 7,705,284 B2 | 4/2010 | Inoue et al. | |
| 7,714,292 B2 | 5/2010 | Agarwal et al. | |
| 7,774,047 B2 | 8/2010 | Yamashita et al. | |
| 7,899,506 B2 | 3/2011 | Xu et al. | |
| 8,026,471 B2 | 9/2011 | Itzler | |
| 8,078,250 B2 | 12/2011 | Chen et al. | |
| 8,082,015 B2 | 12/2011 | Yodh et al. | |
| 8,115,170 B2 | 2/2012 | Stellari et al. | |
| 8,168,934 B2 | 5/2012 | Niclass et al. | |
| 8,352,012 B2 | 1/2013 | Besio | |
| 8,633,431 B2 | 1/2014 | Kim | |
| 8,637,875 B2 | 1/2014 | Finkelstein et al. | |
| 8,754,378 B2 | 6/2014 | Prescher et al. | |
| 8,817,257 B2 | 8/2014 | Herve | |
| 8,937,509 B2 | 1/2015 | Xu et al. | |
| 8,986,207 B2 | 3/2015 | Li | |
| 9,012,860 B2 | 4/2015 | Nyman et al. | |
| 9,041,136 B2 | 5/2015 | Chia | |
| 9,058,081 B2 | 6/2015 | Baxter | |
| 9,076,707 B2 | 7/2015 | Harmon | |
| 9,101,279 B2 | 8/2015 | Ritchey et al. | |
| 9,131,861 B2 | 9/2015 | Ince et al. | |
| 9,157,858 B2 | 10/2015 | Claps | |
| 9,160,949 B2 | 10/2015 | Zhang et al. | |
| 9,176,241 B2 | 11/2015 | Frach | |
| 9,178,100 B2 | 11/2015 | Webster et al. | |
| 9,190,552 B2 | 11/2015 | Brunel et al. | |
| 9,201,138 B2 | 12/2015 | Eisele et al. | |
| 9,209,320 B1 | 12/2015 | Webster | |
| 9,257,523 B2 | 2/2016 | Schneider et al. | |
| 9,257,589 B2 | 2/2016 | Niclass et al. | |
| 9,299,732 B2 | 3/2016 | Webster et al. | |
| 9,299,873 B2 | 3/2016 | Mazzillo et al. | |
| 9,312,401 B2 | 4/2016 | Webster | |
| 9,316,735 B2 | 4/2016 | Baxter | |
| 9,331,116 B2 | 5/2016 | Webster | |
| 9,368,487 B1 | 6/2016 | Su et al. | |
| 9,401,448 B2 | 7/2016 | Bienfang et al. | |
| 9,407,796 B2 | 8/2016 | Dinten et al. | |
| 9,419,635 B2 | 8/2016 | Kumar et al. | |
| 9,431,439 B2 | 8/2016 | Soga et al. | |
| 9,442,201 B2 | 9/2016 | Schmand et al. | |
| 9,449,377 B2 | 9/2016 | Sarkar et al. | |
| 9,450,007 B1 | 9/2016 | Motta et al. | |
| 9,466,631 B2 | 10/2016 | Fallica et al. | |
| 9,476,979 B2 | 10/2016 | Drader et al. | |
| 9,478,579 B2 | 10/2016 | Dai et al. | |
| 9,529,079 B1 | 12/2016 | Droz | |
| 9,535,157 B2 | 1/2017 | Caley et al. | |
| 9,574,936 B2 | 2/2017 | Heinonen | |
| 9,625,580 B2 | 4/2017 | Kotelnikov et al. | |
| 9,627,569 B2 | 4/2017 | Harmon | |
| 9,634,826 B1 * | 4/2017 | Park | H03M 1/0607 |
| 9,639,063 B2 | 5/2017 | Dutton et al. | |
| 9,640,704 B2 | 5/2017 | Frey et al. | |
| 9,658,158 B2 | 5/2017 | Renna et al. | |
| 9,659,980 B2 | 5/2017 | McGarvey et al. | |
| 9,671,284 B1 | 6/2017 | Dandin | |
| 9,681,844 B2 | 6/2017 | Xu et al. | |
| 9,685,576 B2 | 6/2017 | Webster | |
| 9,702,758 B2 | 7/2017 | Nouri | |
| 9,728,659 B2 | 8/2017 | Hirigoyen et al. | |
| 9,741,879 B2 | 8/2017 | Frey et al. | |
| 9,753,351 B2 | 9/2017 | Eldada | |
| 9,767,246 B2 | 9/2017 | Dolinsky et al. | |
| 9,768,211 B2 | 9/2017 | Harmon | |
| 9,773,930 B2 | 9/2017 | Motta et al. | |
| 9,804,092 B2 | 10/2017 | Zeng et al. | |
| 9,812,438 B2 | 11/2017 | Schneider et al. | |
| 9,831,283 B2 | 11/2017 | Shepard et al. | |
| 9,851,302 B2 | 12/2017 | Mattioli Della Rocca et al. | |
| 9,867,250 B1 | 1/2018 | Powers et al. | |
| 9,869,753 B2 | 1/2018 | Eldada | |
| 9,881,963 B1 | 1/2018 | Chen et al. | |
| 9,882,003 B1 | 1/2018 | Aharoni | |
| 9,886,095 B2 | 2/2018 | Pothier | |
| 9,899,544 B1 | 2/2018 | Mazzillo et al. | |
| 9,899,557 B2 | 2/2018 | Muscara' et al. | |
| 9,939,316 B2 | 4/2018 | Scott et al. | |
| 9,939,536 B2 | 4/2018 | O'Neill et al. | |
| 9,946,344 B2 | 4/2018 | Ayaz et al. | |
| D817,553 S | 5/2018 | Aaskov et al. | |
| 9,983,670 B2 | 5/2018 | Coleman | |
| 9,997,551 B2 | 6/2018 | Mandai et al. | |
| 10,016,137 B1 | 7/2018 | Yang et al. | |
| D825,112 S | 8/2018 | Saez | |
| 10,056,415 B2 | 8/2018 | Na et al. | |
| 10,103,513 B1 | 10/2018 | Zhang et al. | |
| 10,141,458 B2 | 11/2018 | Zhang et al. | |
| 10,157,954 B2 | 12/2018 | Na et al. | |
| 10,158,038 B1 | 12/2018 | Do Valle et al. | |
| 10,219,700 B1 | 3/2019 | Yang et al. | |
| 10,256,264 B2 | 4/2019 | Na et al. | |
| 10,340,408 B1 | 7/2019 | Katnani | |
| 10,424,683 B1 | 9/2019 | Do Valle | |
| 10,483,125 B2 | 11/2019 | Inoue | |
| 10,515,993 B2 | 12/2019 | Field et al. | |
| 10,533,893 B2 | 1/2020 | Leonardo | |
| 10,558,171 B2 | 2/2020 | Kondo | |
| 10,594,306 B2 | 3/2020 | Dandin | |
| 10,627,460 B2 | 4/2020 | Alford et al. | |
| 10,697,829 B2 | 6/2020 | Delic | |
| 10,772,561 B2 | 9/2020 | Donaldson | |
| 10,809,796 B2 | 10/2020 | Armstrong-Muntner | |
| 10,825,847 B2 | 11/2020 | Furukawa | |
| 10,912,504 B2 | 2/2021 | Nakaji | |
| 10,976,386 B2 | 4/2021 | Alford | |
| 10,983,177 B2 | 4/2021 | Jiménez-Martínez | |
| 10,996,293 B2 | 5/2021 | Mohseni | |
| 11,006,876 B2 | 5/2021 | Johnson | |
| 11,006,878 B2 | 5/2021 | Johnson | |
| 2002/0195545 A1 | 12/2002 | Nishimura | |

(56) References Cited

U.S. PATENT DOCUMENTS

| | | |
|---|---|---|
| 2004/0057478 A1 | 3/2004 | Saito |
| 2004/0078216 A1 | 4/2004 | Toto |
| 2004/0160996 A1 | 8/2004 | Giorgi et al. |
| 2005/0038344 A1 | 2/2005 | Chance |
| 2005/0061986 A1 | 3/2005 | Kardynal et al. |
| 2005/0124863 A1* | 6/2005 | Cook .................... A61B 5/4094 600/300 |
| 2005/0228291 A1 | 10/2005 | Chance |
| 2006/0171845 A1 | 8/2006 | Martin |
| 2006/0197452 A1 | 9/2006 | Zhang |
| 2007/0038116 A1 | 2/2007 | Yamanaka |
| 2007/0083097 A1 | 4/2007 | Fujiwara |
| 2008/0021341 A1 | 1/2008 | Harris et al. |
| 2009/0012402 A1 | 1/2009 | Mintz |
| 2009/0054789 A1 | 2/2009 | Kiguchi et al. |
| 2009/0163775 A1 | 6/2009 | Barrett |
| 2009/0313048 A1 | 12/2009 | Kahn et al. |
| 2010/0210952 A1 | 8/2010 | Taira et al. |
| 2010/0301194 A1 | 12/2010 | Patel |
| 2011/0208675 A1 | 8/2011 | Shoureshi et al. |
| 2011/0248175 A1 | 10/2011 | Frach |
| 2012/0016635 A1 | 1/2012 | Brodsky et al. |
| 2012/0029304 A1 | 2/2012 | Medina et al. |
| 2012/0083673 A1 | 4/2012 | Al-Ali et al. |
| 2012/0101838 A1 | 4/2012 | Lingard et al. |
| 2013/0015331 A1 | 1/2013 | Birk |
| 2013/0030267 A1 | 1/2013 | Lisogurski |
| 2013/0030270 A1 | 1/2013 | Chiou et al. |
| 2013/0032713 A1 | 2/2013 | Barbi et al. |
| 2013/0090541 A1 | 4/2013 | MacFarlane et al. |
| 2013/0144644 A1 | 6/2013 | Simpson |
| 2013/0221221 A1 | 8/2013 | Bouzid et al. |
| 2013/0225953 A1 | 8/2013 | Oliviero et al. |
| 2013/0342835 A1 | 12/2013 | Blacksberg |
| 2014/0027607 A1 | 1/2014 | Mordarski et al. |
| 2014/0028211 A1* | 1/2014 | Imam ................ H02M 3/33507 315/200 R |
| 2014/0055181 A1* | 2/2014 | Chaivipas ............. H03L 7/0812 327/156 |
| 2014/0066783 A1 | 3/2014 | Kiani |
| 2014/0171757 A1 | 6/2014 | Kawato et al. |
| 2014/0185643 A1 | 7/2014 | McComb et al. |
| 2014/0191115 A1 | 7/2014 | Webster et al. |
| 2014/0211194 A1 | 7/2014 | Pacala et al. |
| 2014/0217264 A1 | 8/2014 | Shepard |
| 2014/0275891 A1 | 9/2014 | Muehlemann et al. |
| 2014/0289001 A1 | 9/2014 | Shelton |
| 2014/0291481 A1 | 10/2014 | Zhang et al. |
| 2015/0038811 A1 | 2/2015 | Asaka |
| 2015/0038812 A1 | 2/2015 | Ayaz et al. |
| 2015/0041625 A1 | 2/2015 | Dutton |
| 2015/0041627 A1 | 2/2015 | Webster |
| 2015/0054111 A1 | 2/2015 | Niclass et al. |
| 2015/0057511 A1 | 2/2015 | Basu |
| 2015/0077279 A1 | 3/2015 | Song |
| 2015/0094552 A1 | 4/2015 | Golda |
| 2015/0150505 A1 | 6/2015 | Kaskoun et al. |
| 2015/0157262 A1 | 6/2015 | Schuessler |
| 2015/0157435 A1 | 6/2015 | Chasins et al. |
| 2015/0182136 A1 | 7/2015 | Durduran et al. |
| 2015/0192677 A1 | 7/2015 | Yu et al. |
| 2015/0200222 A1 | 7/2015 | Webster |
| 2015/0293224 A1 | 10/2015 | Eldada et al. |
| 2015/0327777 A1 | 11/2015 | Kostic et al. |
| 2015/0333095 A1 | 11/2015 | Fallica et al. |
| 2015/0364635 A1 | 12/2015 | Bodlovic et al. |
| 2016/0049765 A1 | 2/2016 | Eldada |
| 2016/0099371 A1 | 4/2016 | Webster |
| 2016/0119983 A1 | 4/2016 | Moore |
| 2016/0150963 A1 | 6/2016 | Roukes et al. |
| 2016/0161600 A1 | 6/2016 | Eldada et al. |
| 2016/0181302 A1 | 6/2016 | McGarvey et al. |
| 2016/0182902 A1 | 6/2016 | Guo |
| 2016/0218236 A1 | 7/2016 | Dhulla et al. |
| 2016/0247301 A1 | 8/2016 | Fang |
| 2016/0278715 A1 | 9/2016 | Yu et al. |
| 2016/0287107 A1 | 10/2016 | Szabados |
| 2016/0296168 A1 | 10/2016 | Abreu |
| 2016/0341656 A1 | 11/2016 | Liu et al. |
| 2016/0345880 A1 | 12/2016 | Nakaji et al. |
| 2016/0356718 A1 | 12/2016 | Yoon et al. |
| 2016/0357260 A1 | 12/2016 | Raynor et al. |
| 2017/0030769 A1 | 2/2017 | Clemens et al. |
| 2017/0047372 A1 | 2/2017 | McGarvey et al. |
| 2017/0052065 A1 | 2/2017 | Sharma et al. |
| 2017/0085547 A1 | 3/2017 | De Aguiar et al. |
| 2017/0118423 A1 | 4/2017 | Zhou et al. |
| 2017/0124713 A1 | 5/2017 | Jurgenson et al. |
| 2017/0131143 A1 | 5/2017 | Andreou et al. |
| 2017/0139041 A1 | 5/2017 | Drader et al. |
| 2017/0141100 A1 | 5/2017 | Tseng et al. |
| 2017/0164857 A1* | 6/2017 | Soulet De Brugiere .................... A61B 5/6814 |
| 2017/0176579 A1 | 6/2017 | Niclass et al. |
| 2017/0176596 A1 | 6/2017 | Shpunt |
| 2017/0179173 A1 | 6/2017 | Mandai et al. |
| 2017/0186798 A1 | 6/2017 | Yang et al. |
| 2017/0202518 A1 | 7/2017 | Furman et al. |
| 2017/0265822 A1 | 9/2017 | Du |
| 2017/0276545 A1 | 9/2017 | Henriksson |
| 2017/0281086 A1 | 10/2017 | Donaldson |
| 2017/0299700 A1 | 10/2017 | Pacala et al. |
| 2017/0303789 A1 | 10/2017 | Tichauer et al. |
| 2017/0314989 A1 | 11/2017 | Mazzillo et al. |
| 2017/0363467 A1 | 12/2017 | Clemens et al. |
| 2017/0367650 A1 | 12/2017 | Wallois |
| 2018/0003821 A1 | 1/2018 | Imai |
| 2018/0014741 A1 | 1/2018 | Chou |
| 2018/0019268 A1 | 1/2018 | Zhang et al. |
| 2018/0020960 A1 | 1/2018 | Sarussi |
| 2018/0026147 A1 | 1/2018 | Zhang et al. |
| 2018/0027196 A1 | 1/2018 | Yang et al. |
| 2018/0033895 A1 | 2/2018 | Mazzillo et al. |
| 2018/0039053 A1 | 2/2018 | Kremer et al. |
| 2018/0045816 A1 | 2/2018 | Jarosinski et al. |
| 2018/0062345 A1 | 3/2018 | Bills et al. |
| 2018/0066986 A1 | 3/2018 | Kasai et al. |
| 2018/0069043 A1 | 3/2018 | Pan et al. |
| 2018/0070830 A1 | 3/2018 | Sutin et al. |
| 2018/0070831 A1 | 3/2018 | Sutin et al. |
| 2018/0081061 A1 | 3/2018 | Mandai et al. |
| 2018/0089531 A1 | 3/2018 | Geva et al. |
| 2018/0089848 A1 | 3/2018 | Yang et al. |
| 2018/0090526 A1 | 3/2018 | Mandai et al. |
| 2018/0090536 A1 | 3/2018 | Mandai et al. |
| 2018/0102442 A1 | 4/2018 | Wang et al. |
| 2018/0103528 A1 | 4/2018 | Moore |
| 2018/0103861 A1 | 4/2018 | Sutin et al. |
| 2018/0117331 A1* | 5/2018 | Kuzniecky .......... A61N 1/36064 |
| 2018/0120152 A1 | 5/2018 | Leonardo |
| 2018/0122560 A1 | 5/2018 | Okuda |
| 2018/0156660 A1 | 6/2018 | Turgeon |
| 2018/0167606 A1 | 6/2018 | Cazaux et al. |
| 2018/0175230 A1 | 6/2018 | Droz et al. |
| 2018/0180473 A1 | 6/2018 | Clemens et al. |
| 2018/0185667 A1 | 7/2018 | Huang |
| 2018/0217261 A1 | 8/2018 | Wang |
| 2018/0296094 A1 | 10/2018 | Nakamura |
| 2018/0366342 A1 | 12/2018 | Inoue et al. |
| 2019/0006399 A1 | 1/2019 | Otake et al. |
| 2019/0026849 A1 | 1/2019 | Demeyer |
| 2019/0088697 A1 | 3/2019 | Furukawa et al. |
| 2019/0091483 A1 | 3/2019 | Deckert |
| 2019/0113385 A1 | 4/2019 | Fukuchi |
| 2019/0120975 A1 | 4/2019 | Ouvrier-Buffet |
| 2019/0167211 A1 | 6/2019 | Everman et al. |
| 2019/0175068 A1 | 6/2019 | Everdell |
| 2019/0200888 A1 | 7/2019 | Poltorak |
| 2019/0209012 A1 | 7/2019 | Yoshimoto et al. |
| 2019/0261869 A1 | 8/2019 | Franceschini |
| 2019/0298158 A1 | 10/2019 | Dhaliwal |
| 2019/0343395 A1 | 11/2019 | Cussac |
| 2019/0355773 A1 | 11/2019 | Field et al. |
| 2019/0355861 A1 | 11/2019 | Katnani |

(56) References Cited

U.S. PATENT DOCUMENTS

| | | | |
|---|---|---|---|
| 2019/0363210 A1 | 11/2019 | Do Valle | |
| 2019/0378869 A1 | 12/2019 | Field et al. | |
| 2019/0388018 A1 | 12/2019 | Horstmeyer | |
| 2019/0391213 A1 | 12/2019 | Alford | |
| 2020/0022581 A1 | 1/2020 | Vanegas | |
| 2020/0044098 A1 | 2/2020 | Azuma | |
| 2020/0056263 A1 | 2/2020 | Bhattacharyya | |
| 2020/0057115 A1 | 2/2020 | Jiménez-Martínez | |
| 2020/0057116 A1 | 2/2020 | Zorzos et al. | |
| 2020/0060542 A1 | 2/2020 | Alford | |
| 2020/0088811 A1 | 3/2020 | Mohseni | |
| 2020/0109481 A1 | 4/2020 | Sobek | |
| 2020/0123416 A1 | 4/2020 | Bhattacharyya | |
| 2020/0136632 A1* | 4/2020 | Lin | H03M 1/1009 |
| 2020/0182692 A1 | 6/2020 | Lilic | |
| 2020/0188030 A1 | 6/2020 | Kopper et al. | |
| 2020/0191883 A1 | 6/2020 | Bhattacharyya | |
| 2020/0196932 A1 | 6/2020 | Johnson et al. | |
| 2020/0241094 A1 | 7/2020 | Alford | |
| 2020/0253479 A1 | 8/2020 | Nurmikko | |
| 2020/0256929 A1 | 8/2020 | Ledbetter et al. | |
| 2020/0309873 A1 | 10/2020 | Ledbetter et al. | |
| 2020/0315510 A1 | 10/2020 | Johnson | |
| 2020/0334559 A1 | 10/2020 | Anderson | |
| 2020/0337624 A1 | 10/2020 | Johnson | |
| 2020/0341081 A1 | 10/2020 | Mohseni et al. | |
| 2020/0348368 A1 | 11/2020 | Garber et al. | |
| 2020/0381128 A1 | 12/2020 | Pratt | |
| 2020/0390358 A1 | 12/2020 | Johnson | |
| 2020/0393902 A1 | 12/2020 | Mann et al. | |
| 2020/0400763 A1 | 12/2020 | Pratt | |
| 2021/0015385 A1 | 1/2021 | Katnani | |
| 2021/0011094 A1 | 2/2021 | Bednarke | |
| 2021/0041512 A1 | 2/2021 | Pratt | |
| 2021/0063510 A1 | 3/2021 | Ledbetter | |
| 2021/0013974 A1 | 5/2021 | Seidman | |
| 2021/0139742 A1 | 5/2021 | Seidman | |
| 2021/0265512 A1 | 8/2021 | Ayel | |

FOREIGN PATENT DOCUMENTS

| | | |
|---|---|---|
| EP | 0656536 | 4/2004 |
| EP | 2294973 | 3/2011 |
| EP | 3419168 | 12/2018 |
| EP | 3487072 | 5/2019 |
| KR | 20170087639 A | 7/2017 |
| WO | 8804034 | 6/1988 |
| WO | 1999053577 | 10/1999 |
| WO | 2008144831 | 12/2008 |
| WO | 2011083563 | 7/2011 |
| WO | 2012135068 | 10/2012 |
| WO | 2013034770 | 3/2013 |
| WO | 2013066959 | 5/2013 |
| WO | 2015052523 | 4/2015 |
| WO | 2015109005 | 7/2015 |
| WO | 2016166002 | 10/2016 |
| WO | 2017004663 | 1/2017 |
| WO | 2017083826 | 5/2017 |
| WO | 2017130682 | 8/2017 |
| WO | 2017150146 | 9/2017 |
| WO | 2017203936 | 11/2017 |
| WO | 2018007829 | 1/2018 |
| WO | 2018033751 | 2/2018 |
| WO | 2018122560 | 7/2018 |
| WO | 2019221784 | 11/2019 |

OTHER PUBLICATIONS

Gallivanoni, et al.,"Progress in Quenching Circuits for Single Photon Avalanche Diodes," IEEE Transactions on Nuclear Science, vol. 57, No. 6, Dec. 2010.

Gnecchi, et al.,"A 1×16 SiPM Array for Automotive 3D Imaging LIDAR Systems."

Harmon, et al.,"Compound Semiconductor SPAD Arrays," LightSpin Technologies, http://www.lightspintech.com/publications.html.

Henderson, et al.,"A 192×128 Time Correlated SPAD Image Sensor in 40-nm CMOS Technology," IEEE Journal of Solid-State Circuits, 2019.

Henderson, et al.,"A 256×256 40nm/90nm CMOS 3D-Stacked 120dB Dynamic-Range Reconfigurable Time-Resolved SPAD Imager," 2019 IEEE International Solid-State Circuits Conference— (ISSCC), San Francisco, CA, USA, 2019, pp. 106-108. doi: 10.1109/ISSCC.2019.8662355.

Huppert, et al.,"HomER: a review of time-series analysis methods for near-infrared spectroscopy of the brain," Appl. Opt. 48(10), D280 (2009).

Kienle, et al.,"Improved solutions of the steady-state and the time-resolved diffusion equations for reflectance from a semi-infinite turbid medium," J. Opt. Soc. Am. A 14(1), 246 (1997).

Konugolu, et al.,"Broadband (600-1350 nm) Time-Resolved Diffuse Optical Spectrometer for Clinical Use," IEEE Journal of Selected Topics in Quantum Electronics, vol. 22, No. 3, May/Jun. 2016.

Lacerenza, et al.,"Wearable and wireless time-domain near-infrared spectroscopy system for brain and muscle hemodynamic monitoring," Biomed. Opt. Express 11(10), 5934 (2020).

Lange, et al.,"Clinical Brain Monitoring with Time Domain NIRS: A Review and Future Perspectives," Applied Sciences 9(8), 1612 (2019).

Lange, et al., MAESTROS: A Multiwavelength Time-Domain NIRS System to Monitor Changes in Oxygenation and Oxidation State of Cytochrome-C-Oxidase, IEEE J. Select. Topics Quantum Electron. 25(1), 1-12 (2019).

Lee, et al.,"High-Performance Back-Illuminated Three-Dimensional Stacked Single-Photon Avalanche Diode Implemented in 45-nm CMOS Technology," IEEE Journal of Selected Topics in Quantum Electronics 6, 1-9 (2018).

Mandai, et al.,"A 4×4×416 digital SiPM array with 192 TDCs for multiple high-resolution timestamp acquisition," 2013 JINST 8 PO5024.

Martelli, et al.,"Optimal estimation reconstruction of the optical properties of a two-layered tissue phantom from time-resolved single-distance measurements," Journal of Biomedical Optics 20(11), 115001 (Nov. 2015).

Maruyama, et al.,"A 1024×8, 700-ps Time-Gated SPAD Line Sensor for Planetary Surface Exploration With Laser Raman Spectroscopy and LIBS," IEEE Journal of Solid-State Circuits, vol. 49, No. 1, Jan. 2014.

Mita, et al.,"High-Speed and Compact Quenching Circuit for Single-Photon Avalanche Diodes," IEEE Transactions on Instrumentation and Measurement, vol. 57, No. 3, Mar. 2008. pp. 543-547.

Mora, et al.,"Fast silicon photomultiplier improves signal harvesting and reduces complexity in time-domain diffuse optics," Opt. Express 23(11), 13937 (2015).

Mora, et al.,"Fast-Gated Single-Photon Avalanche Diode for Wide Dynamic Range Near Infrared Spectroscopy," IEEE Journal of Selected Topics in Quantum Electronics, vol. 16, No. 4, pp. 1023-1030, Jul./Aug. 2010.

Parmesan, et al.,"A 256×256 SPAD array with in-pixel Time to Amplitude Conversion for Fluorescence Lifetime Imaging Microscopy," 2015.

Pifferi, et al.,"Performance assessment of photon migration instruments: the MEDPHOT protocol," Applied Optics, 44(11), 2104-2114.

Prahl, et al.,"Optical Absorption of Hemoglobin," http://omlc.ogi.edu/spectra/hemoglobin/index.html.

Puszka, et al.,"Time-resolved diffuse optical tomography using fast-gated single-photon avalanche diodes," Biomedical optics express, 2013, vol. 4, No. 8, pp. 1351-1365 (Year: 2013).

Re, et al.,"Multi-channel medical device for time domain functional near infrared spectroscopy based on wavelength space multiplexing," Biomed. Opt. Express 4(10), 2231 (2013).

Renna, et al.,"Eight-Wavelength, Dual Detection Channel Instrument for Near-Infrared Time-Resolved Diffuse Optical Spectroscopy," IEEE J. Select. Topics Quantum Electron. 25(1), 1-11 (2019).

(56) References Cited

OTHER PUBLICATIONS

Richardson, et al.,"A 32×32 50ps resolution 10 bit time to digital converter array in 130nm CMOS for time correlated imaging," CICC 2009 Proceedings of the IEEE 2009 Custom Integrated Circuits Conference. IEEE Society, San Jose, U.S.A., pp. 77-80, CICC 2009, San Jose, U.S.A., Sep. 13, 2009. https://doi.org/doi:10.1109/CICC.2009.5280890.
Takai, et al.,"Single-Photon Avalanche Diode with Enhanced NIR-Sensitivity for Automotive LIDAR Systems," Sensors, 2016, 16(4): 459, pp. 1-9 (Year: 2016).
Torricelli, et al.,"Time domain functional NIRS imaging for human brain mapping," NeuroImage 85, 28-50 (2014).
Wabnitz, et al.,"Depth-selective data analysis for time-domain fNIRS: moments vs. time windows," Biomed. Opt. Express 11(8), 4224 (2020).
Wabnitz, et al.,"Performance assessment of time-domain optical brain imagers, part 1: basic instrumental performance protocol," Journal of Biomedical Optics 19(8), 086010 (Aug. 2014).
Wabnitz, et al.,"Performance assessment of time-domain optical brain imagers, part 2: nEUROPt protocol," Journal of Biomedical Optics 19(8), 086012 (Aug. 2014).
Wojtkiewicz, et al.,"Self-calibrating time-resolved near infrared spectroscopy," Biomed. Opt. Express 10(5), 2657 (2019).
Zhang, et al.,"A CMOS SPAD Imager with Collision Detection and 128 Dynamically Reallocating TDCs for Single-Photon Counting and 3D Time-of-Flight Imaging," Sensors (Basel, Switzerland), 18(11), 4016. doi:10.3390/s18114016.
"emojipedia.org", https://emojipedia.org (accessed May 27, 2021).
"International Search Report and Written Opinion received in International Application No. PCT/2021/018188".
"International Search Report and Written Opinion received in International Application No. PCT/US2021/018155".
"International Search Report and Written Opinion received in International Application No. PCT/US2021/018187".
"International Search Report and Written Opinion received in International Application No. PCT/US2021/018190".
"scienceofpeople.com/emojis", https://www.scienceofpeople.com/emojis/ (accessed May 27, 2021).
Hebert, et al.,"Spatiotemporal image correlation spectroscopy (STICS) theory, verification, and application to protein velocity mapping in living CHO cells", Biophysical journal 88, No. 5 (2005): 3601-3614.
Kheng, et al.,"Image Processing", https://www.comp.nus.edu.sg/~cs4243/lecture/imageproc.pdf, Mar. 9, 2014.
Sneha, et al.,"Understanding Correlation", https://www.allaboutcircuits.com/technical-articles/understanding-correlation/, Jan. 4, 2017.
Xu, et al.,"A 655 µW Silicon Photomultiplier-Based NIRS/EEG/EIT Monitoring ASIC for Wearable Functional Brain Imaging", IEEE Transactions on Biomedical Circuits and Systems, IEEE, US, vol. 12, No. 6, Dec. 1, 2018.
Zucconi, et al.,"The Autocorrelation Function", https://www.alanzucconi.com/2016/06/06/autocorrelation-function/, Jun. 6, 2016.
"International Search Report and Written Opinion received in International Application No. PCT/US2021/022486".
Chen, et al., "A PVT Insensitive Field Programmable Gate Array Time-to-digital Converter", 2013 IEEE Nordic-Mediterranean Workshop on Time-To-Digital Converters. Oct. 3, 2013.
Field, et al., "A 100-fps, Time-Correlated Single-PhotonCounting-Based Fluorescence-Lifetime Imager in 130-nm CMOS", IEEE Journal of Solid-State Circuits, vol. 49, No. 4, Apr. 2014.
Lebid, et al., "Multi-Timescale Measurements of Brain Responses in Visual Cortex During Functional Stimulation Using Time-Resolved Spectroscopy", SPIE vol. 5826. Dec. 31, 2005. p. 609, last paragraph—p. 610, paragraph 1.
Zheng, et al., "An Integrated Bias Voltage Control Method for SPAD Arrays", Oct. 1, 2018, IEEE Service Center.
Alayed, et al.,"Characterization of a Time-Resolved Diffuse Optical Spectroscopy Prototype Using Low-Cost, Compact Single Photon Avalanche Detectors for Tissue Optics Applications," Sensors 2018, 18, 3680; doi:10.3390/s18113680.

Bellis, et al.,"Photon counting imaging: the DigitalAPD," Society of Photo-Optical Instrumentation Engineers (SPIE) Conference Series, Feb. 2006, vol. 6068, pp. 111-120.
Blutman, et al.,"A 0.1 pJ Freeze Vernier Time-to-Digital Converter in 65nm CMOS," 2014 International Symposium on Circuits and Systems (ISCAS), Melbourne, Australia.
Cambie, et al.,"Every photon counts: understanding and optimizing photon paths in luminescent solar concentrator-based photomicroreactors (LSC-PMs)," React. Chem. Eng., 2017, 2, 561-566.
Contini, et al.,"Photon migration through a turbid slab described by a model based on diffusion approximation. I. Theory," Appl. Opt. 36(19), 4587 (1997).
Dalla Mora, et al.,"Fast-Gated Single-Photon Avalanche Diode for Wide Dynamic Range Near Infrared Spectroscopy," IEEE Journal of Selected Topics in Quantum Electronics, vol. 16, No. 4, Jul./Aug. 2010.
Dalla Mora, et al.,"Memory effect in silicon time-gated single-photon avalanche diodes," http://dx.doi.org/10.1063/1.4915332, Journal of Applied Physics 117, 114501, 2015.
De Heyn, et al.,"A fast start-up 3GHz-10GHz digitally controlled oscillator for UWB impulse radio in 90nm CMOS," 2007 European Solid-State Circuits Conference—(ESSCIRC), Munich, Germany, pp. 484-487.
Di Sieno, et al.,"Probe-hosted large area silicon photomultiplier and high-throughput timing electronics for enhanced performance time-domain functional near-infrared spectroscopy," Biomed. Opt. Express 11(11), 6389 (2020).
Dutton, et al.,"A Time-Correlated Single-Photon-Counting Sensor with 14GS/s Histogramming Time-to-Digital Converter," 2015 IEEE International Solid-State Circuits Conference ISSCC 2015 / Session 11 / Sensors and Imagers for Life Sciences / 11.5.
Fishburn, et al.,"Temporal Derivative Distribution Repair (TDDR): A motion correction method for fNIRS," Neuroimage, Jan. 1, 2019; 184: 171-179. doi:10.1016/j.neuroimage.2018.09.025.
Zucchelli, et al.,"Method for the discrimination of superficial and deep absorption variations by time domain fNIRS," 2013 OSA Dec. 1, 2013 | vol. 4, No. 12 | DOI:10.1364/BOE.4.002893 | Biomedical Optics Express 2893.
International Search Report and Written Opinion received in International Application No. PCT/2020/027537, dated Sep. 7, 2020.
International Search Report and Written Opinion received in International Application No. PCT/2020/028820, dated Aug. 26, 2020.
International Search Report and Written Opinion received in International Application No. PCT/US20/34062, dated Aug. 26, 2020.
International Search Report and Written Opinion received in International Application No. PCT/US2018/058580, dated Feb. 12, 2019.
International Search Report and Written Opinion received in International Application No. PCT/US2018/062777, dated Feb. 13, 2019.
International Search Report and Written Opinion received in International Application No. PCT/US2019/019317, dated May 28, 2019.
Non-Final Office Action received in U.S. Appl. No. 16/177,351, dated Apr. 1, 2019.
Non-Final Office Action received in U.S. Appl. No. 16/283,730, dated May 16, 2019.
Non-Final Office Action received in U.S. Appl. No. 16/370,991, dated Feb. 10, 2020.
Non-Final Office Action received in U.S. Appl. No. 16/544,850, dated Feb. 25, 2020.
Non-Final Office Action received in U.S. Appl. No. 16/544,850, dated Jun. 25, 2020.
Non-Final Office Action received in U.S. Appl. No. 16/856,524, dated Dec. 1, 2020.
Partial Search Report received in International Application No. PCT/2020/028820, dated Jul. 1, 2020.
Partial Search Report received in International Application No. PCT/US2020/027537, dated Jul. 17, 2020.

* cited by examiner

TEMPORAL RESOLUTION CONTROL FOR TEMPORAL POINT SPREAD FUNCTION GENERATION IN AN OPTICAL MEASUREMENT SYSTEM

RELATED APPLICATIONS

The present application claims priority under 35 U.S.C. § 119(e) to U.S. Provisional Patent Application No. 62/992,506, filed on Mar. 20, 2020, and to U.S. Provisional Patent Application No. 63/027,025, filed on May 19, 2020. These applications are incorporated herein by reference in their respective entireties.

BACKGROUND INFORMATION

Detecting neural activity in the brain (or any other turbid medium) is useful for medical diagnostics, imaging, neuro-engineering, brain-computer interfacing, and a variety of other diagnostic and consumer-related applications. For example, it may be desirable to detect neural activity in the brain of a user to determine if a particular region of the brain has been impacted by reduced blood irrigation, a hemorrhage, or any other type of damage. As another example, it may be desirable to detect neural activity in the brain of a user and computationally decode the detected neural activity into commands that can be used to control various types of consumer electronics (e.g., by controlling a cursor on a computer screen, changing channels on a television, turning lights on, etc.).

Neural activity and other attributes of the brain may be determined or inferred by measuring responses of tissue within the brain to light pulses. One technique to measure such responses is time-correlated single-photon counting (TCSPC). Time-correlated single-photon counting detects single photons and measures a time of arrival of the photons with respect to a reference signal (e.g., a light source). By repeating the light pulses, TCSPC may accumulate a sufficient number of photon events to statistically determine a histogram representing the distribution of detected photons. Based on the histogram of photon distribution, the response of tissue to light pulses may be determined to determine neural activity and/or other attributes of the brain.

A photodetector capable of detecting a single photon (i.e., a single particle of optical energy) is an example of a non-invasive detector that can be used in an optical measurement system to detect neural activity within the brain. An exemplary photodetector is implemented by a semiconductor-based single-photon avalanche diode (SPAD), which is capable of capturing individual photons with very high time-of-arrival resolution (a few tens of picoseconds).

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Systems, circuits, and methods for controlling a temporal resolution of a temporal point spread function (TPSF) in an optical measurement system are described herein.

For example, an exemplary system may include a photodetector configured to generate a plurality of photodetector output pulses over time as a plurality of light pulses are applied to and scattered by a target of interest, e.g., brain tissue. Each photodetector output pulse is generated when the photodetector detects a photon from one of the light pulses that is scattered by the target. The system may further include a TPSF generation circuit configured to generate, based on the photodetector output pulses, a TPSF representative of a light pulse response of the target. The system may further include a control circuit communicatively coupled to the TPSF generation circuit and configured to direct the TPSF generation circuit to selectively operate in different resolution modes. For example, the control circuit may direct the TPSF generation circuit to selectively operate in a first resolution mode in which a temporal resolution of the TPSF is a first temporal resolution value or in a second resolution mode in which the temporal resolution of the TPSF is a second temporal resolution value different than the first temporal resolution value.

The systems, circuits, and methods described herein provide various benefits and advantages. For example, the systems, circuits, and methods described herein may conserve power, minimize data transmission bandwidth requirements, and reduce data processing requirements associated with generating and processing TPSFs. These and other benefits and advantages of the present systems, circuits, and methods described herein are described more fully herein.

Figure 1:
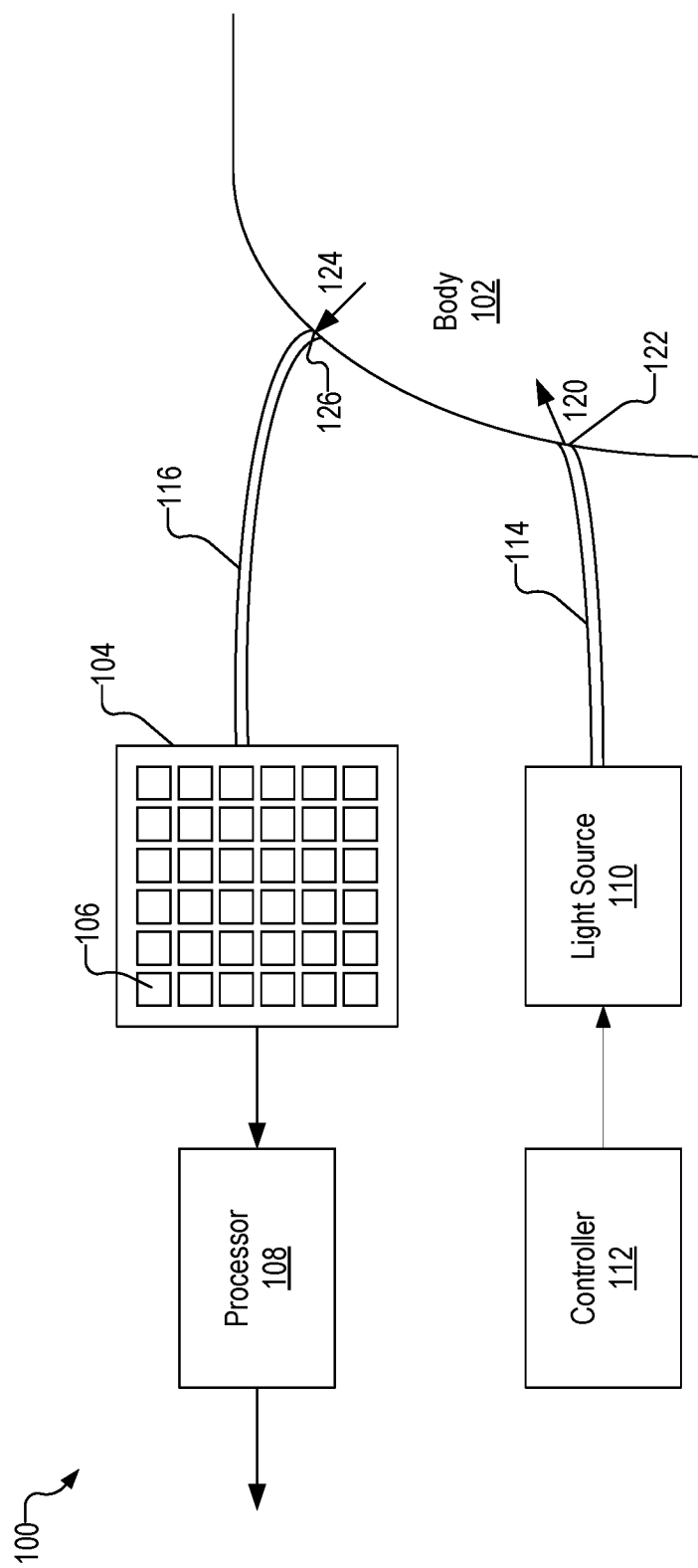
FIG. 1 shows an exemplary optical measurement system.

FIG. 1 shows an exemplary optical measurement system 100 configured to perform an optical measurement operation with respect to a body 102. Optical measurement system 100 may, in some examples, be portable and/or wearable by a user. Optical measurement systems that may be used in connection with the embodiments described herein are described more fully in U.S. patent application Ser. No. 17/176,315, filed Feb. 16, 2021; U.S. patent application Ser. No. 17/176,309, filed Feb. 16, 2021; U.S. patent application Ser. No. 17/176,460, filed Feb. 16, 2021; U.S. patent application Ser. No. 17/176,470, filed Feb. 16, 2021; U.S. patent application Ser. No. 17/176,487, filed Feb. 16, 2021; U.S. patent application Ser. No. 17/176,539, filed Feb. 16, 2021; U.S. patent application Ser. No. 17/176,560, filed Feb. 16, 2021; and U.S. patent application Ser. No. 17/176,466, filed Feb. 16, 2021, which applications are incorporated herein by reference in their entirety.

In some examples, optical measurement operations performed by optical measurement system 100 are associated with a time domain-based optical measurement technique. Example time domain-based optical measurement techniques include, but are not limited to, TCSPC, time domain near infrared spectroscopy (TD-NIRS), time domain diffusive correlation spectroscopy (TD-DCS), and time domain Digital Optical Tomography (TD-DOT).

As shown, optical measurement system 100 includes a detector 104 that includes a plurality of individual photodetectors (e.g., photodetector 106), a processor 108 coupled to detector 104, a light source 110, a controller 112, and optical conduits 114 and 116 (e.g., light pipes). However, one or more of these components may not, in certain embodiments, be considered to be a part of optical measurement system 100. For example, in implementations where optical measurement system 100 is wearable by a user, processor 108 and/or controller 112 may in some embodiments be separate from optical measurement system 100 and not configured to be worn by the user.

Detector 104 may include any number of photodetectors 106 as may serve a particular implementation, such as $2^n$ photodetectors (e.g., 256, 512, . . . , 16384, etc.), where n is an integer greater than or equal to one (e.g., 4, 5, 8, 10, 11, 14, etc.). Photodetectors 106 may be arranged in any suitable manner.

Photodetectors 106 may each be implemented by any suitable circuit configured to detect individual photons of light incident upon photodetectors 106. For example, each photodetector 106 may be implemented by a single photon avalanche diode (SPAD) circuit and/or other circuitry as may serve a particular implementation.

Processor 108 may be implemented by one or more physical processing (e.g., computing) devices. In some examples, processor 108 may execute instructions (e.g., software) configured to perform one or more of the operations described herein.

Light source 110 may be implemented by any suitable component configured to generate and emit light. For example, light source 110 may be implemented by one or more laser diodes. In some examples, the light emitted by light source 110 is high coherence light (e.g., light that has a coherence length of at least 5 centimeters) at a predetermined center wavelength.

Light source 110 is controlled by controller 112, which may be implemented by any suitable computing device (e.g., processor 108), integrated circuit, and/or combination of hardware and/or software as may serve a particular implementation. In some examples, controller 112 is configured to control light source 110 by turning light source 110 on and off and/or setting an intensity of light generated by light source 110. Controller 112 may be manually operated by a user, or may be programmed to control light source 110 automatically.

Light emitted by light source 110 may travel via an optical conduit 114 (e.g., a light pipe, a light guide, a waveguide, a single-mode optical fiber, and/or or a multi-mode optical fiber) to body 102 of a subject. In cases where optical conduit 114 is implemented by a light guide, the light guide may be spring loaded and/or have a cantilever mechanism to allow for conformably pressing the light guide firmly against body 102.

Body 102 may include any suitable turbid medium. For example, in some implementations, body 102 is a head or any other body part of a human or other animal. Alternatively, body 102 may be a non-living object. For illustrative purposes, it will be assumed in the examples provided herein that body 102 is a human head.

As indicated by arrow 120, the light emitted by light source 110 enters body 102 at a first location 122 on body 102. To this end, a distal end of optical conduit 114 may be positioned at (e.g., right above or physically attached to) first location 122 (e.g., to a scalp of the subject). In some examples, the light may emerge from optical conduit 114 and spread out to a certain spot size on body 102 to fall under a predetermined safety limit.

As shown, a proximal end of optical conduit 116 (e.g., a light pipe, a single-mode optical fiber, and/or or a multi-mode optical fiber) is positioned at (e.g., right above or physically attached to) output location 126 on body 102. In this manner, optical conduit 116 may collect light 124 as it exits body 102 at location 126 and carry the light to detector 104. The light may pass through one or more lenses and/or other optical elements (not shown) that direct the light onto each of the photodetectors 106 included in detector 104.

Photodetectors 106 may be connected in parallel in detector 104. An output of each of photodetectors 106 may be accumulated to generate an accumulated output of detector 104. Processor 108 may receive the accumulated output and determine, based on the accumulated output, a temporal distribution of photons detected by photodetectors 106. Processor 108 may then generate, based on the temporal distribution, a histogram representing a light pulse response of a target (e.g., brain tissue, blood flow, etc.) in body 102. Example embodiments of accumulated outputs are described herein.

Figure 2:
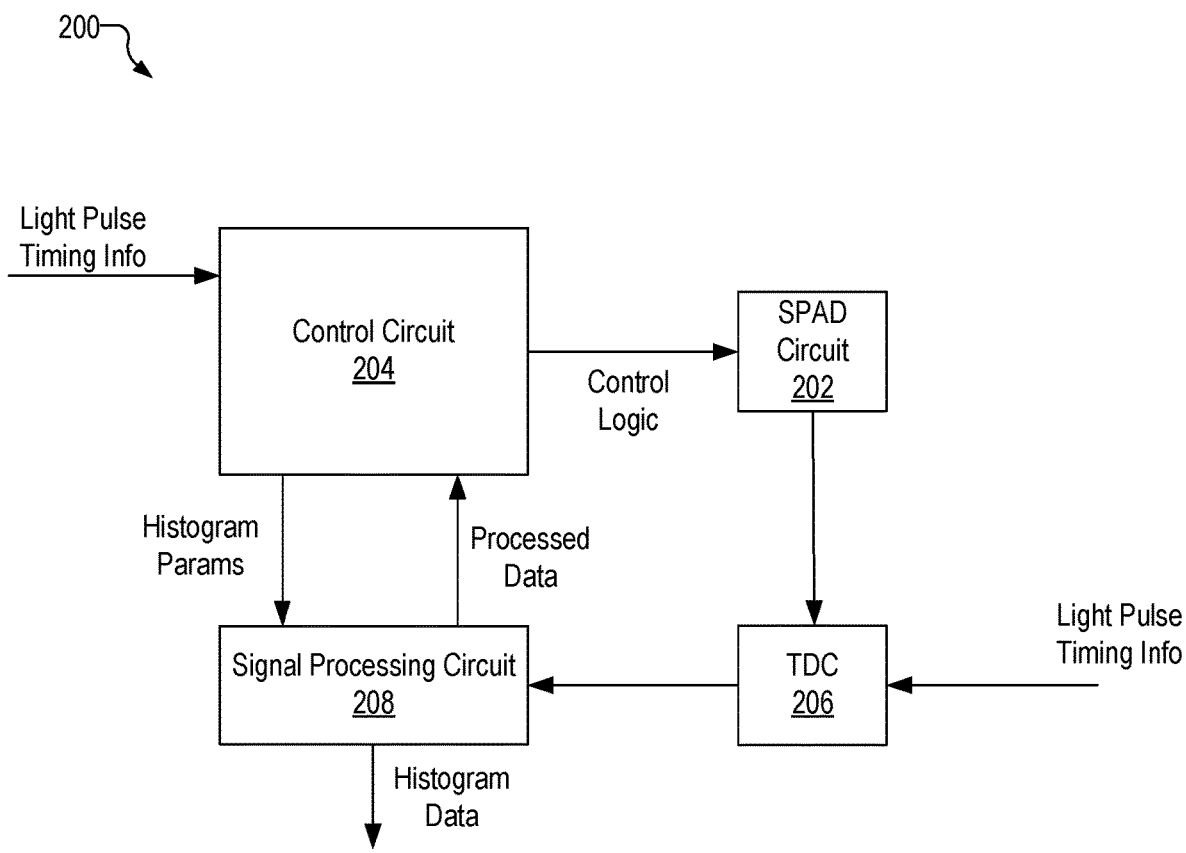
FIG. 2 illustrates an exemplary detector architecture.

FIG. 2 illustrates an exemplary detector architecture 200 that may be used in accordance with the systems and methods described herein. As shown, architecture 200 includes a SPAD circuit 202 that implements photodetector 106, a control circuit 204, a time-to-digital converter (TDC) 206, and a signal processing circuit 208. Architecture 200 may include additional or alternative components as may serve a particular implementation.

In some examples, SPAD circuit 202 includes a SPAD and a fast gating circuit configured to operate together to detect a photon incident upon the SPAD. As described herein, SPAD circuit 202 may generate an output when SPAD circuit 202 detects a photon.

The fast gating circuit included in SPAD circuit 202 may be implemented in any suitable manner. For example, the fast gating circuit may include a capacitor that is pre-charged with a bias voltage before a command is provided to arm the SPAD. Gating the SPAD with a capacitor instead of with an active voltage source, such as is done in some conventional SPAD architectures, has a number of advantages and benefits. For example, a SPAD that is gated with a capacitor may be armed practically instantaneously compared to a SPAD that is gated with an active voltage source. This is because the capacitor is already charged with the bias voltage when a command is provided to arm the SPAD. This is described more fully in U.S. Pat. Nos. 10,158,038 and 10,424,683, incorporated herein by reference in their respective entireties.

In some alternative configurations, SPAD circuit 202 does not include a fast gating circuit. In these configurations, the SPAD included in SPAD circuit 202 may be gated in any suitable manner or be configured to operate in a free running mode with passive quenching.

Control circuit 204 may be implemented by an application specific integrated circuit (ASIC) or any other suitable circuit configured to control an operation of various components within SPAD circuit 202. For example, control circuit 204 may output control logic that puts the SPAD included in SPAD circuit 202 in either an armed or a disarmed state.

In some examples, control circuit 204 may control a gate delay, which specifies a predetermined amount of time control circuit 204 is to wait after an occurrence of a light pulse (e.g., a laser pulse) to put the SPAD in the armed state. To this end, control circuit 204 may receive light pulse timing information, which indicates a time at which a light pulse occurs (e.g., a time at which the light pulse is applied to body 102). Control circuit 204 may also control a programmable gate width, which specifies how long the SPAD is kept in the armed state before being disarmed.

Control circuit 204 is further configured to control signal processing circuit 208. For example, control circuit 204 may provide histogram parameters (e.g., time bins, number of light pulses, type of histogram, etc.) to signal processing circuit 208. Signal processing circuit 208 may generate histogram data in accordance with the histogram parameters. In some examples, control circuit 204 is at least partially implemented by controller 112.

TDC 206 is configured to measure a time difference between an occurrence of an output pulse generated by SPAD circuit 202 and an occurrence of a light pulse. To this end, TDC 206 may also receive the same light pulse timing information that control circuit 204 receives. TDC 206 may be implemented by any suitable circuitry as may serve a particular implementation.

Signal processing circuit 208 is configured to perform one or more signal processing operations on data output by TDC 206. For example, signal processing circuit 208 may generate histogram data based on the data output by TDC 206 and in accordance with histogram parameters provided by control circuit 204. To illustrate, signal processing circuit 208 may generate, store, transmit, compress, analyze, decode, and/or otherwise process histograms based on the data output by TDC 206. In some examples, signal processing circuit 208 may provide processed data to control circuit 204, which may use the processed data in any suitable manner. In some examples, signal processing circuit 208 is at least partially implemented by processor 108.

In some examples, each photodetector 106 (e.g., SPAD circuit 202) may have a dedicated TDC 206 associated therewith. For example, for an array of N photodetectors 106, there may be a corresponding array of N TDCs 206. Alternatively, a single TDC 206 may be associated with multiple photodetectors 106. Likewise, a single control circuit 204 and a single signal processing circuit 208 may be provided for a one or more photodetectors 202 and/or TDCs 206.

Figure 3:
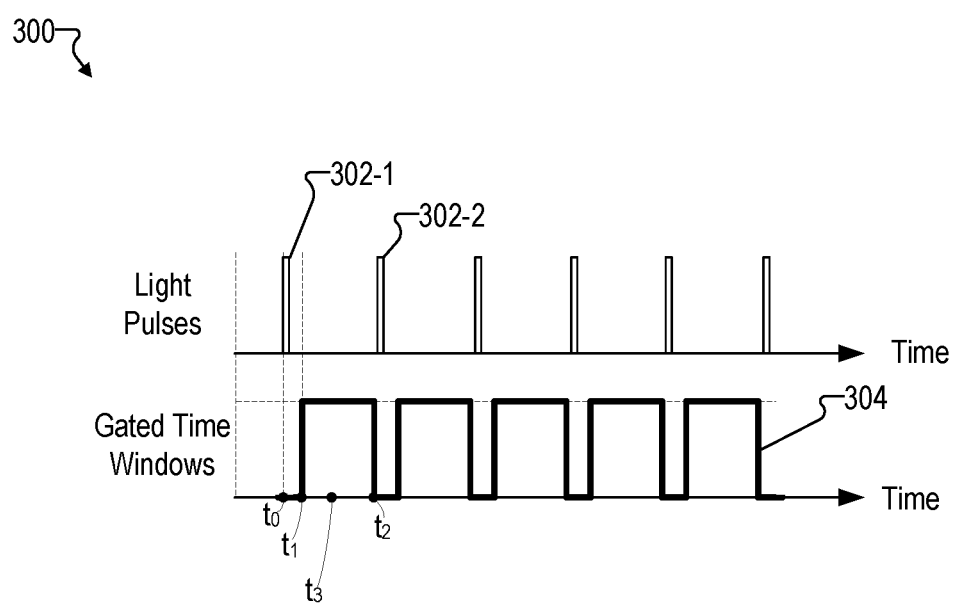
FIG. 3 illustrates an exemplary timing diagram for performing an optical measurement operation using an optical measurement system.

FIG. 3 illustrates an exemplary timing diagram 300 for performing an optical measurement operation using optical measurement system 100. Optical measurement system 100 may be configured to perform the optical measurement operation by directing light pulses (e.g., laser pulses) toward a target within a body (e.g., body 102). The light pulses may be short (e.g., 10-2000 picoseconds (ps)) and repeated at a high frequency (e.g., between 100,000 hertz (Hz) and 100 megahertz (MHz)). The light pulses may be scattered by the target and then detected by optical measurement system 100. Optical measurement system 100 may measure a time relative to the light pulse for each detected photon. By counting the number of photons detected at each time relative to each light pulse repeated over a plurality of light pulses, optical measurement system 100 may generate a histogram that represents a light pulse response of the target (e.g., a temporal point spread function (TPSF)). The terms histogram and TPSF are used interchangeably herein to refer to a light pulse response of a target.

For example, timing diagram 300 shows a sequence of light pulses 302 (e.g., light pulses 302-1 and 302-2) that may be applied to the target (e.g., tissue within a brain of a user, blood flow, a fluorescent material used as a probe in a body of a user, etc.). Timing diagram 300 also shows a pulse wave 304 representing predetermined gated time windows (also referred as gated time periods) during which photodetectors 106 are gated ON to detect photons. Referring to light pulse 302-1, light pulse 302-1 is applied at a time $t_0$. At a time $t_1$, a first instance of the predetermined gated time window begins. Photodetectors 106 may be armed at time $t_1$, enabling photodetectors 106 to detect photons scattered by the target during the predetermined gated time window. In this example, time $t_1$ is set to be at a certain time after time $t_0$, which may minimize photons detected directly from the laser pulse, before the laser pulse reaches the target. However, in some alternative examples, time $t_1$ is set to be equal to time $t_0$.

At a time $t_2$, the predetermined gated time window ends. In some examples, photodetectors 106 may be disarmed at time $t_2$. In other examples, photodetectors 106 may be reset (e.g., disarmed and re-armed) at time $t_2$ or at a time subsequent to time $t_2$. During the predetermined gated time window, photodetectors 106 may detect photons scattered by the target. Photodetectors 106 may be configured to remain armed during the predetermined gated time window such that photodetectors 106 maintain an output upon detecting a photon during the predetermined gated time window. For example, a photodetector 106 may detect a photon at a time $t_3$, which is during the predetermined gated time window between times $t_1$ and $t_2$. The photodetector 106 may be configured to provide an output indicating that the photodetector 106 has detected a photon. The photodetector 106 may be configured to continue providing the output until time $t_2$, when the photodetector may be disarmed and/or reset. Optical measurement system 100 may generate an accumulated output from the plurality of photodetectors. Optical measurement system 100 may sample the accumulated output to determine times at which photons are detected by photodetectors 106 to generate a TPSF.

As mentioned, in some alternative examples, photodetector 106 may be configured to operate in a free-running mode such that photodetector 106 is not actively armed and disarmed (e.g., at the end of each predetermined gated time window represented by pulse wave 304). In contrast, while operating in the free-running mode, photodetector 106 may be configured to reset within a configurable time period after an occurrence of a photon detection event (i.e., after photodetector 106 detects a photon) and immediately begin detecting new photons. However, only photons detected within a desired time window (e.g., during each gated time window represented by pulse wave 304) may be included in the TPSF.

Figure 4:
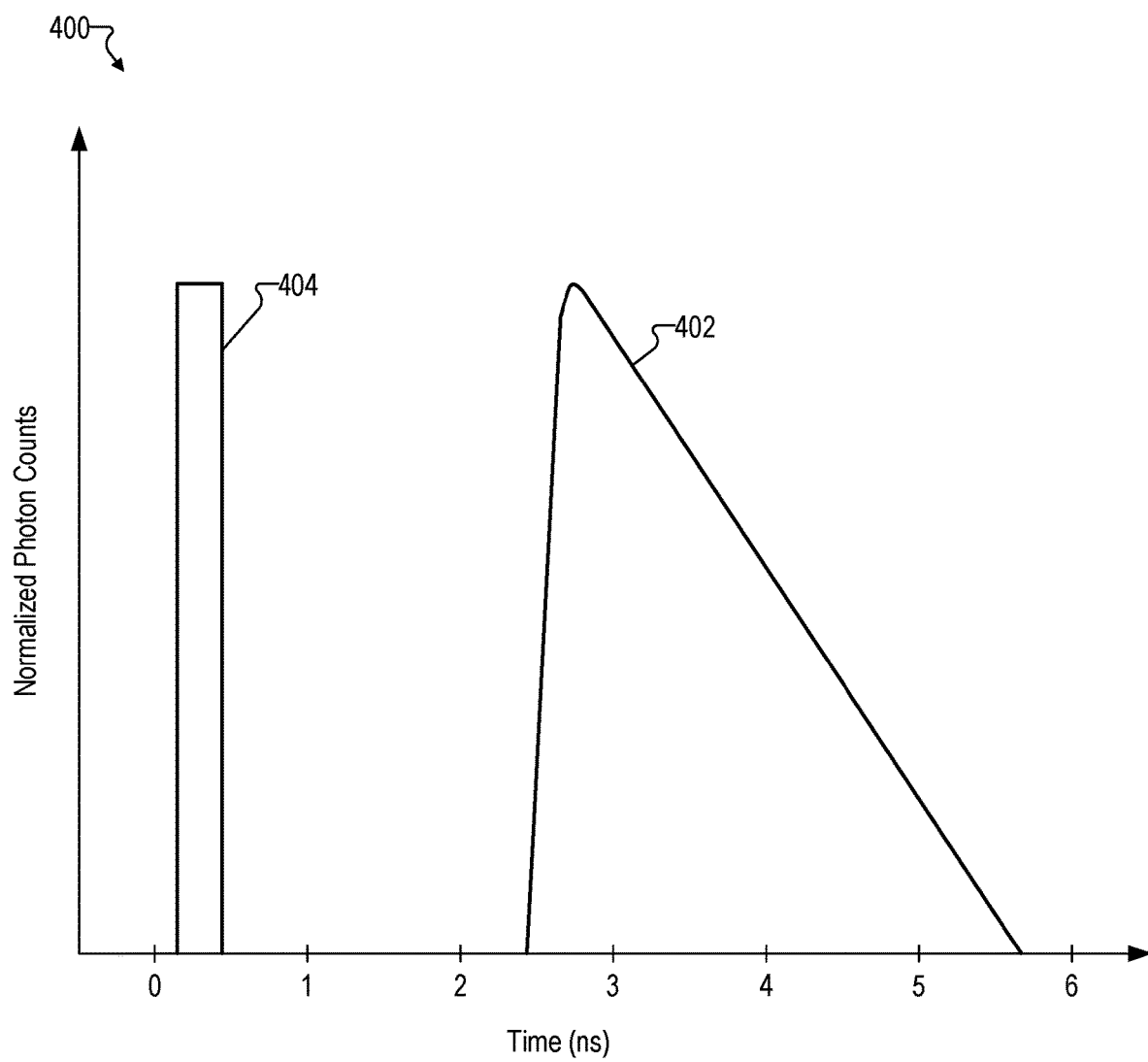
FIG. 4 illustrates a graph of an exemplary temporal point spread function that may be generated by an optical measurement system in response to a light pulse.

FIG. 4 illustrates a graph 400 of an exemplary TPSF 402 that may be generated by optical measurement system 100 in response to a light pulse 404 (which, in practice, represents a plurality of light pulses). Graph 400 shows a normalized count of photons on a y-axis and time bins on an x-axis. As shown, TPSF 402 is delayed with respect to a temporal occurrence of light pulse 404. In some examples, the number of photons detected in each time bin subsequent to each occurrence of light pulse 404 may be aggregated (e.g., integrated) to generate TPSF 402. TPSF 402 may be analyzed and/or processed in any suitable manner to determine or infer detected neural activity.

Optical measurement system 100 may be implemented by or included in any suitable device. For example, optical measurement system 100 may be included, in whole or in part, in a non-invasive wearable device (e.g., a headpiece) that a user may wear to perform one or more diagnostic, imaging, analytical, and/or consumer-related operations. The non-invasive wearable device may be placed on a user's head or other part of the user to detect neural activity. In some examples, such neural activity may be used to make behavioral and mental state analysis, awareness and predictions for the user.

Mental state described herein refers to the measured neural activity related to physiological brain states and/or mental brain states, e.g., joy, excitement, relaxation, surprise, fear, stress, anxiety, sadness, anger, disgust, contempt, contentment, calmness, focus, attention, approval, creativity, positive or negative reflections/attitude on experiences or the use of objects, etc. Further details on the methods and systems related to a predicted brain state, behavior, preferences, or attitude of the user, and the creation, training, and use of neuromes can be found in U.S. Provisional Patent Application No. 63/047,991, filed Jul. 3, 2020. Exemplary measurement systems and methods using biofeedback for awareness and modulation of mental state are described in more detail in U.S. patent application Ser. No. 16/364,338, filed Mar. 26, 2019, published as US2020/0196932A1. Exemplary measurement systems and methods used for detecting and modulating the mental state of a user using entertainment selections, e.g., music, film/video, are described in more detail in U.S. patent application Ser. No. 16/835,972, filed Mar. 31, 2020, published as US2020/0315510A1. Exemplary measurement systems and methods used for detecting and modulating the mental state of a user using product formulation from, e.g., beverages, food, selective food/drink ingredients, fragrances, and assessment based on product-elicited brain state measurements are described in more detail in U.S. patent application Ser. No. 16/853,614, filed Apr. 20, 2020, published as US2020/0337624A1. Exemplary measurement systems and methods used for detecting and modulating the mental state of a user through awareness of priming effects are described in more detail in U.S. patent application Ser. No. 16/885,596, filed May 28, 2020, published as US2020/0390358A1. These applications and corresponding U.S. publications are incorporated herein by reference in their entirety.

Figure 5:
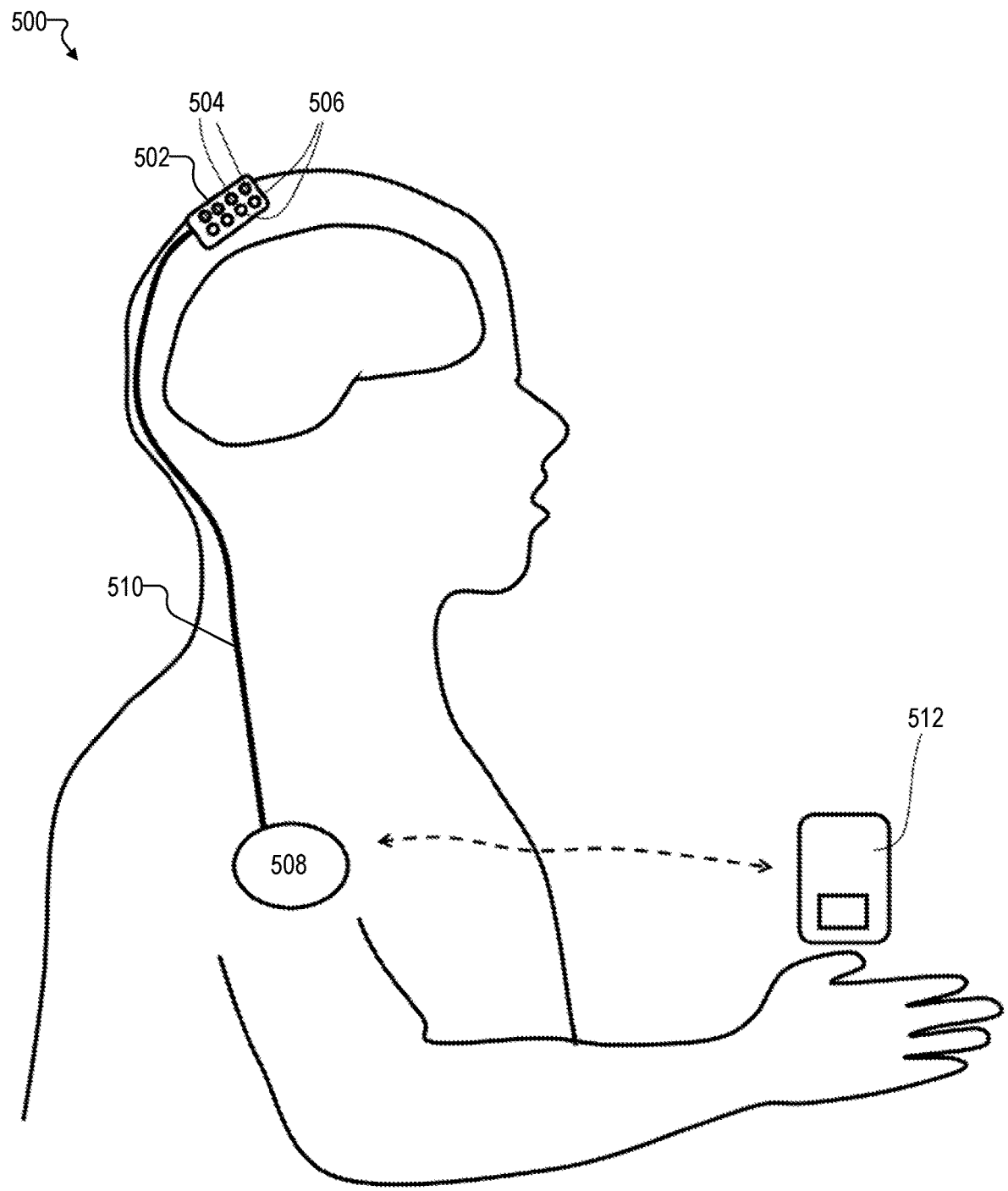
FIG. 5 shows an exemplary non-invasive wearable brain interface system.

FIG. 5 shows an exemplary non-invasive wearable brain interface system 500 ("brain interface system 500") that implements optical measurement system 100 (shown in FIG. 1). As shown, brain interface system 500 includes a head-mountable component 502 configured to be attached to a user's head. Head-mountable component 502 may be implemented by a cap shape that is worn on a head of a user. Alternative implementations of head-mountable component 502 include helmets, beanies, headbands, other hat shapes, or other forms conformable to be worn on a user's head, etc. Head-mountable component 502 may be made out of any suitable cloth, soft polymer, plastic, hard shell, and/or any other suitable material as may serve a particular implementation. Examples of headgears used with wearable brain interface systems are described more fully in U.S. Pat. No. 10,340,408, incorporated herein by reference in its entirety.

Head-mountable component 502 includes a plurality of detectors 504, which may implement or be similar to detector 104, and a plurality of light sources 506, which may be implemented by or be similar to light source 110. It will be recognized that in some alternative embodiments, head-mountable component 502 may include a single detector 504 and/or a single light source 506.

Brain interface system 500 may be used for controlling an optical path to the brain and for transforming photodetector measurements into an intensity value that represents an optical property of a target within the brain. Brain interface system 500 allows optical detection of deep anatomical locations beyond skin and bone (e.g., skull) by extracting data from photons originating from light source 506 and emitted to a target location within the user's brain, in contrast to conventional imaging systems and methods (e.g., optical coherence tomography (OCT)), which only image superficial tissue structures or through optically transparent structures.

Brain interface system 500 may further include a processor 508 configured to communicate with (e.g., control and/or receive signals from) detectors 504 and light sources 506 by way of a communication link 510. Communication link 510 may include any suitable wired and/or wireless communication link. Processor 508 may include any suitable housing and may be located on the user's scalp, neck, shoulders, chest, or arm, as may be desirable. In some variations, processor 508 may be integrated in the same assembly housing as detectors 504 and light sources 506.

As shown, brain interface system 500 may optionally include a remote processor 512 in communication with processor 508. For example, remote processor 512 may store measured data from detectors 504 and/or processor 508 from previous detection sessions and/or from multiple brain interface systems (not shown). Power for detectors 504, light sources 506, and/or processor 508 may be provided via a wearable battery (not shown). In some examples, processor 508 and the battery may be enclosed in a single housing, and wires carrying power signals from processor 508 and the battery may extend to detectors 504 and light sources 506. Alternatively, power may be provided wirelessly (e.g., by induction).

In some alternative embodiments, head mountable component 502 does not include individual light sources. Instead, a light source configured to generate the light that is detected by detector 504 may be included elsewhere in brain interface system 500. For example, a light source may be included in processor 508 and coupled to head mountable component 502 through optical connections.

Each of the light sources described herein may be implemented by any suitable device. For example, a light source as used herein may be, for example, a distributed feedback (DFB) laser, a super luminescent diode (SLD), a light emitting diode (LED), a diode-pumped solid-state (DPSS) laser, a laser diode (LD), a super luminescent light emitting diode (sLED), a vertical-cavity surface-emitting laser (VCSEL), a titanium sapphire laser, a micro light emitting diode (mLED), and/or any other suitable laser or light source.

Optical measurement system 100 may alternatively be included in a non-wearable device (e.g., a medical device and/or consumer device that is placed near the head or other body part of a user to perform one or more diagnostic, imaging, and/or consumer-related operations). Optical measurement system 100 may alternatively be included in a sub-assembly enclosure of a wearable invasive device (e.g., an implantable medical device for brain recording and imaging).

Optical measurement system 100 may be modular in that one or more components of optical measurement system 100 may be removed, changed out, or otherwise modified as may serve a particular implementation. Additionally or alternatively, optical measurement system 100 may be modular such that one or more components of optical measurement system 100 may be housed in a separate housing (e.g., module) and/or may be movable relative to other components. Exemplary modular multimodal measurement systems are described in more detail in U.S. patent application Ser. No. 17/176,460, filed Feb. 16, 2021, U.S. patent application Ser. No. 17/176,470, filed Feb. 16, 2021, U.S. patent application Ser. No. 17/176,487, filed Feb. 16, 2021, U.S. Provisional Patent Application No. 63/038,481, filed Jun. 12, 2020, and U.S. patent application Ser. No. 17/176,560, filed Feb. 16, 2021, which applications are incorporated herein by reference in their respective entireties.

Figure 6:
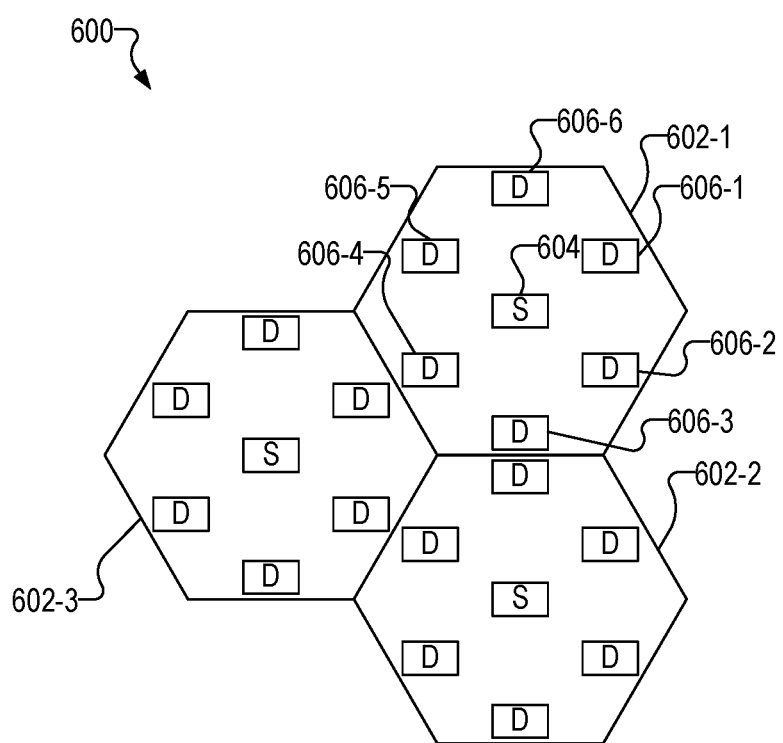
FIG. 6 shows an exemplary wearable module assembly.

To illustrate, FIG. 6 shows an exemplary wearable module assembly 600 ("assembly 600") that implements one or more of the optical measurement features described herein. Assembly 600 may be worn on the head or any other suitable body part of the user. As shown, assembly 600 may include a plurality of modules 602 (e.g., modules 602-1 through 602-3). While three modules 602 are shown to be included in assembly 600 in FIG. 6, in alternative configurations, any number of modules 602 (e.g., a single module up to sixteen or more modules) may be included in assembly 600. Moreover, while modules 602 are shown to be adjacent to and touching one another, modules 602 may alternatively be spaced apart from one another (e.g., in implementations where modules 602 are configured to be inserted into individual slots or cutouts of the headgear).

Each module 602 includes a source 604 and a plurality of detectors 606 (e.g., detectors 606-1 through 606-6). Source 604 may be implemented by one or more light sources similar to light source 110. Each detector 606 may implement or be similar to detector 104 and may include a plurality of photodetectors (e.g., SPADs) as well as other circuitry (e.g., TDCs). As shown, detectors 606 are arranged around and substantially equidistant from source 604. In other words, the spacing between a light source (i.e., a distal end portion of a light source optical conduit) and the detectors (i.e., distal end portions of optical conduits for each detector) are maintained at the same fixed distance on each module to ensure homogeneous coverage over specific areas and to facilitate processing of the detected signals. The fixed spacing also provides consistent spatial (lateral and depth) resolution across the target area of interest, e.g., brain tissue. Moreover, maintaining a known distance between the light emitter and the detector allows subsequent processing of the detected signals to infer spatial (e.g., depth localization, inverse modeling) information about the detected signals. Detectors 606 may be alternatively disposed as may serve a particular implementation.

Figure 7:
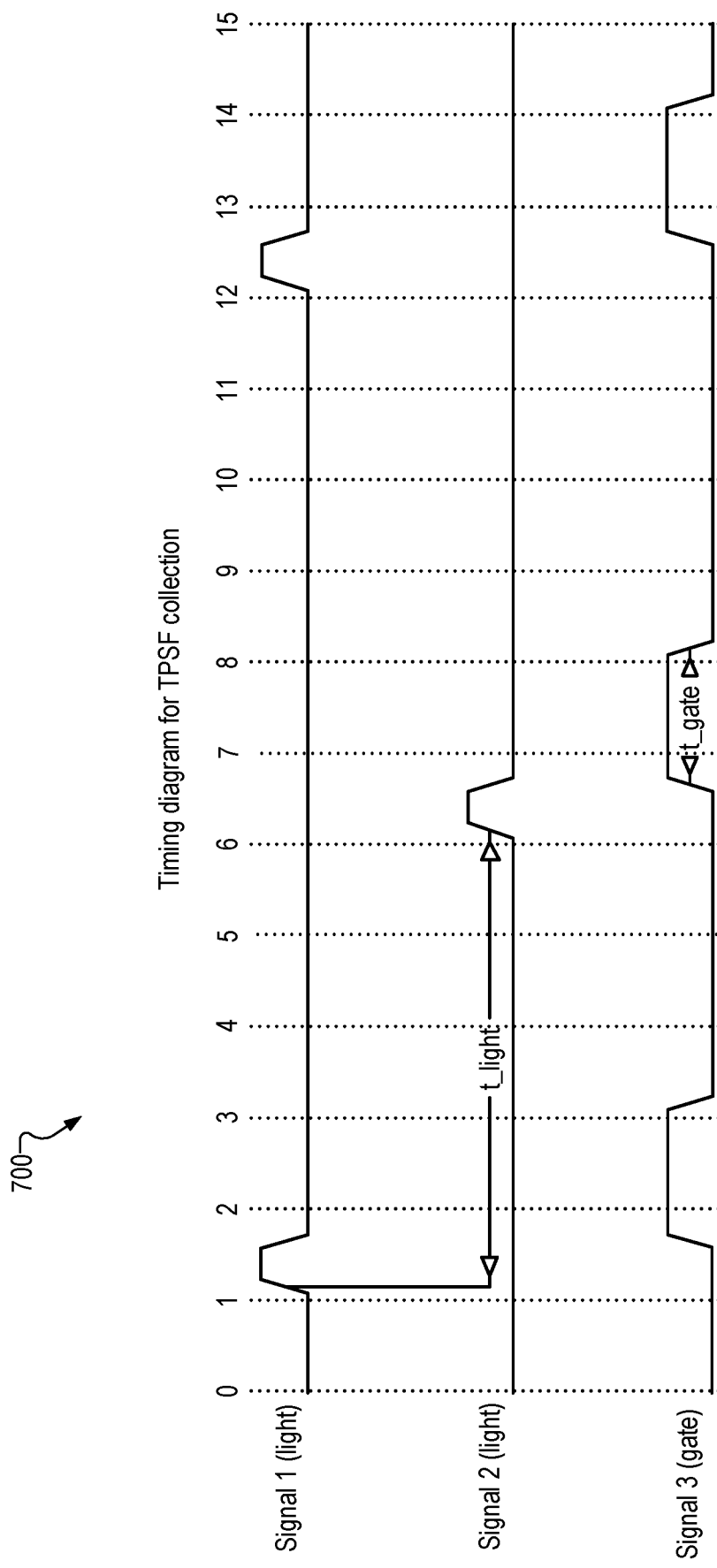
FIG. 7 shows an exemplary timing diagram.

FIG. 7 shows an exemplary timing diagram 700 of a number of pulsed signals that may be provided in optical measurement system 100 to accurately capture a temporal point spread function (TPSF) from a diffuse medium. Signal 1 represents a first pulsed light signal that may be applied to a target, signal 2 represents a second pulsed light signal that may be applied to the target, and signal 3 represents a pulsed gating signal that may be used to specify a time period (referred to as t_gate) during which a SPAD is ON (i.e., armed) to detect a photon from pulses included in the first and second pulsed light signals after they are scattered by the target. An exemplary time between the rising edges of a pulse in the first and the second light pulse signals is t_light (e.g., around 25 ns if the light repetition rate is 40 MHz). Some of the systems, circuits, and methods described herein may be used to precisely specify a duration and temporal position of the gate pulses included in the gating signal with respect to the light pulses. Some of the systems, circuits, and methods described herein may additionally or alternatively be used to precisely specify a duration and temporal position of various other pulses used within optical measurement system 100.

Figure 8:
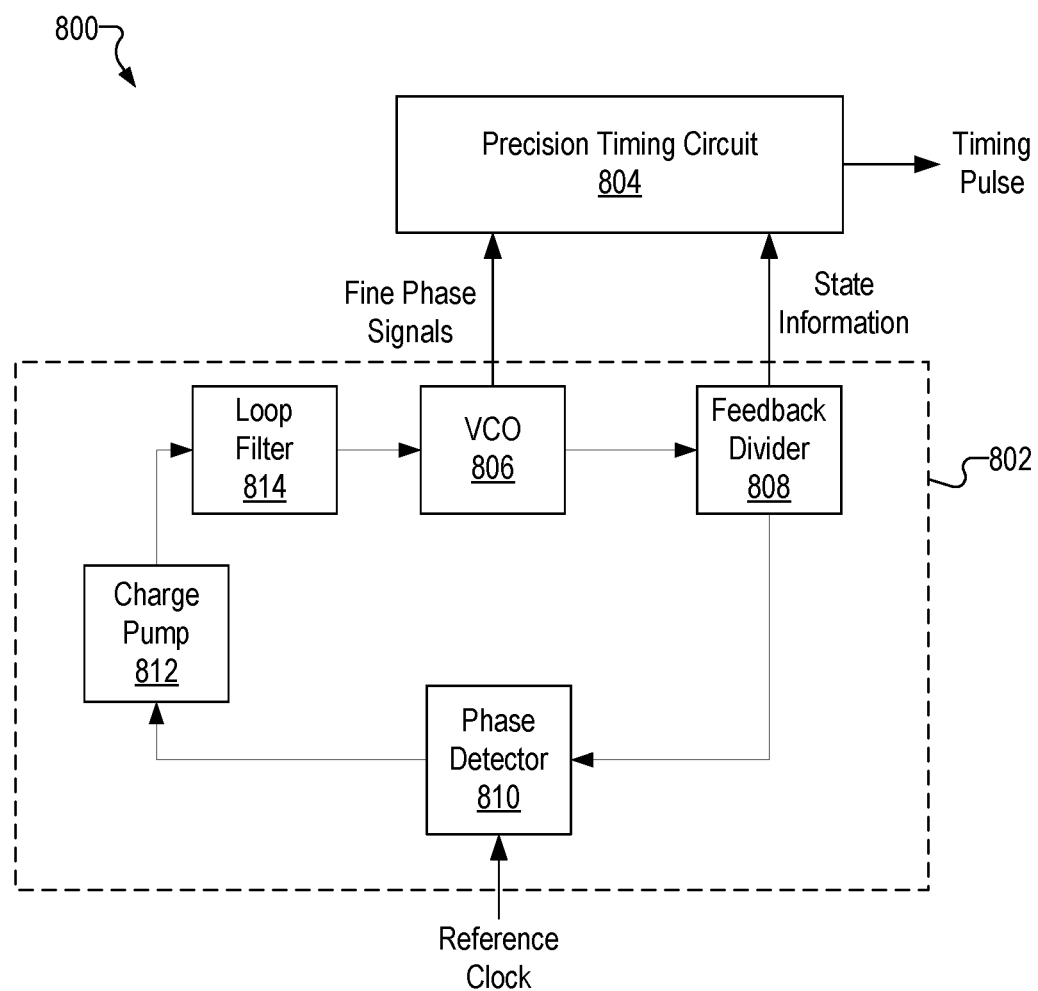
FIGS. 8-9 illustrate exemplary phase lock loop (PLL) circuit based architectures.

FIG. 8 illustrates an exemplary PLL circuit based architecture 800 that may be included within optical measurement system 100 to generate and set a temporal position (e.g., of a rising edge and/or of a falling edge) of a timing pulse. As shown, architecture 800 includes a PLL circuit 802 communicatively coupled to a precision timing circuit 804. PLL circuit 802 includes a VCO 806, a feedback divider 808, a phase detector 810, a charge pump 812, and a loop filter 814 connected in a feedback loop configuration. Phase detector 810 may receive a reference clock as an input such that PLL circuit 802 has a PLL feedback period defined by the reference clock. The reference clock may have any suitable frequency, such as any frequency between 1 MHz and 200 MHz.

VCO 806 may be implemented by any suitable combination of circuitry (e.g., a differential multi-stage gated ring oscillator (GRO) circuit) and is configured to lock to the reference clock (i.e., to a multiple of a frequency of the reference clock). To that end, VCO 806 may include a plurality of stages configured to output a plurality of fine phase signals each having a different phase and uniformly distributed in time. In some examples, each stage may output two fine phase signals that have complimentary phases. VCO 806 may include any suitable number of stages configured to output any suitable number of fine phase signals (e.g., eight stages that output sixteen fine phase signals). The duration of a fine phase signal pulse depends on the oscillator frequency of VCO 806 and the total number of fine phase signals. For example, if the oscillator frequency is 1 gigahertz (GHz) and the total number of fine phase signals is sixteen, the duration of a pulse included in a fine phase signal is 1 GHz/16, which is 62.5 picoseconds (ps). As described herein, these fine phase signals may provide precision timing circuit 804 with the ability to adjust a phase (i.e., temporal position) of a timing pulse with relatively fine resolution.

Feedback divider 808 is configured to be clocked by a single fine phase signal included in the plurality of fine phase signals output by VCO 806 and have a plurality of feedback divider states during the PLL feedback period. The number of feedback divider states depends on the oscillator frequency of VCO 806 and the frequency of the reference clock. For example, if the oscillator frequency is 1 gigahertz (GHz) and the reference clock has a frequency of 50 MHz, the number of feedback divider states is equal to 1 GHz/50 MHz, which is equal to 20 feedback divider states. As described herein, these feedback divider states may provide precision timing circuit 804 with the ability to adjust a phase (i.e., temporal position) of a timing pulse with relatively course resolution.

Feedback divider 808 may be implemented by any suitable circuitry. In some alternative examples, feedback divider 808 is at least partially integrated into precision timing circuit 804.

As shown, the fine phase signals output by VCO 806 and state information (e.g., signals and/or data) representative of the feedback divider states within feedback divider 808 are input into precision timing circuit 804. Precision timing circuit 804 may be configured to generate a timing pulse and set, based on a combination of one of the fine phase signals and one of the feedback dividers states, a temporal position of the timing pulse within the PLL feedback period. For example, if there are N total fine phase signals and M total feedback divider states, precision timing circuit 804 may set the temporal position of the timing pulse to be one of N times M possible temporal positions within the PLL feedback period. To illustrate, if N is 16 and M is 20, and if the duration of a pulse included in a fine phase signal is 62.5 ps, the temporal position of the timing pulse may be set to be one of 320 possible positions in 62.5 ps steps.

The timing pulse generated by precision timing circuit 804 may be used within optical measurement system 100 in any suitable manner. For example, the timing pulse may be configured to trigger a start (e.g., a rising edge) of an output pulse used by a component within optical measurement system 100. Alternatively, the timing pulse may be configured to trigger an end (e.g., a falling edge) of an output pulse used by a component within optical measurement system 100. Alternatively, the timing pulse itself may be provided for use as an output pulse used by a component within optical measurement system 100. In some examples, precision timing circuit 804 may generate multiple timing pulses each used for a different purpose within optical measurement system 100. These examples are each described in more detail herein.

Figure 9:
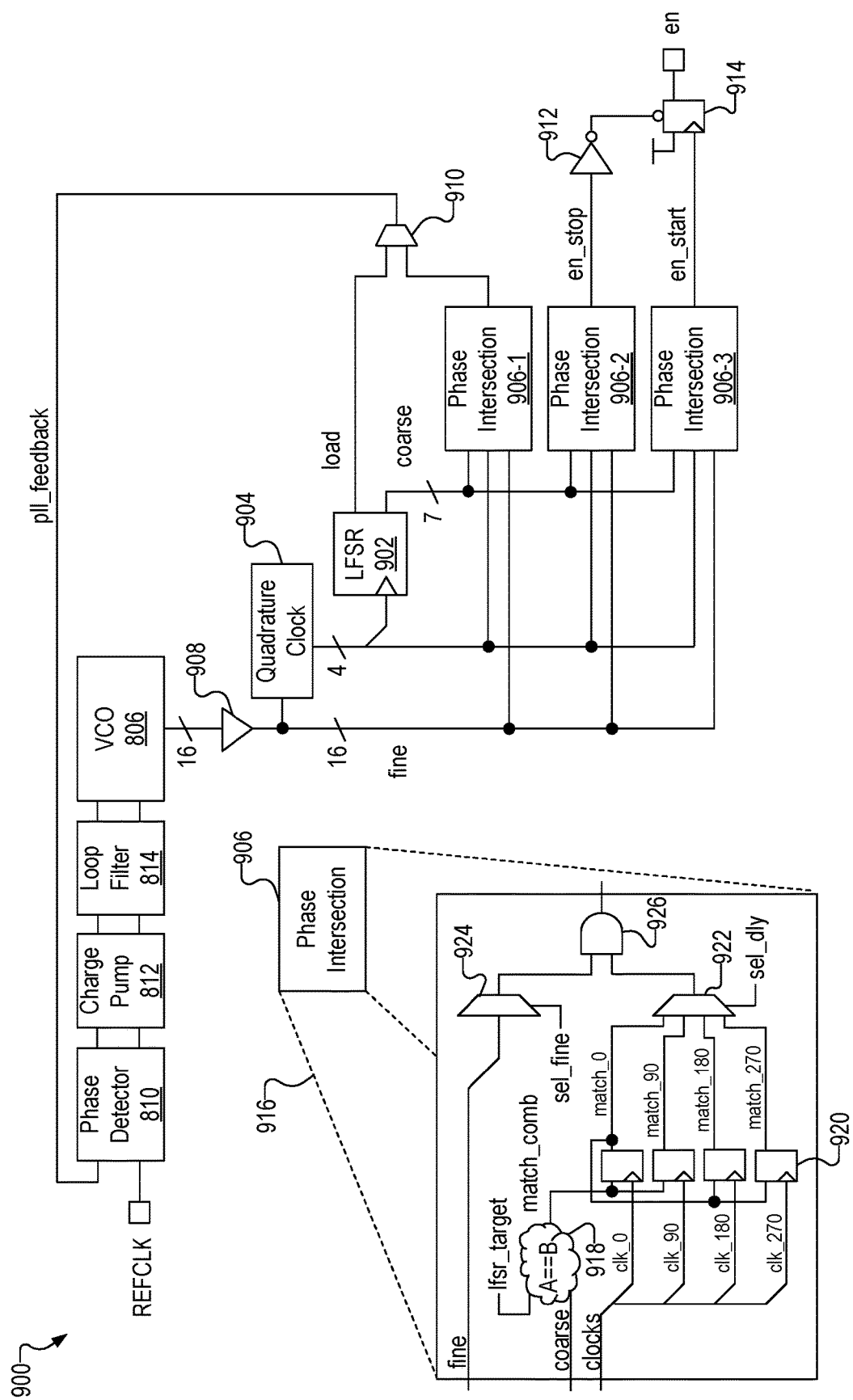

FIG. 9 shows an exemplary implementation 900 of PLL circuit based architecture 800. In implementation 900, feedback divider 808 is implemented by a linear feedback shift register (LFSR) 902 and precision timing circuit 804 is implemented by a quadrature clock block 904, a plurality of phase intersection blocks (e.g., phase intersection block 906-1 through 906-3), and various other electrical components (e.g., a buffer 908, a multiplexer 910, a gate 912, and a register 914). FIG. 9 also depicts a call out 916 that shows exemplary logic included in each phase intersection block 906.

In implementation 900, VCO 806 is configured to output sixteen fine phase signals (labeled "fine" in FIG. 9). The fine phase signals are buffered by buffer 908 and input into quadrature clock block 904 and each phase intersection block 906.

Quadrature clock block 904 is configured to select, from the plurality of fine phase signals generated by VCO 806, four fine phase signals that are quadrature shifted from each other (e.g., evenly spaced at a relative 0, 90, 180, and 270 degrees) for use as quadrature clock signals. One of the quadrature clock signals (e.g., quadrature phase 0) is used to clock LFSR 902. The quadrature clock signals are also each provided to each phase intersection block 906.

LFSR 902 is configured to have a plurality of feedback divider states during each PLL feedback period, as described herein. LFSR 902 outputs state information (labeled "coarse" in FIG. 9) by, for example, counting up to the total number of feedback dividers states once per PLL feedback period. This course count is provided to each phase intersection block 906.

LFSR 902 is further configured to generate a load signal, which occurs each time LFSR 902 wraps. The load signal and an output of phase intersection block 906-1 are input into a multiplexer 910, which selects one of the signals for use as the feedback signal (pll_feedback) that is provided to phase detector 810. This will be described in more detail below.

Each of phase intersection blocks 906 can be independently programmed to generate a single pulse (i.e., a timing pulse) that is the intersection or combination of a chosen coarse state (i.e., a chosen feedback divider state), and a chosen fine signal phase (i.e., a phase of a chosen fine phase signal). It will be recognized that any number of phase intersection blocks 906 may be included in precision timing circuit 804 to generate any number of timing pulses as may serve a particular implementation.

Once per PLL feedback period, the feedback divider state matches the programmed target, generating a combinational match signal. The quadrature clock signals are used to register and delay the combinational match signal. In this way, four match signals are generated, which are quadrature shifted from each other and which each occur once per PLL feedback period. Inside each phase intersection block 906, one of the selected fine phases is logically ANDed with one of the registered match signals, resulting in a single output pulse per PLL feedback period. The temporal position of this output pulse can be selected with a granularity of the VCO stage. For example, if the PLL circuit is locked to a VCO oscillator frequency of 1 GHz and each of the eight VCO oscillator stages has a 62.5 ps delay, and the PLL reference clock is 50 MHz (feedback period is 20 ns), then the feedback divider has 20 states (coarse), the ring oscillator has 16 states (fine), and the temporal position of the timing pulse output by the phase intersection block 906 can be programmed to be any of 20*16=320 possible positions in 62.5 ps steps.

To illustrate, with respect to the phase intersection block 906 shown in call out 916, phase intersection block 906 may be configured receive the following inputs: the plurality of fine phase signals (labeled "fine"), the quadrature clock signals (labeled "clocks") output by quadrature clock block 904, a programmable target state signal (labeled "lfsr_target") that identifies a target feedback divider state included in the plurality of feedback divider states of LFSR 902, and a programmable target fine phase signal (labeled "sel_fine") identifying a target fine phase signal included in the plurality of fine phase signals and that, in combination with the target feedback divider state, results in the timing pulse output by phase intersection block 906 occurring at a desired temporal position.

As illustrated by comparison block 918, phase intersection block 906 is configured to generate a combination match signal (labeled "match_comb") when a current feedback divider state (e.g., a particular feedback divider state count) matches the target feedback state. Phase intersection block 906 may use the quadrature clock signals (e.g., by inputting them into registers 920) to generate four registered match signals representative of the combination match signal. These four registered match signals are represented by match_0, match_90, match_180, and match_270 are quadrature shifted from each other. The four registered match signals are input into a multiplexer 922, which receives a selector input labeled sel_dly that selects a particular match signal from the four registered match signal that is aligned (e.g., most aligned) with a pulse included in the target fine phase signal. The selected match signal and the target fine phase signal (as output by a multiplexer 924 controlled by a selector signal labeled sel_fine) into an AND gate 926 to output the timing pulse at the temporal position.

The timing pulse of a single phase intersection block 906 may be a relatively narrow pulse. For example, the timing pulse may have a pulse width of half of the VCO oscillator period. In this example, if the VCO oscillator frequency is 1 GHz (i.e., the period is 1 ns), the timing pulse width will be 500 ps. For some applications, a different pulse width for a particular signal (e.g., a gating signal) is desirable. In this case, two phase intersection blocks (e.g., phase intersection blocks 906-2 and 906-3) may be combined and used to trigger the start and end of an output pulse used by a component in optical measurement system 100. For example, in the example of FIG. 9, phase intersection block 906-3 is configured to output a timing pulse labeled en_start, which is configured to trigger a start of an output pulse labeled en. Phase intersection block 906-2 is configured to output a timing pulse labeled en_stop, which is configured to trigger an end of the output pulse labeled en. The temporal positions of the timing pulses may be set as described herein to specify a duration of the output pulse. In the example of FIG. 9, at the programmed time, the rise of en_start causes a register to output a logic 1 to the signal named en. At a different programmed time, the rise of the gate_stop signal resets the register to logic 0.

As mentioned, the load signal generated by LFSR 902 and an output signal of phase intersection block 906-1 are input into multiplexer 910, which selects one of the signals for use as the feedback signal (pll_feedback) that is provided to phase detector 810. By using the output signal (which has a programmable phase as described herein) of phase intersection block 906-1 as the PLL feedback signal (pll_feedback), the phase of the PLL feedback signal shifts the position of all other signals (e.g., timing pulses) generated by the phase intersection blocks 906 and other circuitry (e.g., timestamp generation circuitry, as described herein) connected to the PLL circuit. This is because the PLL feedback signal is part of the PLL control loop. The PLL will adjust the VCO oscillator phase and frequency until the reference clock (REFCLK) and PLL feedback signals are aligned (typically only positive or negative edges are aligned since pulse widths are often different). If the PLL control loop advances the phase of the PLL feedback signal to cause it to align in time with the REFCLK signal, then the other phase intersection block outputs advance as well. This provides an absolute phase reference to the REFCLK signal. The individual phase intersection blocks 906 can be independently programmed, which allows for any relative spacing between the timing pulses within the PLL feedback period. This configuration gives precision and flexibility.

Figure 10:
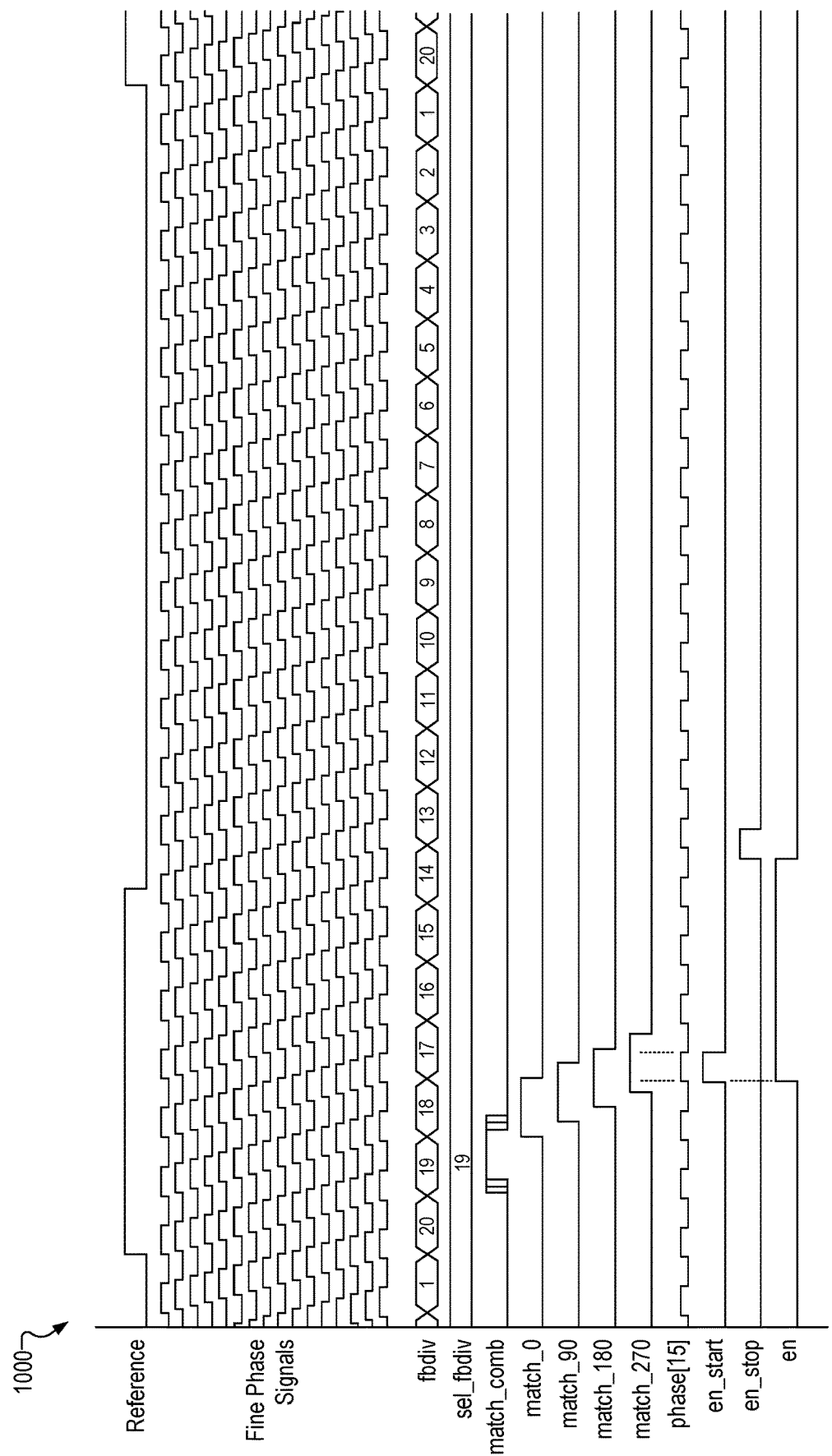
FIG. 10 shows an exemplary timing diagram.

FIG. 10 shows a timing diagram 1000 showing a PLL reference clock (Reference), fine phase signals generated by VCO 806, and a representation of the PLL feedback divider state (fbdiv). In this example, feedback divider 808 counts from 20 down to 1 and repeats. Each feedback divider state occurs only once per reference period, thus providing a coarse position that is unique within the reference period. Within each feedback divider state, VCO 806 cycles through its states (sixteen in this example), thus providing a fine position that is not unique within the reference period. The intersection of a particular coarse state and fine state gives a precise, unique position within the reference period.

As shown, the beginning of an output signal (en_start) is triggered when feedback state is 19 (sel_fbdiv) through a cascade of events. A combinational equality comparison of fbdiv and sel_fbdiv (named coarse and lfsr_target in FIG. 9) gives a combinational signal, match_comb=(fbdiv==sel_fbdiv). This combinational match signal is then sampled by quadrature clocks giving clean quadrature-shifted match signals at relative 0, 90, 180, and 270 degrees. A multiplexer (e.g., multiplexer 922) selects one of these four match signals, chosen to center the fine phase within the coarse match signal. Another multiplexer (e.g., multiplexer 924) selects one of the sixteen fine phase signals. These two signals are then ANDed together (e.g., with AND gate 926). When properly aligned, this circuit can generate a single timing pulse anywhere within the reference period, with the same spacing resolution as the VCO oscillator phase.

In timing diagram 1000, phase intersection block 906-3 generates en_start, which marks the beginning of the en pulse. Phase intersection block 906-2 generates en_stop, which marks the end of the en pulse. In this way, a precise, repeatable output signal (en) is generated.

As mentioned, a timing pulse generated by precision timing circuit 804 may be used within optical measurement system 100 in any suitable manner. For example, a timing pulse generated by precision timing circuit 804 or an output pulse having a start time or an end time defined by the temporal position of the timing pulse may be configured to be used as a gate pulse configured to trigger the arming and disarming of a photodetector (e.g., a SPAD).

Additionally or alternatively, a timing pulse generated by precision timing circuit 804 or an output pulse having a start time or an end time defined by the temporal position of the timing pulse may be configured to be used as a calibration pulse for one or more TDCs or another component of optical measurement system 100.

Additionally or alternatively, a timing pulse generated by precision timing circuit 804 or an output pulse having a start time or an end time defined by the temporal position of the timing pulse may be configured to be used to trigger a light source to output a light pulse.

In some examples, precision timing circuit 804 may be configured to generate a sequence of timing pulses each configured to have the same temporal position within the PLL feedback period. As the sequence is being generated, precision timing circuit 804 may receive a command to adjust the temporal position of the timing pulses within the PLL feedback period. The command may be provided by a user of optical measurement system 100 or automatically by a component within optical measurement system 100 without input being provided by a user of optical measurement system 100. In response to receiving the command, precision timing circuit 804 may adjust the temporal position by selecting a different fine phase signal and/or feedback divider state to be used as the combination that sets the temporal position. Based on the updated combination, precision timing circuit 804 may adjust the temporal position of subsequent timing pulses that are generated.

Figure 11:
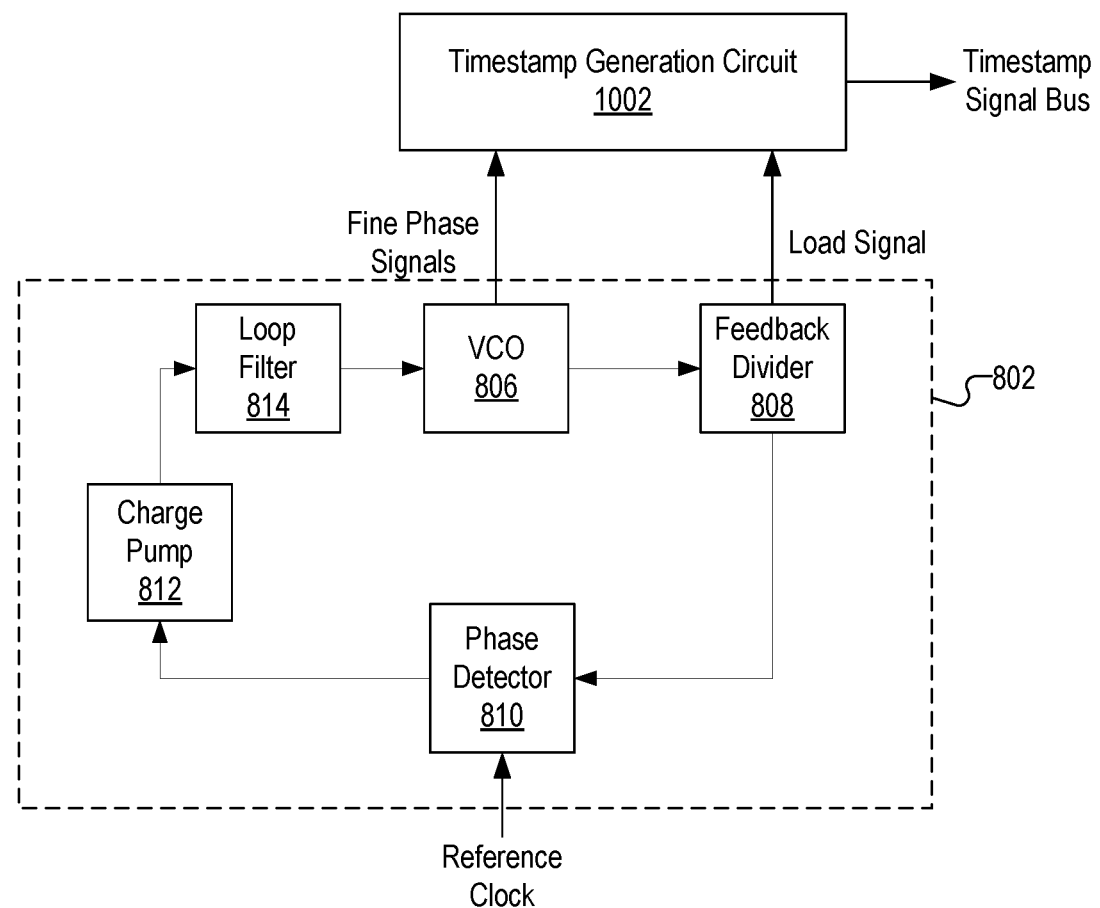
FIGS. 11-13 illustrate exemplary PLL circuit based architectures.

FIG. 11 illustrates an exemplary PLL circuit based architecture 1100 that may be configured to generate and distribute a timestamp signal bus to one or more TDCs (e.g., to each TDC included in an array of TDCs) included in optical measurement system 100. As shown, architecture 1100 includes the PLL circuit 802 described in connection with FIG. 8 communicatively coupled to a timestamp generation circuit 1002. Timestamp generation circuit 1002 may be configured to generate, based on a subset of the fine phase signals that define a plurality of fine states for the plurality of fine phase signals, a timestamp signal bus representative of a plurality of timestamp symbols. Timestamp generation circuit 1002 may be further configured to transmit the timestamp signal bus to one or more TDCs. These operations are described in more detail herein.

Figure 12:
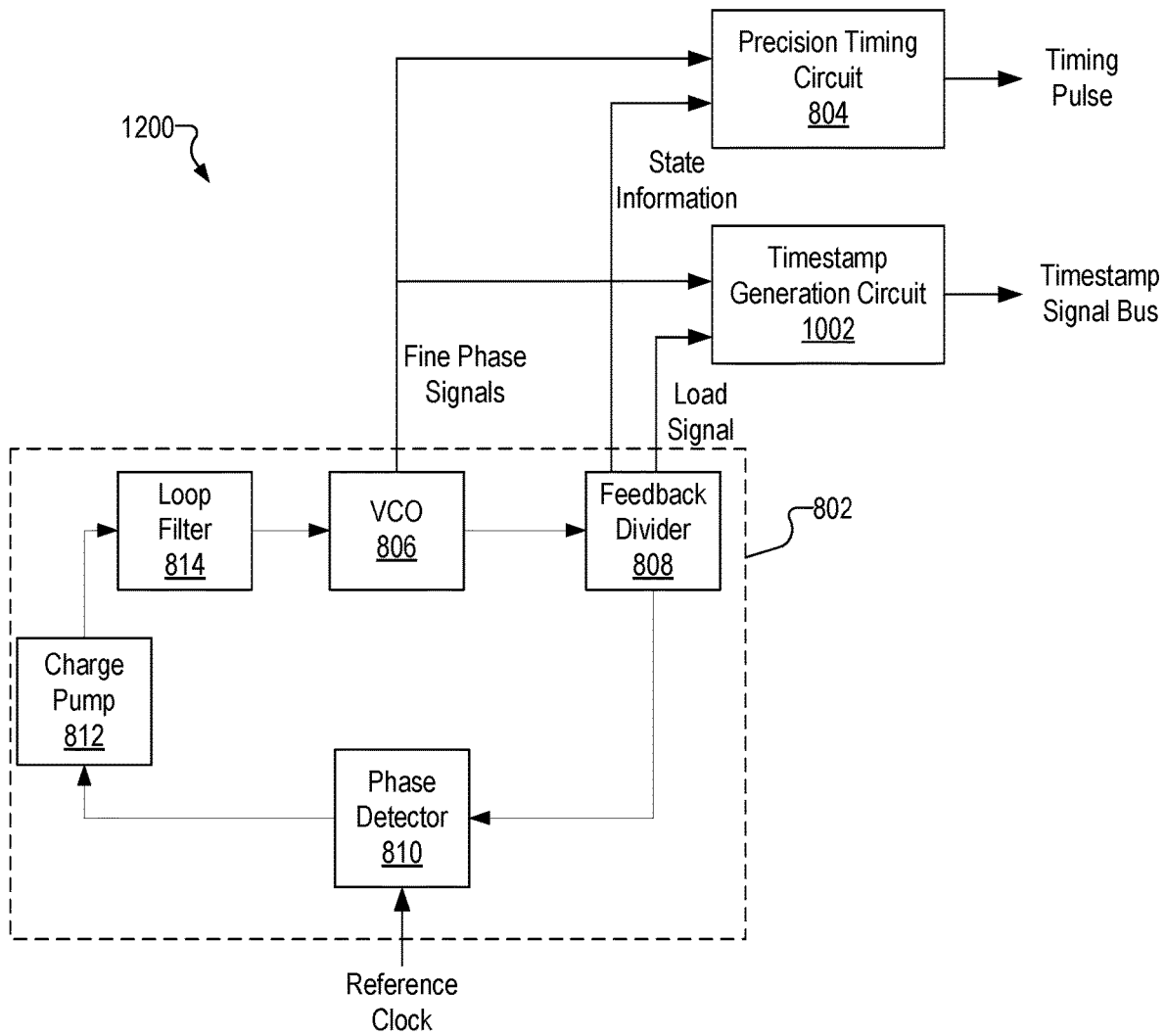

In some examples, PLL circuit based architectures 800 and 1100 may be combined to form a PLL circuit based architecture that includes both precision timing and timestamp generation functionality. For example, FIG. 12 shows an exemplary PLL circuit based architecture 1200 that includes both precision timing circuit 804 and timestamp generation circuit 1002. PLL circuit based architecture 1200 will be used in the examples provided herein.

Figure 13:
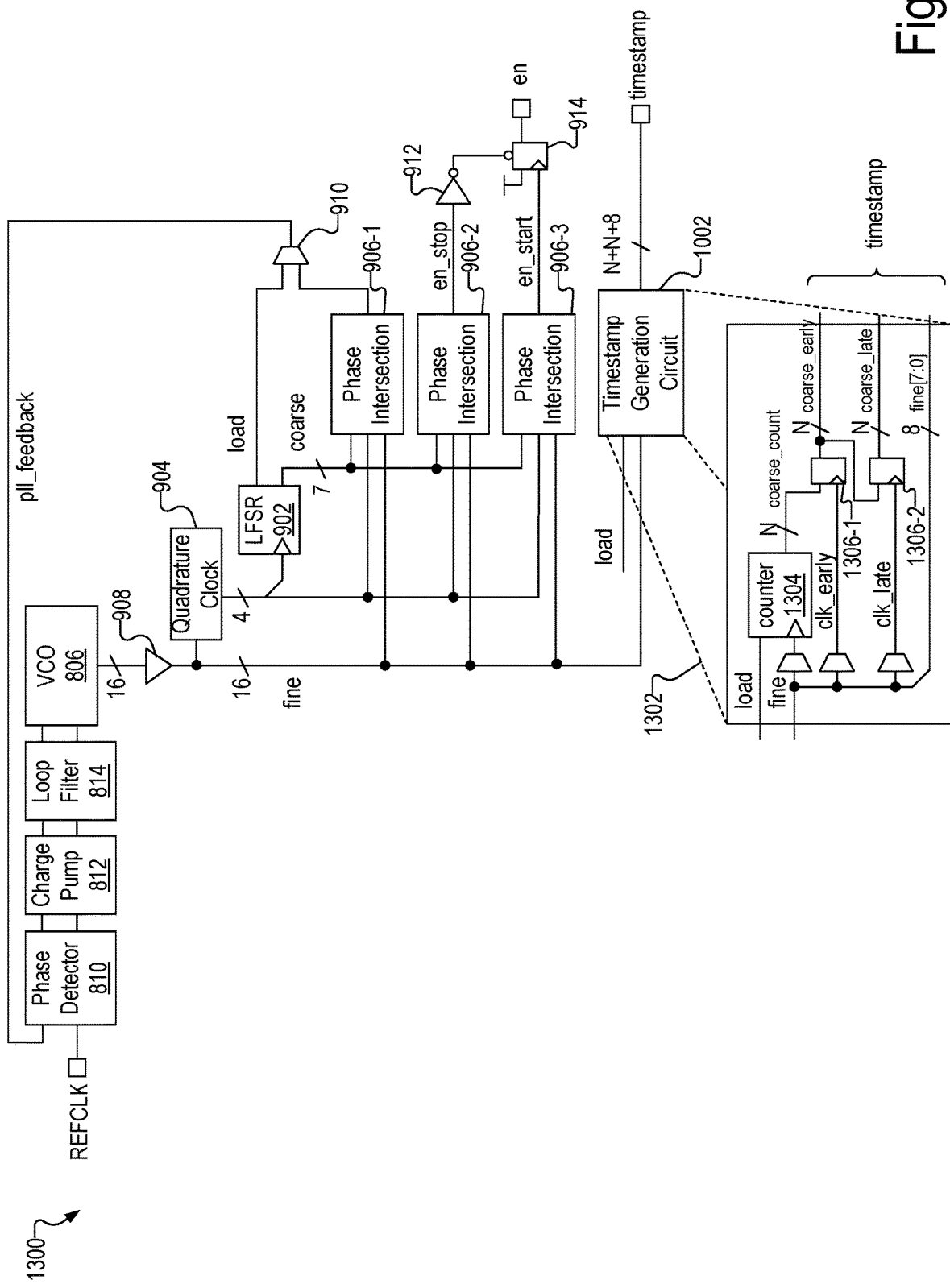

FIG. 13 shows an exemplary implementation 1300 of PLL circuit based architecture 1200. Implementation 1300 is similar to implementation 900, except that implementation 1300 also includes a timestamp generation circuit 1002. FIG. 13 depicts a call out 1302 that shows exemplary logic included in timestamp generation circuit 1002.

Timestamp generation circuit 1002 is configured to use the fine phase signals and the load signal to generate a timestamp signal bus representative of a plurality of timestamp symbols. The timestamp signal bus may be generated centrally and then distributed to one or more TDCs (e.g., across a chip that implements one or more detectors).

A TDC may use the timestamp signal bus to generate a timestamp that corresponds to which a photodetector output pulse is detected by the TDC, thereby indicating an arrival time of a photon detected by a photodetector. For example, as the timestamp signal bus is being provided to the TDC (i.e., as a sequence of timestamp symbols is being delivered to the TDC), the TDC may record a whatever timestamp symbol is present at the TDC when the photodetector output pulse occurs.

Hence, a measurement time window during which a TDC (or a plurality of TDCs) monitors for an occurrence of a photodetector output pulse may be defined by a sweep of a plurality of timestamp symbols that occur during a PLL feedback period. For example, if 128 timestamp symbols are included in the timestamp signal bus per PLL feedback period, the measurement time window may have a duration equal to a duration of the 128 timestamp symbols.

Moreover, a TPSF that is generated based on the recorded timestamp symbols output by one or more TDCs may have a temporal resolution that corresponds to (e.g., that is equal to) the number of timestamp symbols included in a PLL feedback period. For example, if 128 timestamp symbols are included in the timestamp signal bus per PLL feedback period, the TPSF may have a temporal resolution of 128 time bins.

Skew across a conventional timestamp signal bus can cause one or more timestamp symbols in the signal bus to be misinterpreted. Hence, timestamp generation circuit 1002 builds some redundancy into the timestamp signal bus to create a timestamp that is more robust against skew.

For example, as shown, timestamp generation circuit 1002 may include a course counter 1304 configured to be clocked by one of the plurality of fine phase signals and receive a load signal generated by LFSR 902. The load signal is configured to reset course counter 1304 at a beginning of each PLL feedback period. Course counter 1304 is configured to output a course count signal (course_count) comprising a course count up to a maximum value associated with the course counter 1304. Timestamp generation circuit 1002 further includes a first register 1306-1 configured to sample the course count signal to generate a course early signal (course_early) and a second register 1306-2 configured to sample the course early signal to generate a course late signal (course_late). The timestamp signal bus output by timestamp generation circuit 1002 includes a subset of fine phase signals, the course early signal, and the course late signal.

To illustrate, the fine phase signals included in the timestamp signal may be a selection of eight of the sixteen fine phase signals output by VCO 806. Only one of these eight signals changes at a time, and they together are sufficient to uniquely identify sixteen states. The course early and course late signals are both representations of the coarse counter output, but shifted relative to each other such that at all times. In this manner, one of the two coarse buses will be stable. This redundancy in the coarse bus, along with the proper alignment between the fine and coarse, are what provide robustness against distribution skew of the timestamp signal bus.

Course counter 1304 is reset each time the PLL feedback divider load signal is asserted. This keeps the timestamp signal bus synchronized relative to the PLL feedback signal. If this timestamp active region (the region in which it is desirable to have a timestamp) is of shorter duration than the PLL feedback period, then the course counter width can be smaller than the PLL feedback divider width. However, in this case, course counter 1304 must saturate at its maximum count until the load signal is asserted rather than roll over. This design may ensure that any valid timestamp symbol only occurs once within the PLL feedback period. For the case where course counter 1304 saturates, this also means that any timestamps with the coarse counter 1304 at its saturated value (e.g. 7 for a 3-bit counter) may be discarded.

The load signal resets the course counter 1304, then one of the sixteen fine phase signals is selected to clock course counter 1304. The output of course counter 1304 may have some uncertainty or settling time, so the counter output is sampled by register 1306-1 to create signal coarse_early. The coarse_early signal is then resampled by register 1306-2 to generate the coarse_late signal. The counter clock, clk_early, and clk_late signals may be independently chosen from among the sixteen fine signals to ensure proper alignment of the timestamp signal bus. In this example, proper clock phases are chosen to align the coarse_early signal such that its stable region is centered around fine phase signals 0 through 7. Likewise, the coarse_late signal is aligned such that it is stable around fine phase signals 8 though 15.

Figure 14:
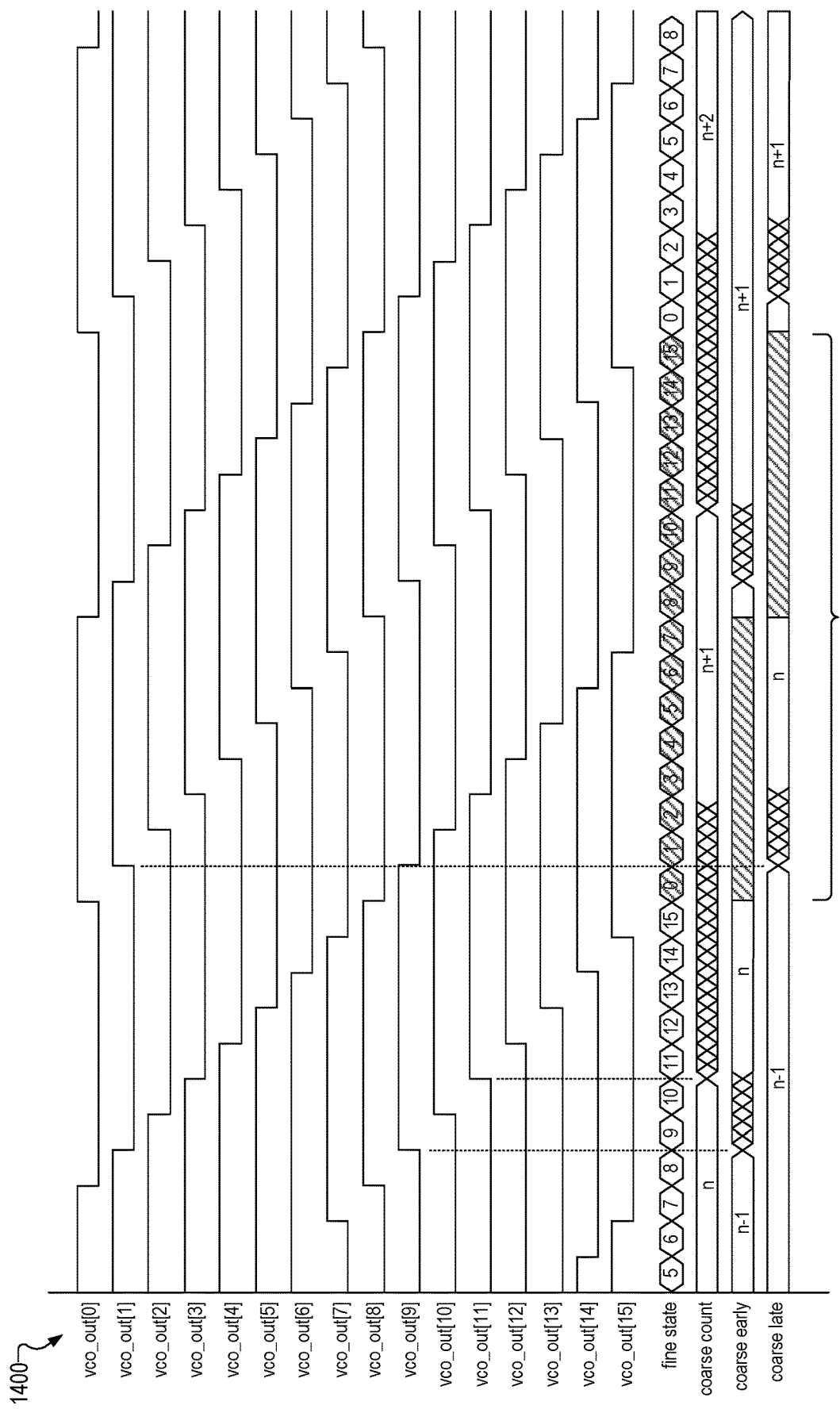
FIG. 14 shows an exemplary timing diagram.

FIG. 14 shows a timing diagram 1400 showing fine phase signals (vco_out), fine phase states (fine state), coarse counter state (course count), and proper alignment of timestamp sub-symbols (fine, coarse_early and coarse_late). Only eight of the vco_out signals are required to correctly identify all sixteen fine phase states (one signal from each of the complementary stages). In this example, the first eight vco_out signals (vco_out[7:0]) are used. The signal marked "fine state" is a representation of the fine phase state, from 0 to 15. A coarse counter, clocked from one of the sixteen vco_out clock phases is reset to zero at the beginning of the repeating measurement interval (period of PLL reference clock), and then counts up, but saturates at its maximum value (for a three bit binary counter it saturates at 7). This coarse counter, which might have a long settling time (represented by Xs), is then resampled twice to generate coarse_early and coarse late signals. These resampled coarse sub-symbols have short settling time (represented by Xs), and are aligned precisely to maximize skew margin between fine, coarse_early, and coarse_late sub-symbols. This alignment is shown with diagonal hash markings. The final timestamp signal bus is the concatenation of coarse_late, coarse_early, and vco_out[7:0]. In this example, the timestamp signal bus is 3+3+8=14 bits wide. For symbol decode, first the fine state is decoded, if fine state is 0 to 7, then the coarse early is used as the coarse value. If fine state is 8 to 15, then coarse late is used.

A TDC that receives the timestamp signal bus may be configured to record a timestamp symbol included in the timestamp signal bus when the TDC detects an occurrence of a photodetector output pulse generated by a photodetector, where the photodetector output pulse indicates that the photodetector has detected a photon from the light pulse after a light pulse is scattered by a target.

In some examples, signal processing circuit 208 may include logic configured to decode a recorded timestamp symbol into a timestamp representative of when the photodetector output pulse is received by the TDC. For example, signal processing circuit 208 may be configured to receive a recorded timestamp symbol, and analyze the eight fine phase signals to identify which of the sixteen possible fine phase states are represented. In some examples, signal processing circuit 208 may use a bubble correction algorithms to do this. If the fine state is between 0 and 7, signal processing circuit 208 may use the coarse_early value. Alternatively, if the fine state is between 8 and 15, signal processing circuit 208 may use the coarse_late value.

Figure 15:
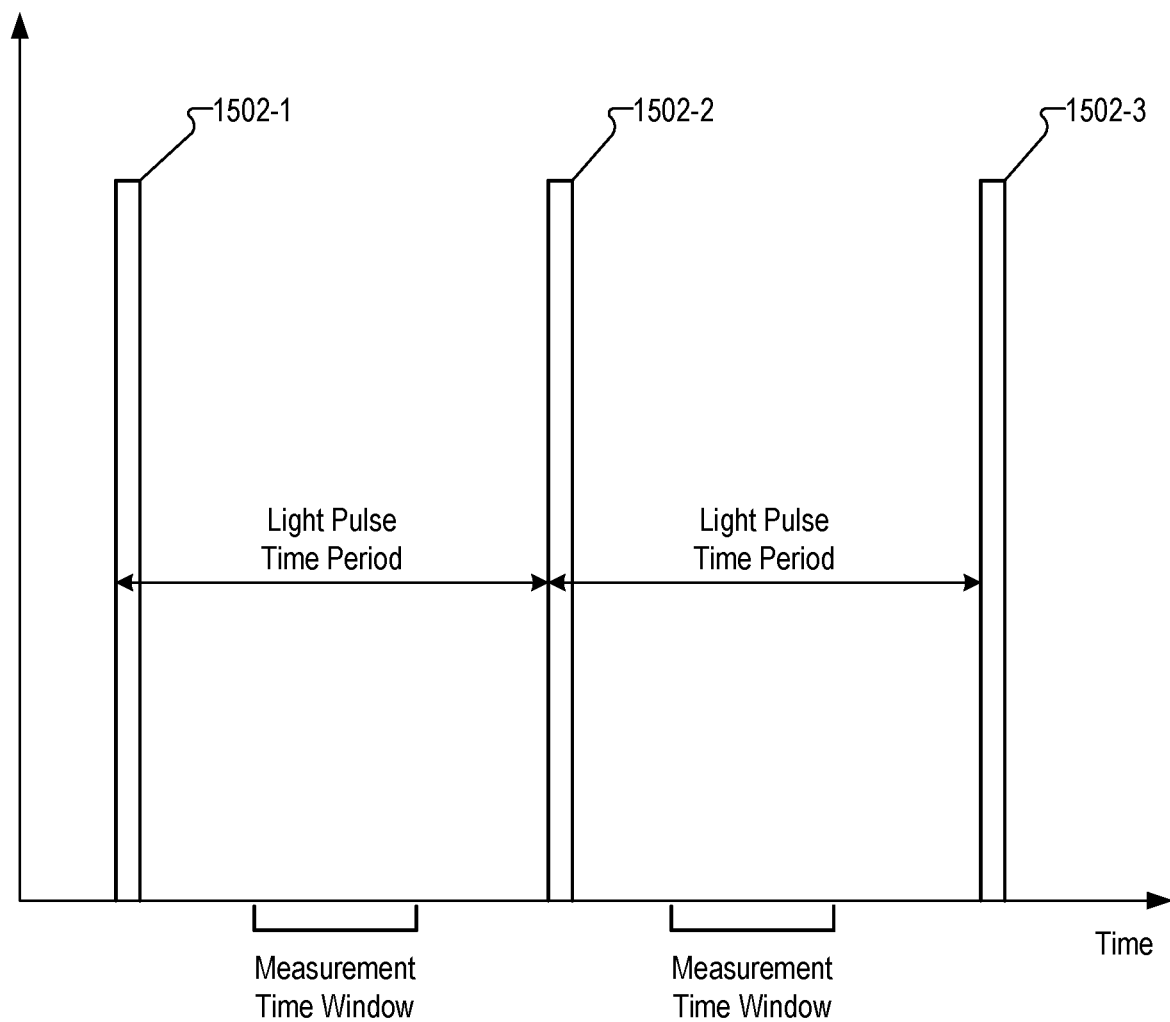
FIG. 15 shows a sequence of light pulses that may be applied to a target.

FIG. 15 shows a sequence of light pulses (e.g., laser pulses) 1502-1 through 1502-3 that may be applied to a target in accordance with the systems, circuits, and methods described herein. While three light pulses 1502 are shown in FIG. 15, it will be recognized that any number of light pulses 1502 may be included in the sequence of light pulses applied to the target as may serve a particular implementation.

As shown, each light pulse 1502 has a corresponding light pulse time period. In the particular example of FIG. 15, the light pulse time period is the time between a rising edge of a light pulse (e.g., light pulse 1502-1) and a rising edge of a subsequent light pulse (e.g., light pulse 1502-2). The light pulse time period may be of any suitable duration (e.g., between 20-40 ns). As shown, each light pulse 1502 may have a relatively low duty cycle (i.e., each light pulse 1502 is only on for a small portion of its corresponding light pulse time period).

As described herein, a photon of a light pulse (e.g., any of light pulses 1502) may be detected by a photodetector after the light pulse is applied to and scattered by a target. When the photon is detected by the photodetector, the photodetector may output a photodetector output pulse. A TDC (e.g., TDC 206) may be configured to monitor for the photodetector output pulse during a measurement time window, as described herein. When the TDC detects the photodetector output pulse, the TDC may record a timestamp symbol, which may be used to generate a TPSF, as described herein. In some examples, an array of TDCs may each monitor for photodetector output pulses during the same measurement time window. In these examples, the timestamp signals recorded by the TDCs may all be used to generate the TPSF.

As shown, the measurement time window is within and shorter in duration than the light pulse time period. This is because photons of interest for a TPSF are not detected by the photodetector until a certain amount of time after the light pulse 1502 is applied and only occur within a relatively short amount of time. For example, an exemplary duration of a measurement time window is between 2-5 ns. Hence, by minimizing the duration of the measurement time window (as opposed to the measurement time window having a duration that spans the entire light pulse time period), power and other resources within optical measurement system 100 may be conserved.

The systems, circuits, and methods described herein are configured to adjust a temporal position of the measurement time window such that the measurement time window is consistently placed with respect to each light pulse 1502. This ensures that the TPSF is accurately generated (i.e., that the samples used to generate the TPSF are placed in the right time bins).

Figure 16:
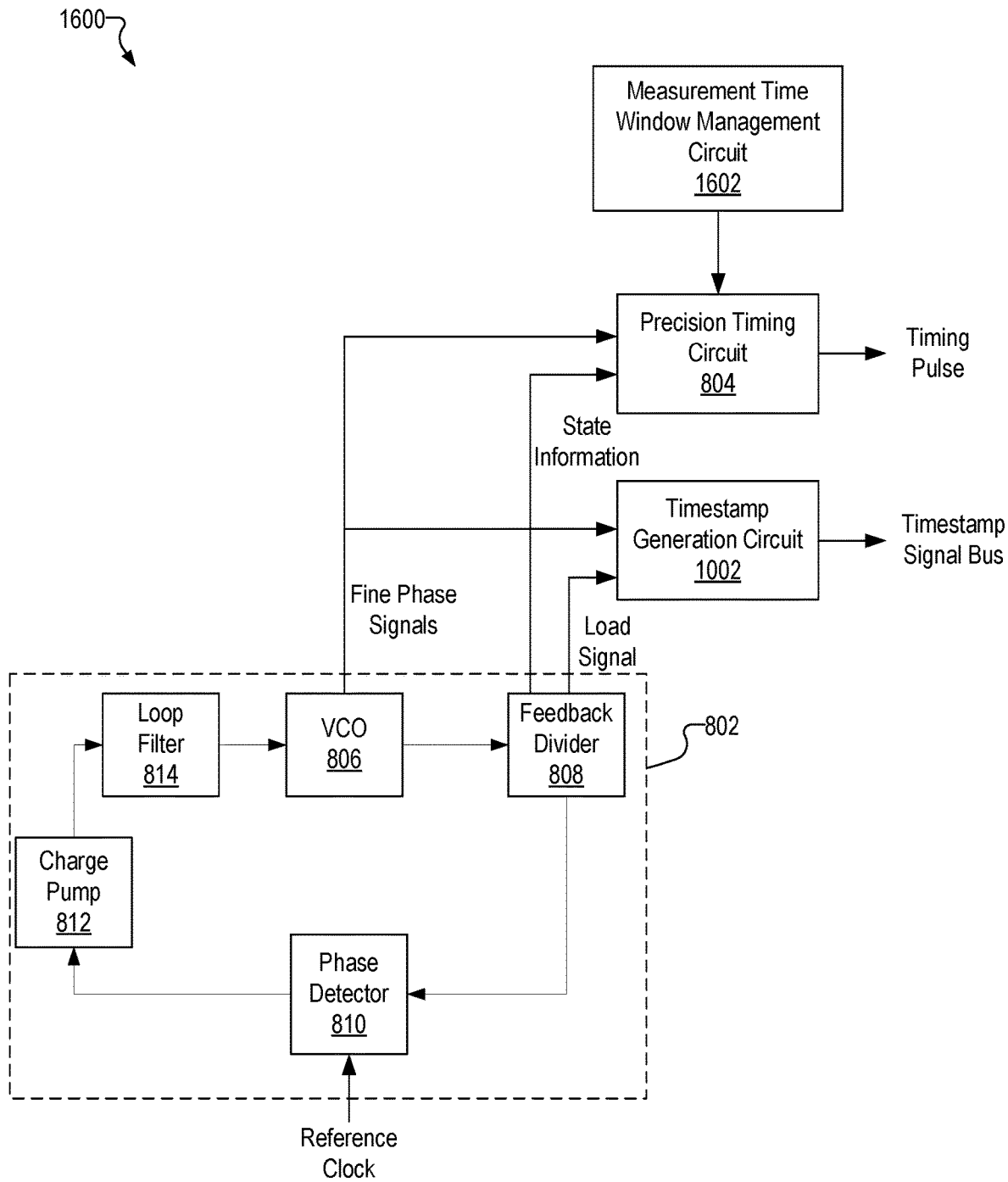
FIG. 16 illustrates an exemplary PLL circuit based architecture.

FIG. 16 illustrates an exemplary PLL circuit based architecture 1600 that may be included within optical measurement system 100 to adjust a measurement time window during which a TDC monitors for an occurrence of a photodetector output pulse. PLL circuit based architecture 1600 is similar to PLL circuit based architecture 1200, except that PLL circuit based architecture 1600 further includes a measurement time window management circuit 1602 ("management circuit 1602") communicatively coupled to precision timing circuit 804.

Management circuit 1602 may be implemented by any suitable combination of components. For example, management circuit 1602 may be implemented by a memory storing instructions and a processor communicatively coupled to the memory and configured to execute the instructions to perform any of the management circuit-related operations described herein. In some examples, management circuit 1602 is implemented by processor 108, controller 112, control circuit 204, and/or signal processing circuit 208.

In some examples, management circuit 1602 may provide a command to precision timing circuit 804 to adjust the measurement time window (e.g., by adjusting a temporal position of the measurement time window and/or by adjusting a duration of the measurement time window). This command may be provided in response to user input, automatically in response to an event occurring within optical measurement system 100, as part of a feedback loop in which the measurement time window is swept across the light pulse time period, and/or for any other reason.

Precision timing circuit 804 may be configured to adjust, based on at least one signal generated within PLL circuit 802, a temporal position of the measurement time window within the light pulse time period. This may be performed in any suitable manner. For example, as described in connection with FIGS. 8-9, VCO 806 may be configured to output a plurality of fine phase signals each having a different phase and feedback divider 808 (e.g., LFSR 902) may be configured to have a plurality of feedback divider states during a PLL feedback period of the PLL circuit 802. Precision timing circuit 804 may be configured to adjust the temporal position of the measurement time window based on one or more of the fine phase signals and one or more signals representative of the feedback divider states.

To illustrate, the measurement time window may be defined as a sweep of a plurality of timestamp symbols included in the timestamp signal bus generated by timestamp generation circuit 1002 that occur during a PLL feedback period, as described herein. The timestamp sweep may be configured to start each time LSFR 902 wraps (or at any other suitable fixed time within a PLL feedback period). As described herein, the output signal of phase intersection block 906-1 may be selectively used as the PLL feedback signal provided to phase detector 810 to adjust the PLL feedback divider phase. This accordingly adjusts when the timestamp sweep occurs, thereby adjusting the temporal position of the measurement time window. Hence, to adjust the temporal position of the measurement time window, management circuit 1602 may adjust the phase of the output signal generated by intersection block 906-1 and direct multiplexer 910 to select the output signal generated by phase intersection block 906-1 to be used as the PLL feedback signal.

Phase intersection block 906-1 may generate the output signal with the programmable phase in any of the ways described herein. For example, as described herein, quadrature clock block 904 may be configured to select, from the plurality of fine phase signals, four fine phase signals that are quadrature shifted from each other for use as quadrature clock signals. Phase intersection block 906-1 may receive the plurality of fine phase signals, receive the quadrature clock signals, receive a programmable target state signal identifying a target feedback divider state included in the plurality of feedback divider states, and receive a programmable target fine phase signal identifying a target fine phase signal included in the plurality of fine phase signals and that, in combination with the target feedback divider state, sets a desired phase of a pulse in the output signal. Phase intersection block 906-1 may also generate a combination match signal when a current feedback divider state matches the target feedback state, use the quadrature clock signals to generate four registered match signals representative of the combination match signal, the four registered match signals quadrature shifted from each other, select a particular match signal from the four registered match signal that is aligned with a pulse included in the target fine phase signal, and input the selected match signal and the target fine phase signal into an AND gate to output the pulse of the output signal at a temporal position that corresponds to the desired phase.

Management circuit 1602 may be further configured to ensure that a measurement time window is consistently placed with respect to each light pulse 1502 that is generated over the course of time in which a TPSF is generated. To do this, management circuit 1602 may be configured to direct precision timing circuit 804 to sweep the measurement time window across the light pulse time period (e.g., some or all of the light pulse time period) while the sequence of light pulses are being generated. This sweeping may result in a TPSF being generated based on timestamp symbols recorded by one or more TDCs while the measurement time window is being swept. Management circuit 1602 may be further configured to determine a property of the TPSF and identify, based on the property of the TPSF, a temporal location within the light pulse time period (e.g., a temporal location that corresponds to the determined property of the TPSF). Management circuit 1602 may then direct precision timing circuit 804 to adjust the temporal position of the measurement time window to align a particular time bin within the measurement time window with the temporal location within the light pulse time period. This process may be periodically repeated to ensure that the measurement time window is consistently placed over time.

The TPSF property used in this process may be any suitable property or metric as may serve a particular implementation. For example, the property may be a peak value of the TPSF, a full width at half maximum metric associated with the TPSF, a center of mass associated with the TPSF, a fitting metric associated with the TPSF, and/or a cross-correlation metric associated with the TPSF.

Figure 17A:
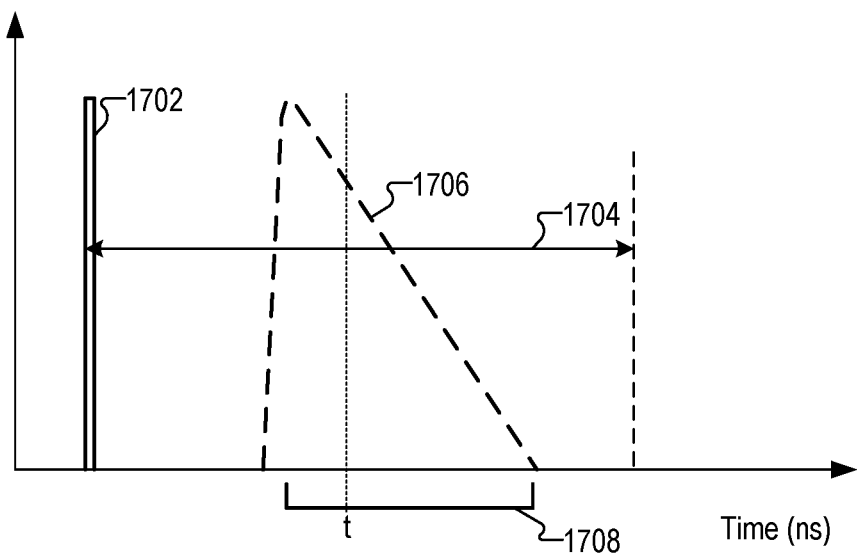
FIGS. 17A-17B illustrate an example of aligning a measurement time window.
Figure 17B:
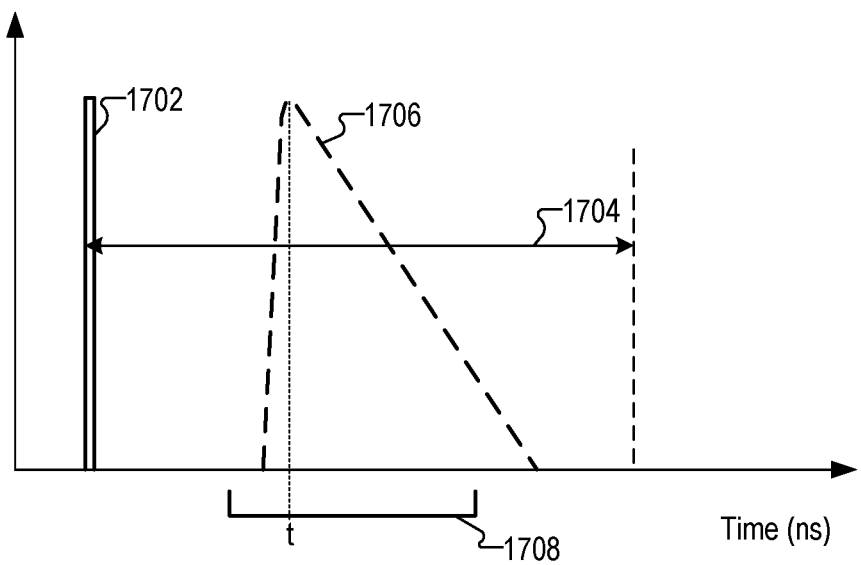

FIGS. 17A-17B illustrate an example in which the determined property is a peak value of the TPSF. In FIGS. 17A-17B, light pulses 1702 are directed to a target, which scatters the light pulses 1702 before photons in the light pulses 1702 are detected by one or more photodetectors. While a single pulse is shown in FIGS. 17A-17B, it will be recognized that this single pulse represents multiple light pulses 1702 that are sequentially applied and that each have a light pulse time period 1704.

FIGS. 17A-17B also show an exemplary TPSF 1706 generated based on timestamps recorded by one or more TDCs as the light pulses 1702 are applied over time. TPSF 1706 is illustrated in dashed lines to connote that TPSF 1706 is measured by aggregating a total number of photons detected in each time bin that follows an occurrence of each light pulse 1702.

In some examples, after a chip on which the photodetectors and TDCs are located starts up, a measurement time window 1708 is positioned at a random position due to the random phase that PLL locks to. As shown in FIG. 17A, this means that a reference time t within the measurement time window 1708 may be positioned at a random time bin with respect to the TPSF 1706. The reference time t may be any fixed temporal position within measurement time window 1708.

Accordingly, management circuit 1602 may direct precision timing circuit 804 to sweep the measurement time window 1708 across the light pulse time period 1704 to identify a peak value of TPSF 1706. This sweep may be performed by adjusting the temporal position of measurement time window 1708 across the light pulse time period 1704 over a sequence of PLL feedback periods. The sweep may be performed with any suitable amount of time granularity. As the measurement time window 1708 is swept across the light pulse time period 1704, management circuit 1602 analyzes the TPSF 1706 to identify a peak value of TPSF 1706. This may be performed in any suitable manner.

Management circuit 1602 may determine a temporal location within light pulse time period 1704 that corresponds to the identified peak value. This may be performed in any suitable manner. Once this temporal location has been determined, as shown in FIG. 17B, management circuit 1602 may direct precision timing circuit 804 to move measurement time window 1708 so that the reference time t is aligned with the peak value of TPSF 1706. In this manner, the management circuit 1602 may ensure that the measurement time window 1708 is consistently aligned during TPSF generation.

The measurement time window may be adjusted at any suitable time during operation of optical measurement system 100. For example, management circuit 1602 may receive a command to perform a calibration of one or more TDCs (e.g., at system startup and/or at any other time), and, in response, perform the measurement time window adjustment operations described herein. This calibration may be performed periodically over time to ensure that the measurement time window is correctly positioned.

Figure 18:
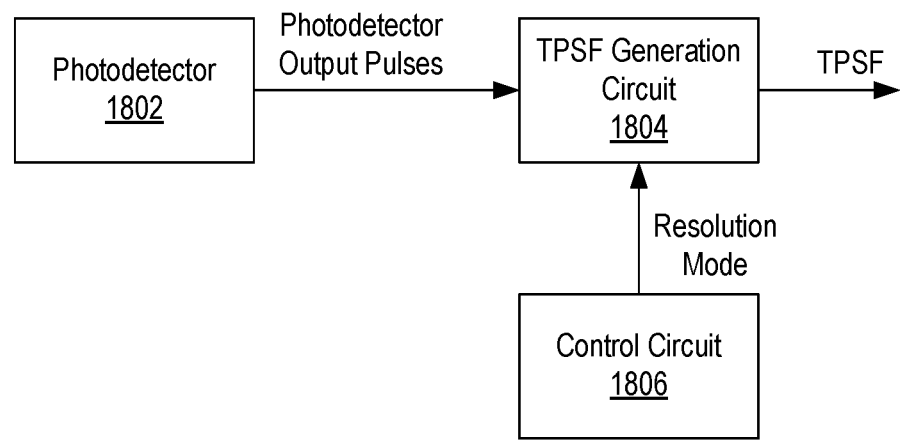
FIG. 18 illustrates an exemplary system for generating a TPSF and controlling a temporal resolution of the TPSF.

FIG. 18 illustrates an exemplary system 1800 for generating a TPSF and controlling a temporal resolution of the TPSF. As shown, system 1800 includes a photodetector 1802, a TPSF generation circuit 1804, and a control circuit 1806. Additional or alternative components may be included in system 1800 as may serve a particular implementation.

Photodetector 1802 may be similar to any of the photodetectors described herein, and may be configured to generate a plurality of photodetector output pulses over time as a plurality of light pulses are applied to and scattered by a target. As described herein, each photodetector output pulse is generated when photodetector 1802 detects a photon from one of the light pulses that is scattered by the target. In some examples, photodetector 1802 is implemented by a plurality of photodetectors each configured to generate photodetector output pulses.

TPSF generation circuit 1804 may be configured to generate, based on the photodetector output pulses, a TPSF representative of a light pulse response of the target. TPSF generation circuit 1804 may be implemented by any of the components described herein. For example, TPSF generation circuit 1804 may be implemented by one or more TDCs and a signal processing circuit communicatively coupled to the one or more TDCs. The one or more TDCs may be similar to any of the TDCs described herein, and the signal processing circuit may be similar to any of the signal processing circuits described herein. The one or more TDCs may be configured to monitor for the photodetector output pulses, record timestamp symbols corresponding to occurrences of the photodetector output pulses, and provide one or more output signals representative of the recorded timestamp symbols. The signal processing circuit is configured to generate the TPSF based on the one or more output signals provided by the one or more TDCs. In some examples, TPSF generation circuit 1804 may further include a PLL circuit and a timestamp generation circuit, as described herein.

Control circuit 1806 is communicatively coupled to TPSF generation circuit 1804 and configured to control a temporal resolution of the TPSF generated by TPSF generation circuit 1804. Control circuit 1806 may be implemented by any suitable combination of components. For example, control circuit 1806 may be implemented by a memory storing instructions and a processor communicatively coupled to the memory and configured to execute the instructions to perform any of the control circuit-related operations described herein. In some examples, control circuit 1806 is implemented by processor 108, controller 112, control circuit 204, and/or signal processing circuit 208.

As shown, control circuit 1806 may provide a control signal ("resolution mode") to TPSF generation circuit 1804 that directs TPSF generation circuit 1804 to selectively operate in one of a plurality of different resolution modes. For example, control circuit 1806 may be configured to direct TPSF generation circuit 1804 to selectively operate in a first resolution mode in which a temporal resolution of the TPSF is a first temporal resolution value or in a second resolution mode in which the temporal resolution of the TPSF is a second temporal resolution value different than the first temporal resolution value.

Figure 19A:
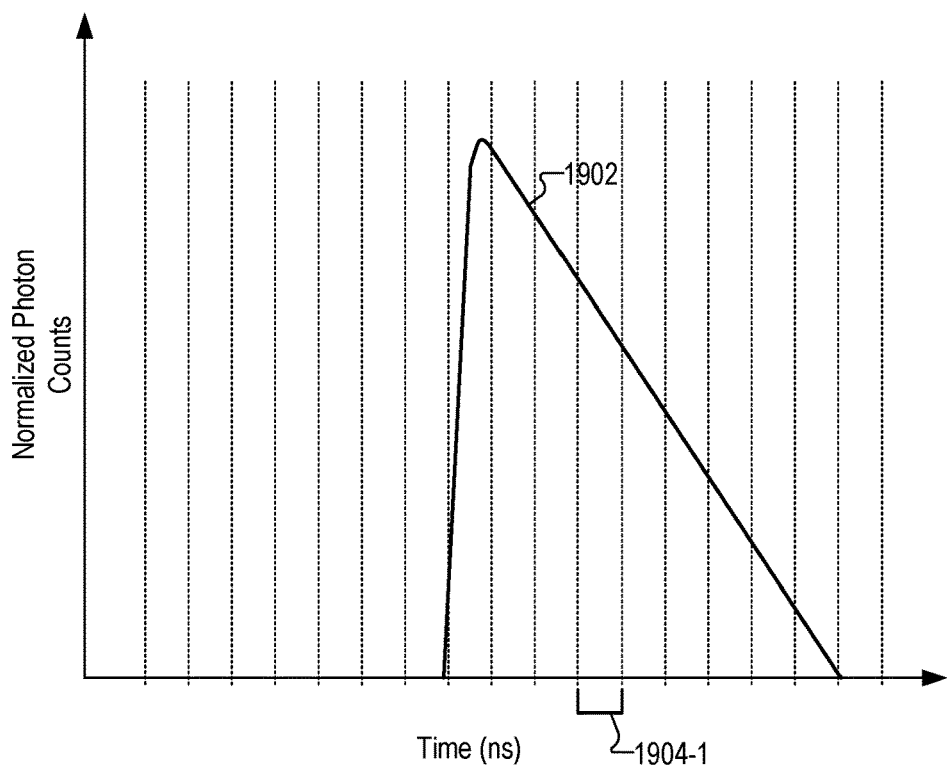
FIGS. 19A-19B show TPSFs with different temporal resolutions.

For example, FIG. 19A shows that TPSF generation circuit 1804 may initially operate in a first resolution mode in which TPSF generation circuit 1804 generates a TPSF 1902 that has a temporal resolution of a first temporal resolution value. In this first resolution mode, each time bin (e.g., time bin 1904-1) of the TPSF 1902 is relatively short in duration. For example, in this first resolution mode, the TPSF 1902 may be 128 time bins wide, where each time bin has a duration of 50 ps or less.

While TPSF generation circuit 1804 is operating in the first resolution mode (or at any other time), control circuit 1806 may receive a command (e.g., from another component within optical measurement system 100 and/or from a user) indicating that TPSF generation circuit 1804 is to switch to operating in a second resolution mode. In response to receiving the command, control circuit 1806 may provide TPSF generation circuit 1804 with a control signal that directs TPSF generation circuit 1804 to switch to operating in the second resolution mode. In alternative embodiments, control circuit 1806 may direct TPSF generation circuit 1804 to switch to the second resolution mode without receiving any command to do so.

Figure 19B:
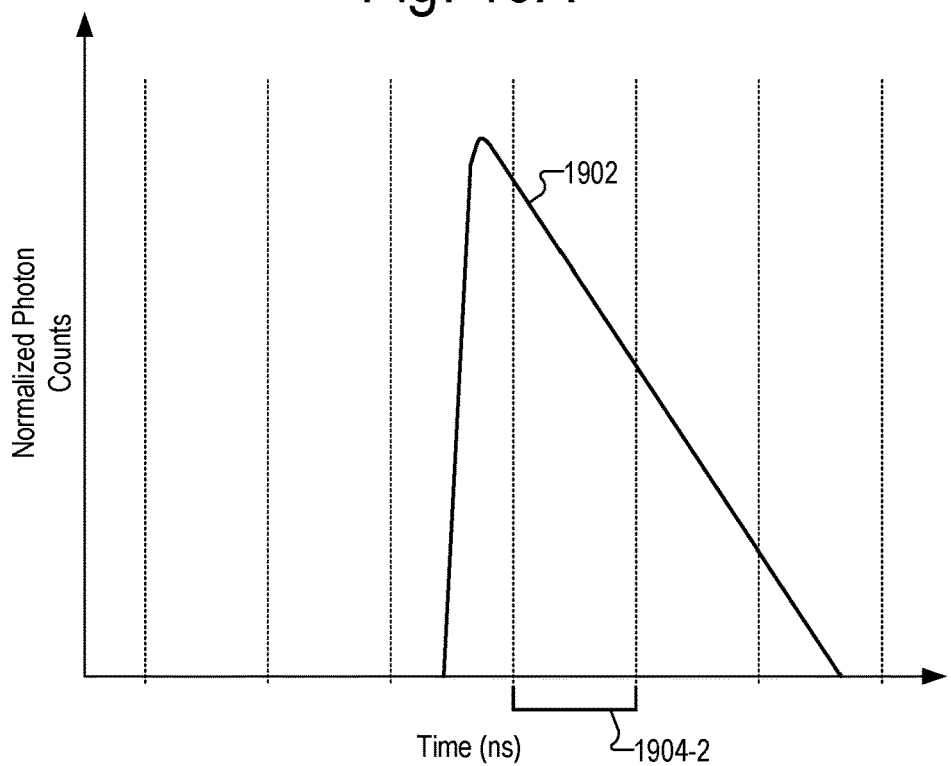

FIG. 19B shows TPSF 1902 generated while TPSF generation circuit 1804 operates in the second resolution mode. As shown, each time bin (e.g., time bin 1904-2) of the TPSF 1902 in this second resolution mode is relatively long in duration. For example, in this second resolution mode, the TPSF 1902 may be 32 time bins wide, where each time bin has a duration of 200 ps or more).

Selectively generating TPSFs with different temporal resolutions may be beneficial for a number of different reasons. For example, TPSF generation circuit 1804 may operate in a relatively high resolution mode (i.e., where the temporal resolution of the TPSF is relatively high) during calibration of one or more TDCs, while a temporal position of a measurement time window is being adjusted or aligned (as described herein), and/or in other scenarios where high resolution TPSFs are desirable. TPSF generation circuit 1804 may alternatively operate in a relatively low resolution mode (i.e., where the temporal resolution of the TPSF is relatively low) during scenarios in which high resolution TPSFs may not be necessary. For example, TPSF generation circuit 1804 may operate in the relatively low resolution mode when generating a TPSF that is to be used for some types of neuroscience applications, after a TDC calibration procedure has been performed, and/or in any other scenario as may serve a particular implementation.

Figure 20:
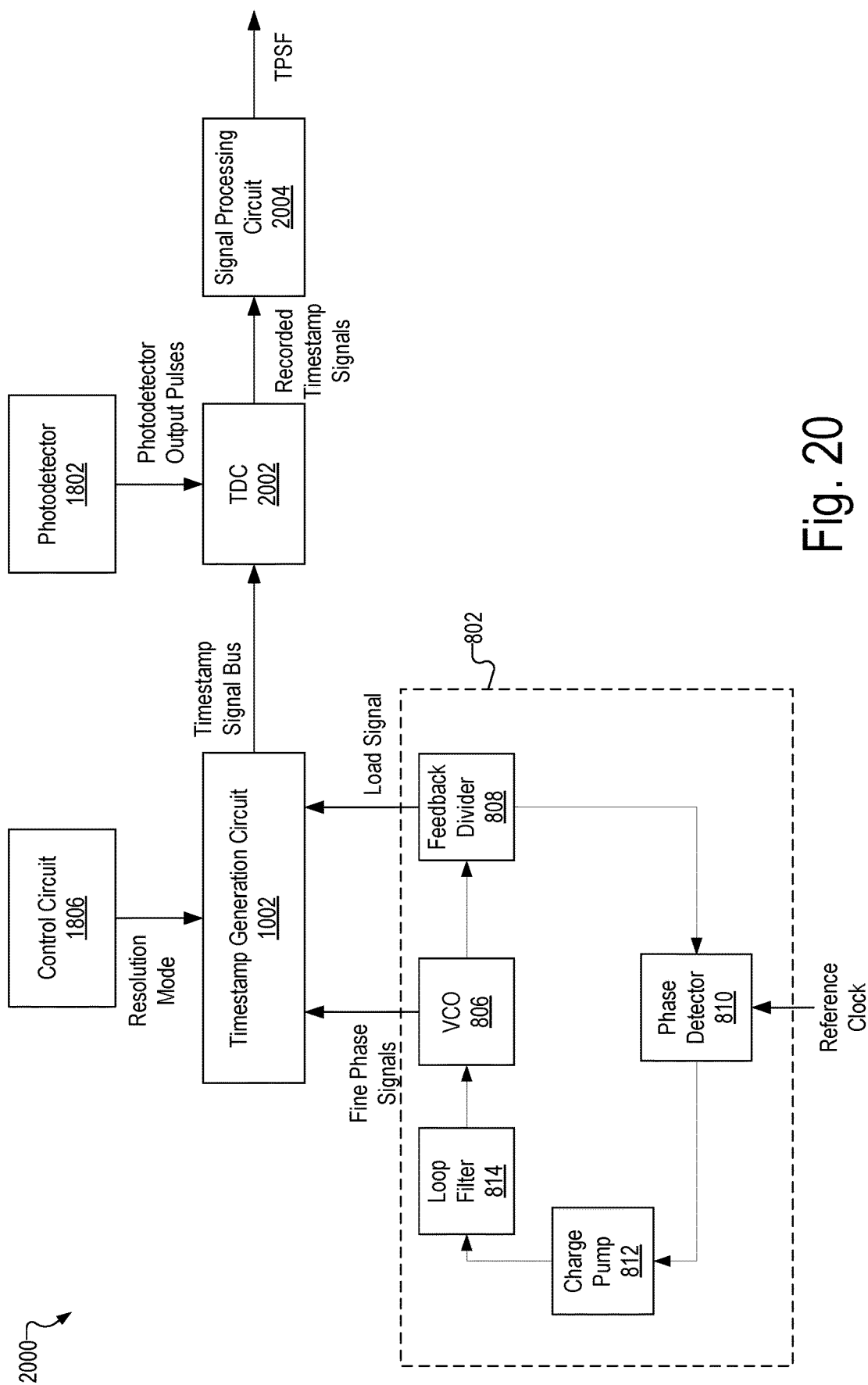
FIGS. 20-21 illustrate exemplary PLL circuit based architectures.

FIG. 20 shows an exemplary configuration 2000 in which an exemplary PLL circuit based implementation of TPSF generation circuit 1804 is illustrated. In configuration 2000, TPSF generation circuit 1804 is implemented by a TDC 2002, a signal processing circuit 2004, PLL circuit 802, and timestamp generation circuit 1002.

TDC 2002 is configured to monitor for photodetector output pulses generated by photodetector 1802 and record timestamp symbols corresponding to occurrences of the photodetector output pulses, as described herein. As shown, TDC 2002 provides an output signal representative of the recorded timestamp symbols to signal processing circuit 2004, which is configured to generate a TPSF based on the output signal.

In the example of FIG. 20, the timestamp symbols recorded by TDC 2002 are included in a timestamp signal bus output by timestamp generation circuit 1002, which may generate the timestamp signal bus in any of the ways described herein. In some examples, the timestamp signal bus includes a programmable number of timestamp symbols per PLL feedback period of PLL circuit 802. This programmable number of timestamp symbols may define the temporal resolution of the TPSF. For example, if 128 timestamp symbols per PLL feedback period are included in the timestamp signal bus, the temporal resolution of the TPSF may be 128 time bins per measurement time window. Alternatively, if 32 timestamp symbols per PLL feedback period are included in the timestamp signal bus, the temporal resolution of the TPSF may be 32 time bins per measurement time window.

As shown, control circuit 1806 may transmit a command (e.g., the resolution mode control signal) to timestamp generation circuit 1002. This command may set the programmable number of timestamp symbols per PLL feedback period that are included in the timestamp signal bus to a first value to cause TPSF generation circuit 1804 to operate in a first resolution mode. The command may alternatively set the programmable number of timestamp symbols per PLL feedback period that are included in the timestamp signal bus to a second value different than the first value to cause TPSF generation circuit 1804 to operate in a second resolution mode.

Timestamp generation circuit 1002 may selectively change the number of timestamp symbols per PLL feedback period that are included in the timestamp signal bus in any suitable manner. For example, as described herein, timestamp generation circuit 1002 may generate the timestamp signal bus based on a subset of fine phase signals generated by VCO 806. In some examples, a total number of fine phase signals included in the subset of fine phase signals may be changed to selectively change the number of timestamp symbols per PLL feedback period that are included in the timestamp signal bus. For example, in the first resolution mode, a total number of fine phase signals included in the subset of the fine phase signals used by timestamp generation circuit 1002 to generate the timestamp signal bus may be equal to a first value. In contrast, in the second resolution mode, the total number of fine phase signals included in the subset of the fine phase signals used by timestamp generation circuit 1002 to generate the timestamp signal bus may be equal to a second value that is different than the first value.

Figure 21:
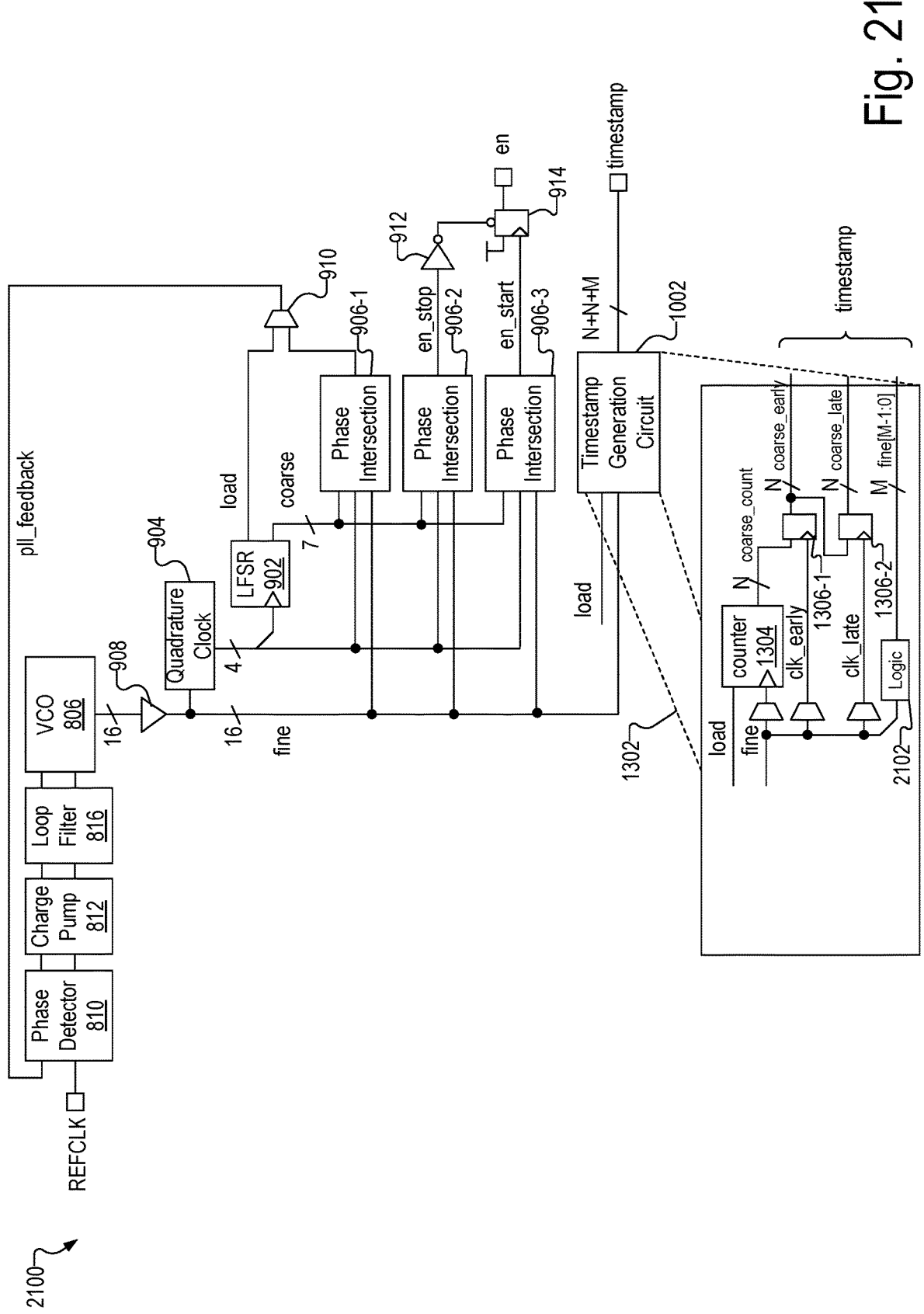

FIG. 21 shows an exemplary implementation 2100 of PLL circuit based architecture 1200. Implementation 2100 is similar to implementation 1300 described in connection with FIG. 13, but also includes logic 2102 within timestamp generation circuit 1002 configured to facilitate selective use of different numbers of fine phase signals to generate the timestamp signal bus.

As shown, the fine phase signals (fine) output by VCO 806 may be input into logic 2102. Logic 2102 may be configured to select M of the fine phase signals for inclusion in the timestamp bus, where M is programmable. As shown, the M fine phase signals may be included in the timestamp signal bus output by timestamp generation circuit 1002. Logic 2102 may include any suitable selection logic as may serve a particular implementation.

By way of illustration, in response to a command for TPSF generation circuit 1804 to operate in a relatively high resolution mode, logic 2102 may be configured to set M to eight in order to select eight fine phase signals for inclusion in the timestamp signal bus. The eight fine phase signals may define sixteen fine phase states, as described herein. These sixteen fine phase states, in combination with a course counter output that counts to eight, may result in 16*8=128 timestamp symbols per PLL period being included in the timestamp signal bus. This, in turn, results in a temporal resolution of the TPSF being 128 time bins per measurement time window.

Continuing with this example, in response to a command for TPSF generation circuit 1804 to operate in a relatively low resolution mode, logic 2102 may be configured to set M to two in order to select only two fine phase signals for inclusion in the timestamp signal bus. The two fine phase signals may define four fine phase states, as described herein. These four fine phase states, in combination with the course counter output that counts to eight, may result in 4*8=32 timestamp symbols per PLL period being included in the timestamp signal bus. This, in turn, results in a temporal resolution of the TPSF being 32 time bins per measurement time window.

As mentioned, optical measurement system 100 may be at least partially wearable by a user. For example, optical measurement system 100 may be implemented by a wearable device configured to be worn by a user (e.g., a head-mountable component configured to be worn on a head of the user). The wearable device may include one or more photodetectors and/or any of the other components described herein. In some examples, one or more components (e.g., processor 108, controller 112, etc.) may not be included in the wearable device and/or included in a separate wearable device than the wearable device in which the one or more photodetectors are included. In these examples, one or more communication interfaces (e.g., cables, wireless interfaces, etc.) may be used to facilitate communication between the various components.

FIGS. 22-27 illustrate embodiments of a wearable device 2200 that includes elements of the optical detection systems described herein. In particular, the wearable devices 2200 include a plurality of modules 2202, similar to the modules shown in FIG. 6 as described herein. For example, each module 2202 includes a source 604 and a plurality of detectors 606 (e.g., detectors 606-1 through 606-6). Source 604 may be implemented by one or more light sources similar to light source 110. Each detector 606 may implement or be similar to detector 104 and may include a plurality of photodetectors. The wearable devices 2200 may each also include a controller (e.g., controller 112) and a processor (e.g., processor 108) and/or be communicatively connected to a controller and processor. In general, wearable device 2200 may be implemented by any suitable headgear and/or clothing article configured to be worn by a user. The headgear and/or clothing article may include batteries, cables, and/or other peripherals for the components of the optical measurement systems described herein.

Figure 22:
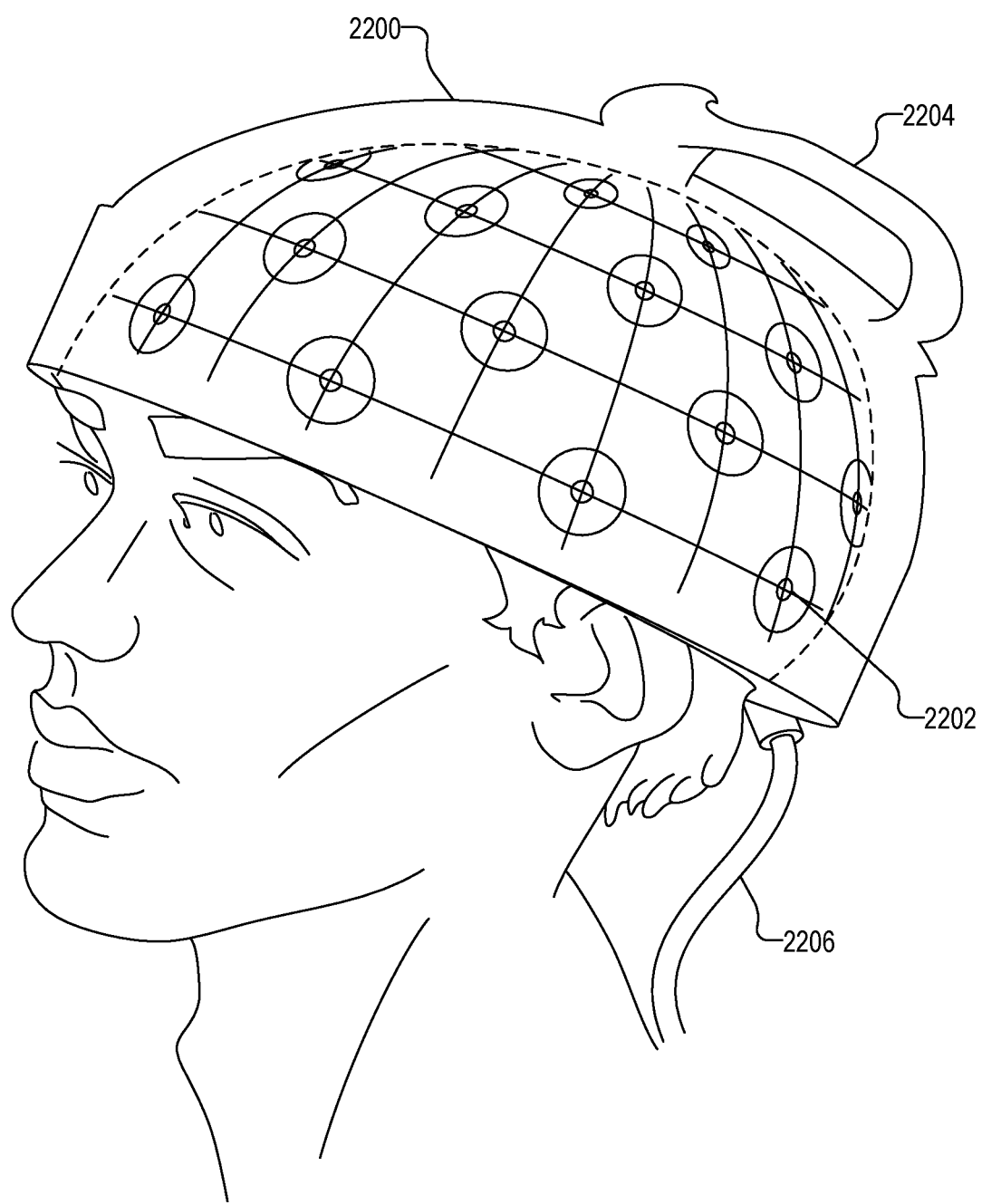
FIGS. 22-27 illustrate embodiments of a wearable device that includes elements of the optical detection systems described herein.
Figure 23:
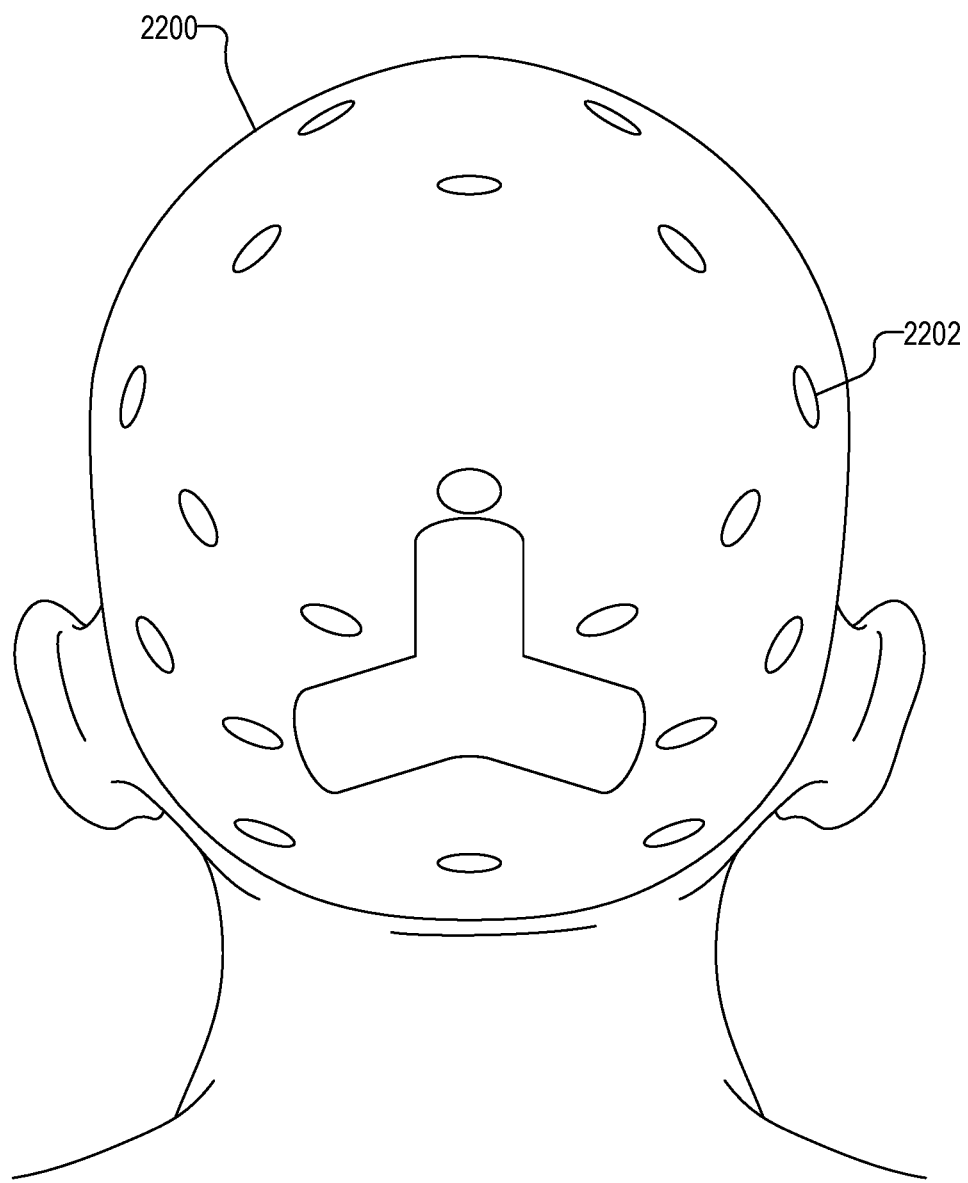
Figure 24:
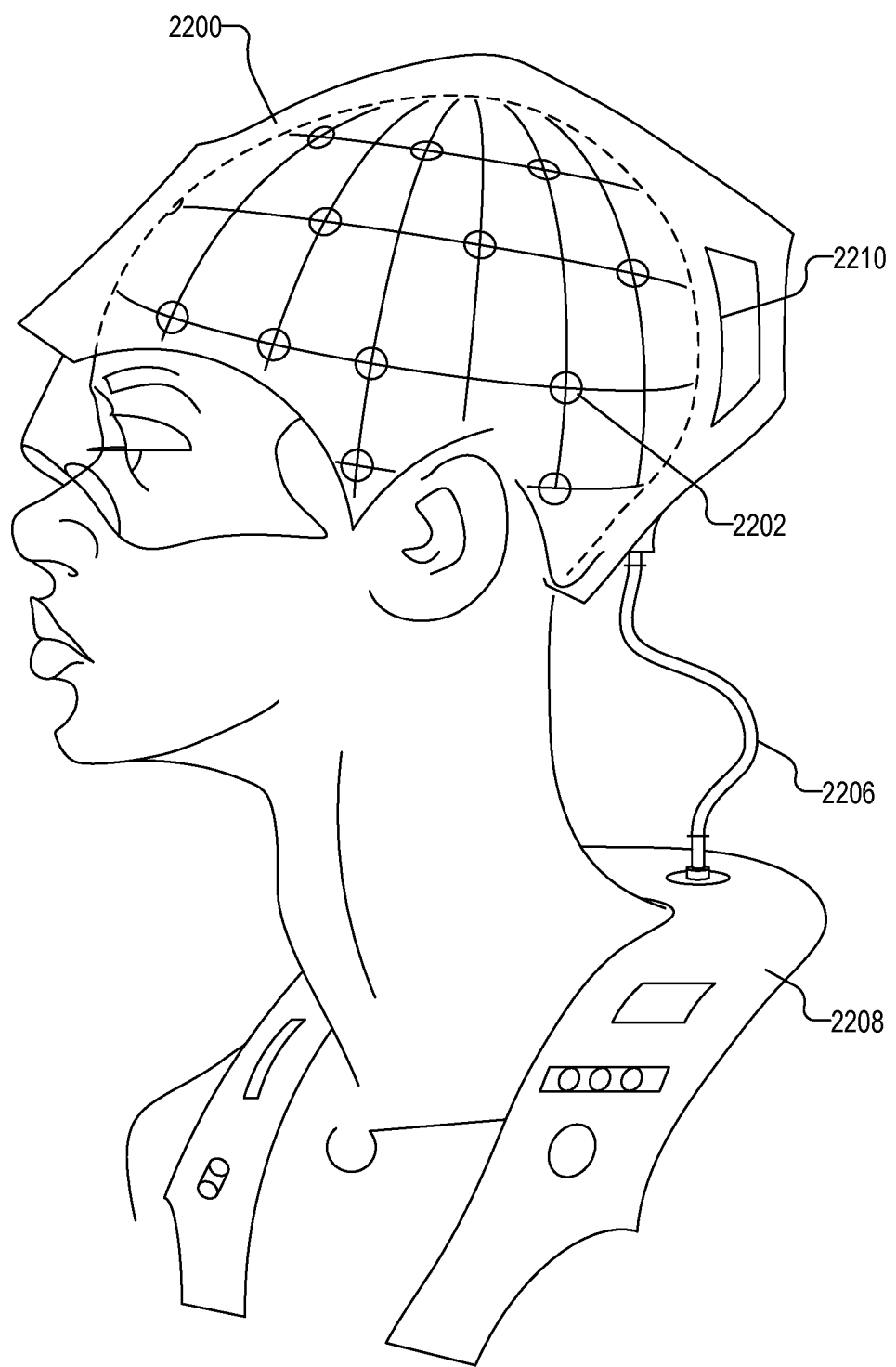

FIG. 22 illustrates an embodiment of a wearable device 2200 in the form of a helmet with a handle 2204. A cable 2206 extends from the wearable device 2200 for attachment to a battery or hub (with components such as a processor or the like). FIG. 23 illustrates another embodiment of a wearable device 2200 in the form of a helmet showing a back view. FIG. 24 illustrates a third embodiment of a wearable device 2200 in the form of a helmet with the cable 2206 leading to a wearable garment 2208 (such as a vest or partial vest) that can include a battery or a hub. Alternatively or additionally, the wearable device 2200 can include a crest 2210 or other protrusion for placement of the hub or battery.

Figure 25:
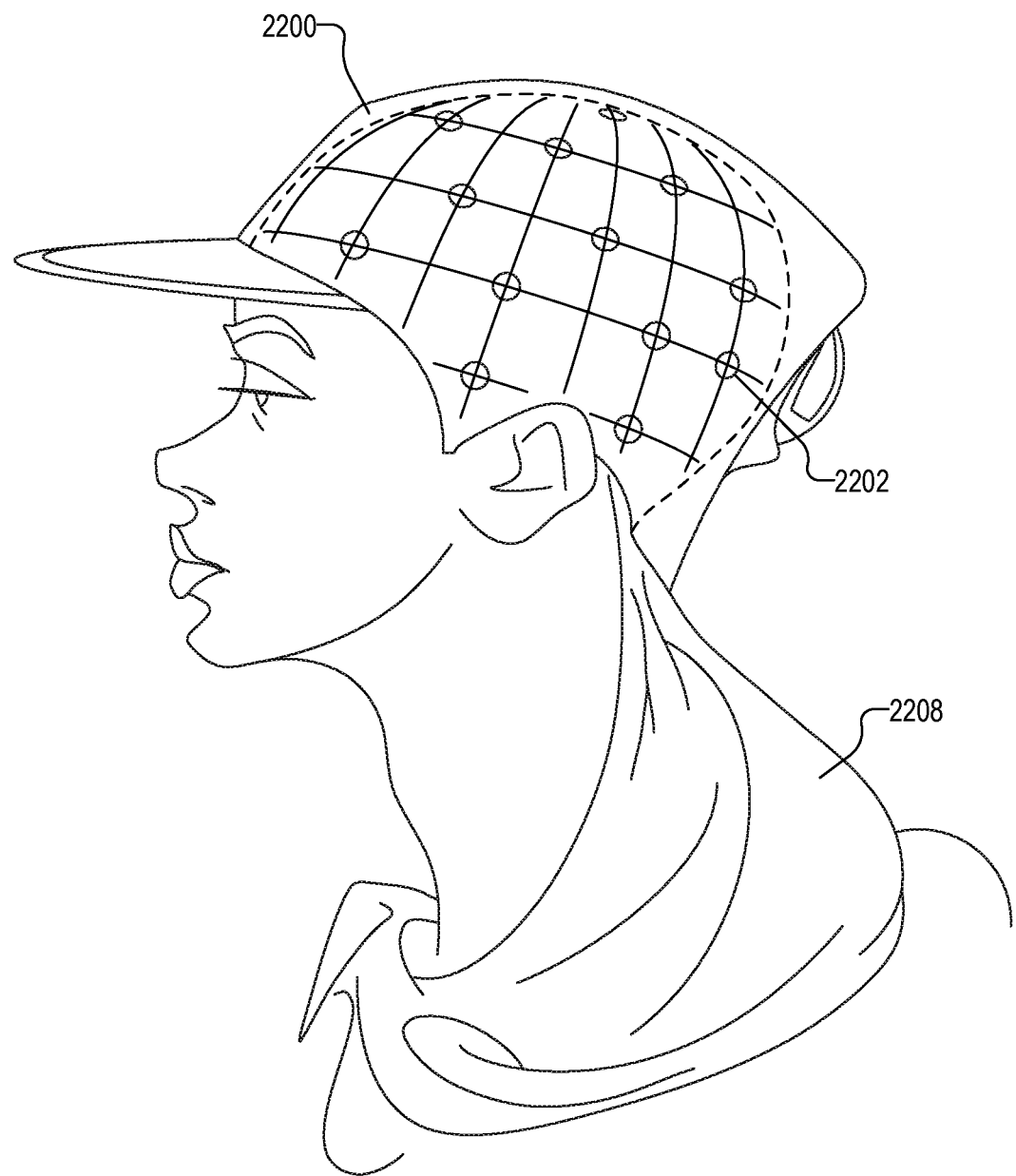
Figure 26:
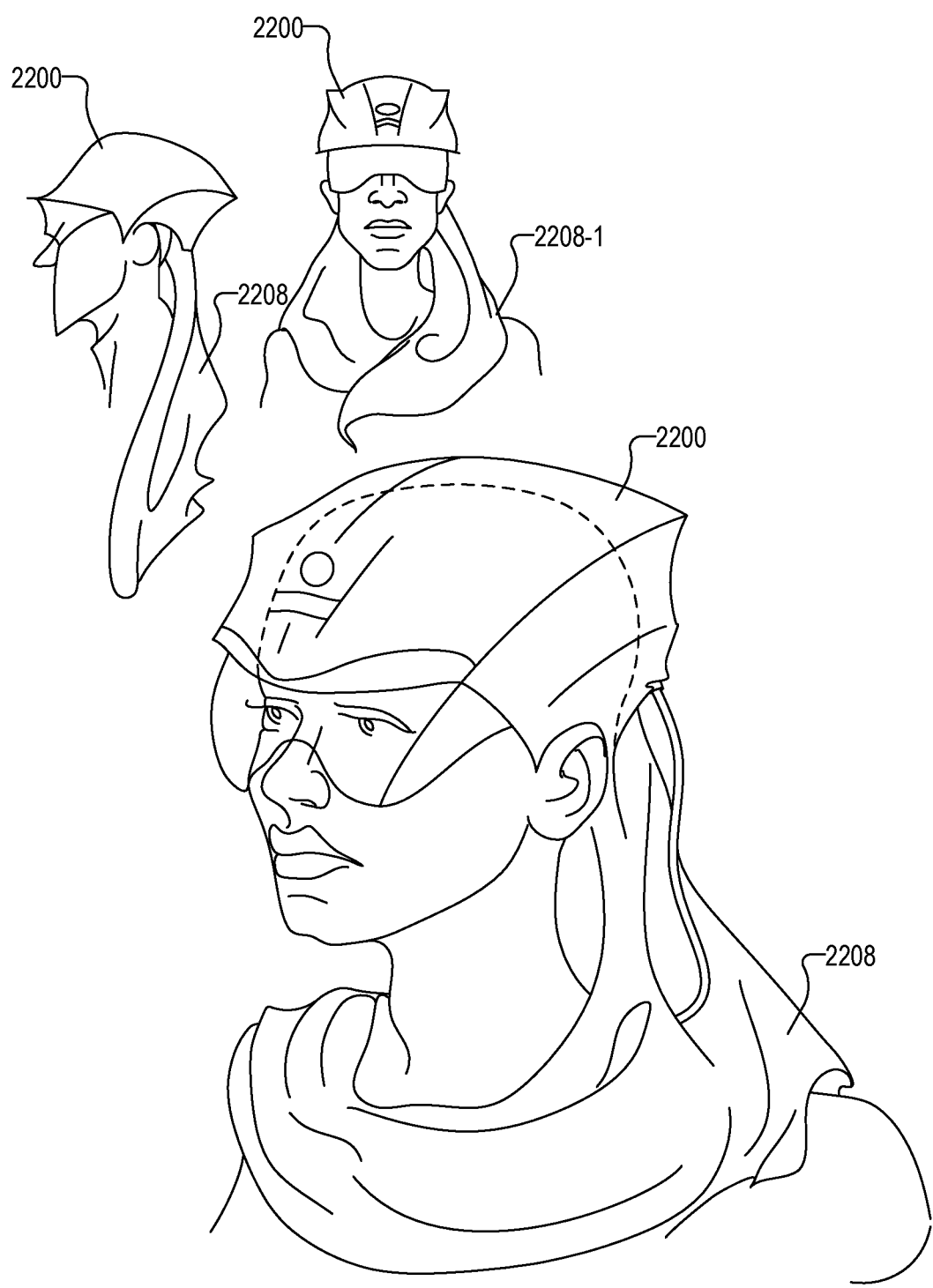
Figure 27:
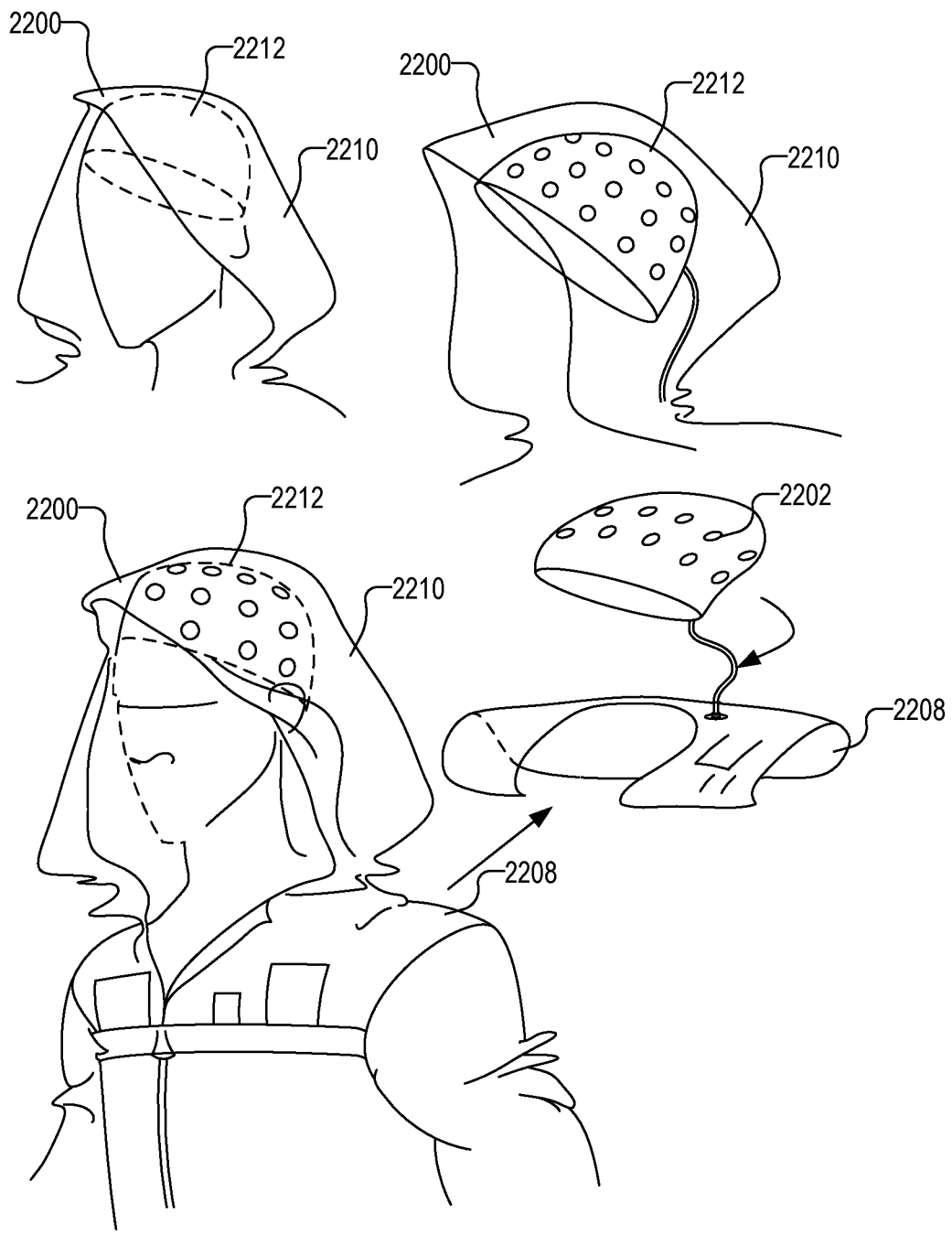

FIG. 25 illustrates another embodiment of a wearable device 2200 in the form of a cap with a wearable garment 2208 in the form of a scarf that may contain or conceal a cable, battery, and/or hub. FIG. 26 illustrates additional embodiments of a wearable device 2200 in the form of a helmet with a one-piece scarf 2208 or two-piece scarf 2208-1. FIG. 27 illustrates an embodiment of a wearable device 2200 that includes a hood 2210 and a beanie 2212 which contains the modules 2202, as well as a wearable garment 2208 that may contain a battery or hub.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 28:
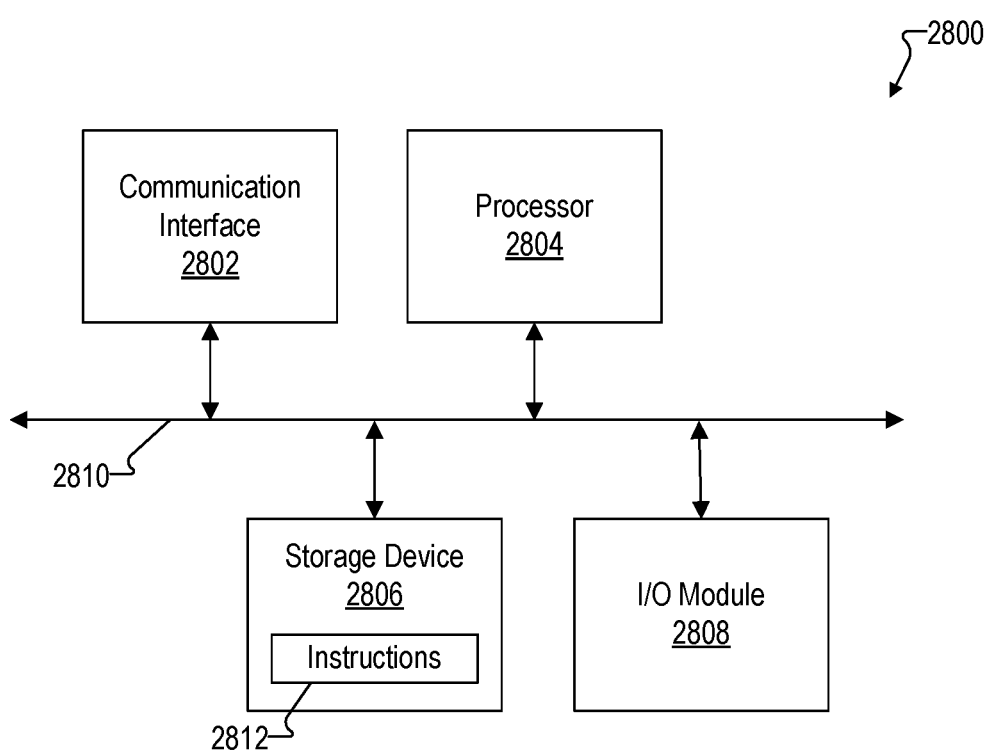
FIG. 28 illustrates an exemplary computing device.

FIG. 28 illustrates an exemplary computing device 2800 that may be specifically configured to perform one or more of the processes described herein. Any of the systems, units, computing devices, and/or other components described herein may be implemented by computing device 2800.

As shown in FIG. 28, computing device 2800 may include a communication interface 2802, a processor 2804, a storage device 2806, and an input/output ("I/O") module 2808 communicatively connected one to another via a communication infrastructure 2810. While an exemplary computing device 2800 is shown in FIG. 28, the components illustrated in FIG. 28 are not intended to be limiting. Additional or alternative components may be used in other embodiments. Components of computing device 2800 shown in FIG. 28 will now be described in additional detail.

Communication interface 2802 may be configured to communicate with one or more computing devices. Examples of communication interface 2802 include, without limitation, a wired network interface (such as a network interface card), a wireless network interface (such as a wireless network interface card), a modem, an audio/video connection, and any other suitable interface.

Processor 2804 generally represents any type or form of processing unit capable of processing data and/or interpreting, executing, and/or directing execution of one or more of the instructions, processes, and/or operations described herein. Processor 2804 may perform operations by executing computer-executable instructions 2812 (e.g., an application, software, code, and/or other executable data instance) stored in storage device 2806.

Storage device 2806 may include one or more data storage media, devices, or configurations and may employ any type, form, and combination of data storage media and/or device. For example, storage device 2806 may include, but is not limited to, any combination of the non-volatile media and/or volatile media described herein. Electronic data, including data described herein, may be temporarily and/or permanently stored in storage device 2806. For example, data representative of computer-executable instructions 2812 configured to direct processor 2804 to perform any of the operations described herein may be stored within storage device 2806. In some examples, data may be arranged in one or more databases residing within storage device 2806.

I/O module 2808 may include one or more I/O modules configured to receive user input and provide user output. I/O module 2808 may include any hardware, firmware, software, or combination thereof supportive of input and output capabilities. For example, I/O module 2808 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 2808 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 2808 is configured to provide graphical data to a display for presentation to a user. The graphical data may be representative of one or more graphical user interfaces and/or any other graphical content as may serve a particular implementation.

Figure 29:
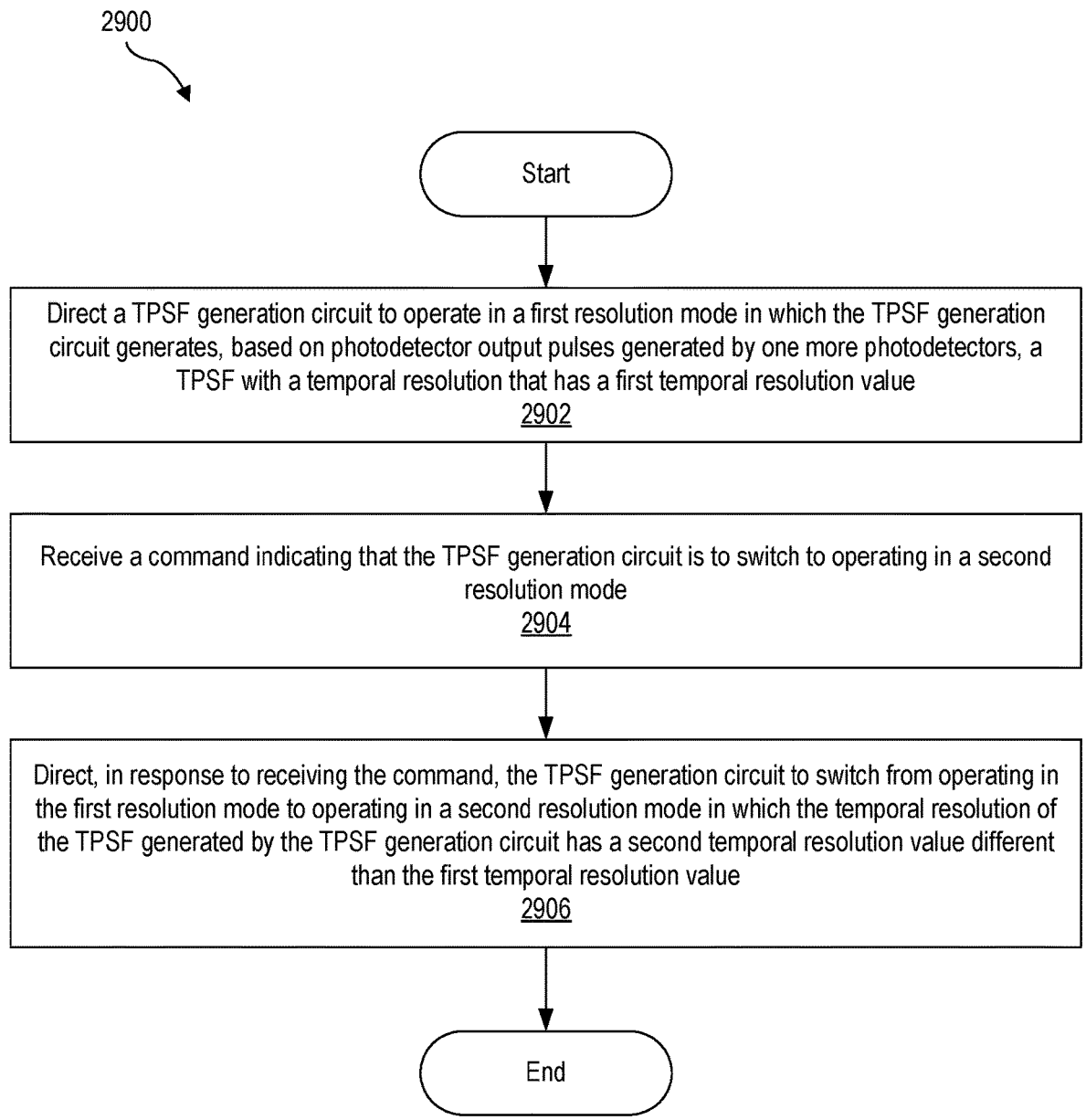
FIG. 29 illustrates an exemplary method.

FIG. 29 illustrates an exemplary method 2900 that may be performed control circuit by control circuit 1806 and/or any implementation thereof. While FIG. 29 illustrates exemplary operations according to one embodiment, other embodiments may omit, add to, reorder, and/or modify any of the operations shown in FIG. 29. Each of the operations shown in FIG. 29 may be performed in any of the ways described herein.

In operation 2902, a control circuit directs a TPSF generation circuit to operate in a first resolution mode in which the TPSF generation circuit generates, based on photodetector output pulses generated by one more photodetectors, a TPSF with a temporal resolution that has a first temporal resolution value.

In operation 2904, the control circuit receives a command indicating that the TPSF generation circuit is to switch to operating in a second resolution mode.

In operation 2906, the control circuit directs, in response to receiving the command, the TPSF generation circuit to switch from operating in the first resolution mode to operating in a second resolution mode in which the temporal resolution of the TPSF generated by the TPSF generation circuit has a second temporal resolution value different than the first temporal resolution value (e.g., the first temporal resolution value is higher than the second temporal resolution value).

An exemplary system described herein includes a photodetector configured to generate a plurality of photodetector output pulses over time as a plurality of light pulses are applied to and scattered by a target, wherein each photodetector output pulse is generated when the photodetector detects a photon from one of the light pulses that is scattered by the target; a TPSF generation circuit configured to generate, based on the photodetector output pulses, a TPSF representative of a light pulse response of the target; and a control circuit communicatively coupled to the TPSF generation circuit and configured to direct the TPSF generation circuit to selectively operate in a first resolution mode in which a temporal resolution of the TPSF is a first temporal resolution value, and operate in a second resolution mode in which the temporal resolution of the TPSF is a second temporal resolution value different than the first temporal resolution value.

An exemplary system described herein includes a photodetector configured to generate a plurality of photodetector output pulses over time as a plurality of light pulses are applied to and scattered by a target, wherein each photodetector output pulse is generated when the photodetector detects a photon from one of the light pulses that is scattered by the target; and a TPSF generation circuit configured to initially operate in a first resolution mode in which the TPSF generation circuit is configured to generate, based on the photodetector output pulses, a TPSF with a temporal resolution that has a first temporal resolution value, the TPSF representative of a light pulse response of the target, and switch from operating in the first resolution mode to operating in a second resolution mode in which the temporal resolution of the TPSF generated by the TPSF generation circuit has a second temporal resolution value different than the first temporal resolution value.

An exemplary wearable system for use by a user described herein includes a head-mountable component configured to be attached to a head of the user, the head-mountable component comprising a photodetector configured to generate a plurality of photodetector output pulses over time as a plurality of light pulses are applied to and scattered by a target, wherein each photodetector output pulse is generated when the photodetector detects a photon from one of the light pulses that is scattered by the target; a TPSF generation circuit configured to generate, based on the photodetector output pulses, a TPSF representative of a light pulse response of the target; and a control circuit communicatively coupled to the TPSF generation circuit and configured to direct the TPSF generation circuit to selectively operate in a first resolution mode in which a temporal resolution of the TPSF is a first temporal resolution value, and operate in a second resolution mode in which the temporal resolution of the TPSF is a second temporal resolution value different than the first temporal resolution value.

An exemplary apparatus described herein includes a memory storing instructions; and a processor communicatively coupled to the memory and configured to execute the instructions to: direct a TPSF generation circuit to operate in a first resolution mode in which the TPSF generation circuit generates, based on photodetector output pulses generated by one more photodetectors, a TPSF with a temporal resolution that has a first temporal resolution value, receive a command indicating that the TPSF generation circuit is to switch to operating in a second resolution mode, and direct, in response to receiving the command, the TPSF generation circuit to switch from operating in the first resolution mode to operating in a second resolution mode in which the temporal resolution of the TPSF generated by the TPSF generation circuit has a second temporal resolution value different than the first temporal resolution value.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a photodetector configured to generate a plurality of photodetector output pulses over time as a plurality of light pulses are applied to and scattered by a target, wherein each photodetector output pulse is generated when the photodetector detects a photon from one of the plurality of light pulses that is scattered by the target;
a temporal point spread function (TPSF) generation circuit comprising:
a time-to-digital converter (TDC) configured to
record timestamp symbols corresponding to occurrences of the plurality of photodetector output pulses, and
provide an output signal representative of the recorded timestamp symbols; and
a signal processing circuit configured to generate, based on the output signal provided by the TDC, a TPSF representative of a light pulse response of the target;
a measurement time window management circuit configured to perform a calibration procedure for the TDC; and
a control circuit communicatively coupled to the TPSF generation circuit and configured to direct the TPSF generation circuit to selectively
operate, when the calibration procedure is being performed for the TDC, in a first resolution mode in which a temporal resolution of the TPSF is a first temporal resolution value, and
switch, after the calibration procedure has been performed for the TDC, from operating in the first resolution mode to operating in a second resolution mode in which the temporal resolution of the TPSF is a second temporal resolution value, wherein the first temporal resolution value is higher than the second temporal resolution value.

2. The system of claim 1, wherein the TPSF generation circuit further comprises:
a phase lock loop (PLL) circuit having a PLL feedback period defined by a reference clock; and
a timestamp generation circuit configured to
generate, based on at least one signal generated within the PLL circuit, a timestamp signal bus that includes a programmable number of timestamp symbols per PLL feedback period, and
transmit the timestamp signal bus to the TDC;
wherein
the programmable number of timestamp symbols per PLL feedback period defines the temporal resolution of the TPSF; and
the timestamp symbols recorded by the TDC are included in the programmable number of timestamp symbols per PLL feedback period.

3. The system of claim 2, wherein:
the PLL circuit comprises a voltage controlled oscillator having a plurality of stages configured to output a plurality of fine phase signals each having a different phase, and
the timestamp generation circuit is configured to generate the timestamp signal bus based on a subset of the fine phase signals.

4. The system of claim 3, wherein:
the PLL circuit further comprises a feedback divider configured to generate a load signal; and
the timestamp generation circuit comprises:
a course counter configured to receive the load signal generated by the feedback divider, the load signal configured to reset the course counter at a beginning of each PLL feedback period, the course counter configured to output a course count signal comprising a course count up to a maximum value associated with the course counter;
a first register configured to sample the course count signal to generate a course early signal; and
a second register configured to sample the course early signal to generate a course late signal;
wherein the timestamp signal bus comprises the subset of fine phase signals, the course early signal, and the course late signal.

5. The system of claim 3, wherein:
in the first resolution mode, a total number of fine phase signals included in the subset of the fine phase signals used by the timestamp generation circuit to generate the timestamp signal bus is equal to a first value; and
in the second resolution mode, the total number of fine phase signals included in the subset of the fine phase signals used by the timestamp generation circuit to generate the timestamp signal bus is equal to a second value that is different than the first value.

6. The system of claim 2, wherein the control circuit is configured to:
- direct the TPSF generation circuit to operate in the first resolution mode by transmitting a command, to the timestamp generation circuit, that sets the programmable number of timestamp symbols per PLL feedback period to a first value; and
- direct the TPSF generation circuit to switch to operating in the second resolution mode by transmitting a command, to the timestamp generation circuit, that sets the programmable number of timestamp symbols per PLL feedback period to a second value different than the first value.

7. The system of claim 1, wherein:
- the photodetector is included in an array of photodetectors each configured to generate a different set of photodetector output pulses;
- the TDC is included in an array of TDCs each configured to record a different set of timestamp symbols corresponding to occurrences of the different sets of photodetector output pulses and generate different output signals; and
- the signal processing circuit is configured to generate, based on all of the different output signals provided by the array of TDCs, the TPSF.

8. The system of claim 1, wherein:
- the system further comprises a precision timing circuit configured to adjust a temporal position of a measurement time window during which the TDC is configured to monitor for an occurrence of a photodetector output pulse included in the photodetector output pulses;
- the control circuit is configured to
  - receive a command indicating that the precision timing circuit is to adjust the temporal position of the measurement time window; and
  - direct, in response to receiving the command, the TPSF generation circuit to operate in the first resolution mode.

9. The system of claim 1, wherein the control circuit is further configured to direct the TPSF generation circuit to selectively operate in a third resolution mode in which the temporal resolution of the TPSF is a third temporal resolution value different than the first and second temporal resolution values.

10. The system of claim 1, wherein the photodetector comprises a single photon avalanche diode (SPAD).

11. The system of claim 1, wherein the photodetector is included in a wearable device configured to be worn by a user.

12. The system of claim 11, wherein the wearable device includes a head-mountable component configured to be worn on a head of the user.

13. A system comprising:
- a photodetector configured to generate a plurality of photodetector output pulses over time as a plurality of light pulses are applied to and scattered by a target, wherein each photodetector output pulse is generated when the photodetector detects a photon from one of the plurality of light pulses that is scattered by the target;
- a measurement time window management circuit configured to perform a calibration procedure for a time-to-digital converter (TDC); and
- a temporal point spread function (TPSF) generation circuit configured to
  - initially operate, when the calibration procedure is being performed for the TDC, in a first resolution mode in which the TPSF generation circuit is configured to generate, based on the plurality of photodetector output pulses, a TPSF with a temporal resolution that has a first temporal resolution value, the TPSF representative of a light pulse response of the target, and
  - switch, after the calibration procedure has been performed for the TDC, from operating in the first resolution mode to operating in a second resolution mode in which the temporal resolution of the TPSF generated by the TPSF generation circuit has a second temporal resolution value, wherein the first temporal resolution value is higher than the second temporal resolution value.

14. The system of claim 13, wherein the TPSF generation circuit comprises the TDC and a signal processing circuit, wherein:
- the TDC is configured to
  - record timestamp symbols corresponding to occurrences of the photodetector output pulses, and
  - provide an output signal representative of the recorded timestamp symbols; and
- the signal processing circuit is configured to generate, based on the output signal provided by the TDC, the TPSF.

15. The system of claim 14, wherein the TPSF generation circuit further comprises:
- a phase lock loop (PLL) circuit having a PLL feedback period defined by a reference clock; and
- a timestamp generation circuit configured to
  - generate, based on at least one signal generated within the PLL circuit, a timestamp signal bus that includes a programmable number of timestamp symbols per PLL feedback period, and
  - transmit the timestamp signal bus to the TDC;
wherein
- the programmable number of timestamp symbols per PLL feedback period defines the temporal resolution of the TPSF; and
- the timestamp symbols recorded by the TDC are included in the programmable number of timestamp symbols per PLL feedback period.

16. The system of claim 15, wherein:
- the PLL circuit comprises a voltage controlled oscillator having a plurality of stages configured to output a plurality of fine phase signals each having a different phase, and
- the timestamp generation circuit is configured to generate the timestamp signal bus based on a subset of the fine phase signals.

17. The system of claim 16, wherein:
- in the first resolution mode, a total number of fine phase signals included in the subset of the fine phase signals used by the timestamp generation circuit to generate the timestamp signal bus is equal to a first value; and
- in the second resolution mode, the total number of fine phase signals included in the subset of the fine phase signals used by the timestamp generation circuit to generate the timestamp signal bus is equal to a second value that is different than the first value.

18. A wearable system for use by a user, comprising:
- a head-mountable component configured to be attached to a head of the user, the head-mountable component comprising a photodetector configured to generate a plurality of photodetector output pulses over time as a plurality of light pulses are applied to and scattered by a target, wherein each photodetector output pulse is generated when the photodetector detects a photon from one of the plurality of light pulses that is scattered by the target;

a measurement time window management circuit configured to perform a calibration procedure for a time-to-digital converter (TDC);

a temporal point spread function (TPSF) generation circuit configured to generate, based on the plurality of photodetector output pulses, a TPSF representative of a light pulse response of the target; and a control circuit communicatively coupled to the TPSF generation circuit and configured to direct the TPSF generation circuit to selectively operate, when the calibration procedure is being performed for the TDC, in a first resolution mode in which a temporal resolution of the TPSF is a first temporal resolution value, and switch, after the calibration procedure has been performed for the TDC, from operating in the first resolution mode to operating in a second resolution mode in which the temporal resolution of the TPSF is a second temporal resolution value, wherein the first temporal resolution value is higher than the second temporal resolution value.

19. The wearable system of claim 18, wherein the TPSF generation circuit comprises the TDC and a signal processing circuit, wherein:

the TDC is configured to
record timestamp symbols corresponding to occurrences of the photodetector output pulses, and
provide an output signal representative of the recorded timestamp symbols; and the signal processing circuit is configured to generate, based on the output signal provided by the TDC, the TPSF.

20. The wearable system of claim 19, wherein the TPSF generation circuit further comprises:

a phase lock loop (PLL) circuit having a PLL feedback period defined by a reference clock; and a timestamp generation circuit configured to
generate, based on at least one signal generated within the PLL circuit, a timestamp signal bus that includes a programmable number of timestamp symbols per PLL feedback period, and
transmit the timestamp signal bus to the TDC;

wherein
the programmable number of timestamp symbols per PLL feedback period defines the temporal resolution of the TPSF; and
the timestamp symbols recorded by the TDC are included in the programmable number of timestamp symbols per PLL feedback period.

21. The wearable system of claim 20, wherein:

the PLL circuit comprises a voltage controlled oscillator having a plurality of stages configured to output a plurality of fine phase signals each having a different phase, and the timestamp generation circuit is configured to generate the timestamp signal bus based on a subset of the fine phase signals.

22. The wearable system of claim 21, wherein:

in the first resolution mode, a total number of fine phase signals included in the subset of the fine phase signals used by the timestamp generation circuit to generate the timestamp signal bus is equal to a first value; and in the second resolution mode, the total number of fine phase signals included in the subset of the fine phase signals used by the timestamp generation circuit to generate the timestamp signal bus is equal to a second value that is different than the first value.

* * * * *